US009827249B2

(12) United States Patent
Ratilainen et al.

(10) Patent No.: US 9,827,249 B2
(45) Date of Patent: Nov. 28, 2017

(54) USE OF CONDENSED BENZO[B]THIAZINE DERIVATIVES AS CYTOPROTECTANTS

(71) Applicant: ARANDA PHARMA LTD, Kuopio (FI)

(72) Inventors: Jari Ratilainen, Kulho (FI); Gundars Goldsteins, Kuopio (FI)

(73) Assignee: ARANDA PHARMA LTD, Huopio (FI)

( * ) Notice: Subject to any disclaimer, the term of this patent is extended or adjusted under 35 U.S.C. 154(b) by 0 days.

(21) Appl. No.: 14/894,683

(22) PCT Filed: May 30, 2014

(86) PCT No.: PCT/FI2014/050432
§ 371 (c)(1),
(2) Date: Nov. 30, 2015

(87) PCT Pub. No.: WO2014/191632
PCT Pub. Date: Dec. 4, 2014

(65) Prior Publication Data
US 2016/0106754 A1 Apr. 21, 2016

(30) Foreign Application Priority Data
May 31, 2013 (FI) .................................. 20135602

(51) Int. Cl.
A61K 31/542 (2006.01)
C07D 513/04 (2006.01)
(Continued)

(52) U.S. Cl.
CPC .......... *A61K 31/542* (2013.01); *A61K 31/547* (2013.01); *C07D 513/04* (2013.01); *C07D 513/10* (2013.01); *C07D 513/20* (2013.01)

(58) Field of Classification Search
CPC ........................... A61K 31/542; C07D 513/04
(Continued)

(56) References Cited

U.S. PATENT DOCUMENTS 4,861,878 A 8/1989 Fengler et al.

FOREIGN PATENT DOCUMENTS

| WO | WO 99/21560 A1 | 5/1999 |
| WO | 00/53166 A2 | 9/2000 |
| WO | WO 2008/009935 A1 | 1/2008 |

OTHER PUBLICATIONS

Auvin, Serge et al, Bioorganic & Medicinal Chemistry Letters (2006), vol. 16 (6), pp. 1586-1589.*
(Continued)

*Primary Examiner* — Kathrien Cruz
*Assistant Examiner* — Janet L Coppins
(74) *Attorney, Agent, or Firm* — Scully, Scott, Murphy & Presser, P.C.

(57) ABSTRACT

The present invention relates to arylthiazine compounds, metabolites, N-oxides, amides, esters, pharmaceutically acceptable salts, hydrates and solvates thereof and their use as cytoprotectants in the treatment or prophylaxis of diseases or states, either acute or chronic, involving aberrant cellular lipid peroxidation in the central nervous system or in the periphery of the body. The present invention also relates to a method for their preparation and to pharmaceutical composition comprising as an active ingredient one or more of the aforementioned compounds.

14 Claims, 5 Drawing Sheets

(51) Int. Cl.
    *C07D 513/20*    (2006.01)
    *A61K 31/547*    (2006.01)
    *C07D 513/10*    (2006.01)

(58) Field of Classification Search
    USPC .................................................. 514/212.06
    See application file for complete search history.

(56) References Cited

OTHER PUBLICATIONS

Freshney, Ian, In Vitro Culture, 6$^{th}$ edition (2010), pp. 1-5.*
Goodman & Gilman's, The Pharmacological Basis of Therapeutics, 12$^{th}$ edition, pp. 1-4.*
Condorelli et al, "Sintesi di 2,3-diazafenotiazine—Nota II. N-metil-derivati della 1,4-diosso-1,2,3,4-tetraidro 2,3-diazafenotiazina", Bollettino delle Sedute della Accademia Gioenia di Bcienze Naturali in Catania, 1967, vol. 9, pp. 242-251.*
Bare, T.M., "Pyridazino[4,5-b]quinolinediones: Novel Glycine/N-Methyl-D-aspartate Antagonists for the Treatment of Stroke", J. Heterocyclic Chem., 1998, vol. 35, pp. 1171-1186.
Boyer, G. et al., "Synthesis of Substituted Pyrazolo[3.4-b]- and Pyrazolo[4,3-c]Phenothiazine Derivatives", Heterocycles, 1995, vol. 41, No. 3, pp. 487-496.
Condorelli, P. et al., "Sintesi di 2,3-diazafenotiazine—Nota II. N-metil-derivati della 1,4-diosso-1,2,3,4-tetraidro 2,3-diazafenotiazina", Bollettino delle Sedute della Accademia Gioenia di Scienze Naturali in Catania, 1967, vol. 9, pp. 242-251.
Search Report from National Board of Patents and Registration of Finland dated Dec. 18, 2013 in related Finnish Application No. 20135602.
Bare, T.M., "Pyridazino[4,5-b]quinolinediones: Novel Glycine/N-Methyl-D-aspartate Antagonists for the Treatment of Stroke", J. Heterocyclic Chem, 1998, vol. 35, pp. 1171-1186.
Boyer, G. et al., "Synthesis of Substituted Pyrazolo[3,4-b]- and Pyrazolo[4,3-c]Phenothiazine Derivatives", Heterocycles, 1995, vol. 41, No. 3, pp. 487-496.
Pappalardo, G. et al., "Sintesi di 2,3-diazafenotiazine. Nota I. Reazione del 2-acetamidotiofenato sodico con gli esteri etilici degli acidi dibromomaleico e dibromofumarico", Gazzetta Chimica Italiana, 1966, vol. 96, pp. 1147-1157.
Condorelli, P. et al., "Sintesi di 2,3-diazafenotiazine—Nota II. N-metil-derivati della 1,4-diosso-1,2,3,4-tetraidro 2,3-diazafenotiazina", Bollettino delle Sedute della Accademia Gioenia di 5cienze Naturali in Catania, 1967, vol. 9, pp. 242-251.
Boyer, G. et al., "1H and 13C Nuclear Magnetic Resonance Studies of Pyrazolo [c]- and Pyrazolo [b]phenothiazines", Magnetic Resonance in Chemistry, (1994), vol. 32, pp. 537-539.
Chatel, F. et al., "1H and 13C NMR spectral assignments of some tetracyclic phenothiazine derivatives", Magnetic Resonance in Chemistry, (2000), vol. 38, pp. 137-140.
Chatel, F. et al., "Synthesis of new N-Alkyl- and N-Acydioxino-Phenothiazine and Acridinone Derivatives", Heterocycles, (20000, vol. 53, No. 11, pp. 2535-2552.

Chu, J. et al., "Pharmacologic Blockade of 5-Lipoxygenase Improves the Amyloidotic Phenotype of an Alzheimer's Disease Transgenic Mouse Model", AJP, (Apr. 2011), vol. 178, No. 4, pp. 1762-1769.
Freshney, I., "Culture of Animal Cells: A Manual of Basic Technique and Specialized Applications", Sixth Edition, (Mar. 9, 2011), Chapter 1, 5 pages.
Girard, Y. et al., "First Synthesis of Sulfoxides and Sulfones in the 3H-Phenothiazin-3-one and 5H-Benzo[a] phenothiazin-5-one Ring Systems. Addition Reactions with Nucleophiles", J. Org. Chem., (1987) vol. 52, No. 18, pp. 4000-4006.
Bruton, L. et al., "Goodman & Gilman's the Pharmacological Basis of Therapeutics", McGraw-Hill Education, (Jan. 10, 2011) 12th Edition, 4 pages.
Gritsenko, A. N. et al. "Synthesis in phenothiazines. XXXIX. Dimethylpyridophenothiazines", Khimya Geterotsiklicheskikh Soedinenii-Chemistry of Heterocyclic Compounds, Latvijskij Institut Organiceskogo Sinteza, Riga, LV, (Jan. 1, 1975) vol. 1, pp. 50-54, (English abstract).
Jayashree, A., et al., "Synthesis of 5H-Quinolin [3,4-b] Benzothiazin-6(12H)-Ones", Synthetic Communications, (1990), vol. 20, No. 7 pp. 919-924.
Jayashree, A. et al., "Antibacterial Activity of Some Novel 3,4-Hetero Annelated Quinolin-2-Ones", Asian Jr. of Microbiol. Biotech. Env. Sc., (2010), vol. 12, No. 1, pp. 43-47.
Khoshitariya, T. et al., "Pyrrolophenothiazines. 2. Some electrophilic reactions of 3H-pyrrolo[2,3-c]phenothiazine 11,11-dioxide", Chemistry of Heterocyclic Compounds, (Jan. 1, 1985), No. 1, pp. 1095-1098.
Kurkovskaya, L. et al., "PMR study of acetylation of indolobenzo[b]furans, indolobenzo[b]thiophenes, pyrrolophenothiazine dioxide under Friedel-Crafts reaction conditions", Khimiya Geterotsikilicheskikh Soedinenii-Chemistry of Heterocyclic Compounds, (Jan. 1, 1995), No. 8, pp. 1078-1091, (English Abstract).
Lopez-Alvarado, P. et al., "Fused Imidazophenothizazines: Synthesis of 2-methyl-3-phenyl-6h-Imidazo[4,5-c]. Phenothiazine", Heterocycles, (1990), vol. 31, No. 11, 14 pages.
Lopez-Alvarado, P. et al., "Fused Imidazophenothiazines: Studies on the Bemthsen Thionation of 1-Methyl-6-(p-Tolylamino)Benzimidazole and 2-Methyl-1-Phenylbenzimidazole", Heterocycles, (1991), vol. 32, No. 5, 10 pages.
Palavandishvili, G. et al., "Pyrrolophenothiazines. 1. Synthesis of isomeric pyrrolophenothiazine dioxides", Chemistry of Heterocyclic Compounds, (Dec. 1, 1981), vol. 17, No. 12, 4 pages.
Serge, A. et al., "Novel dual inhibitors of calpain and lipid peroxidation with enhanced cellular activity", Bioorg. Med. Chem. Lett, (2006), vol. 16, pp. 1586-1589.
Taubl, A. E. et al., "Thermolytic Ring Closure Reactions of 4-Azido-3-phenylsulfanyl-and 4-Azido-3-phenylsulfonyl-2-quinolones to 12H-Quinolino-[3,4-b][1,4]benzothiazin-6(5H)-ones [1]", Journal of Heterocyclic Chemistry, (Nov. 1, 2002), vol. 39, No. 6, pp. 1259-1264.
International Search Report dated Oct. 13, 2014 issued in PCT/FI2014/050432.
European Office Action dated Feb. 17, 2017 issued in corresponding European Application No. 14 734 525.0.

* cited by examiner

USE OF CONDENSED BENZO[B]THIAZINE DERIVATIVES AS CYTOPROTECTANTS

FIELD OF THE INVENTION

The present invention is in the field of medicinal chemistry and relates to arylthiazine compounds, metabolites, N-oxides, amides, esters, pharmaceutically acceptable salts, hydrates, and solvates thereof, and their use as cytoprotectants in the treatment or prophylaxis of diseases or states, either acute or chronic, involving aberrant cellular lipid peroxidation in the central nervous system or in the periphery of the body. The present invention also relates to a method for their preparation and to a pharmaceutical composition comprising as an active ingredient one or more of the aforementioned compounds.

BACKGROUND OF THE INVENTION

Aging of an organism is associated with a gradual impairment of cellular functions and viability. This is due to an increased impact of various metabolic, dietary or environment derived insults upon cells and associated with diminished capacity of cells to cope with these changes during aging. This imbalance between harmful exposures and protection leads to heterogeneous progressive chronic diseases such as atherosclerosis and neurodegeneration as well as predisposes target organs to further cellular injury in acute conditions like myocardial or cerebral ischemic stroke.

Due to the changes in life styles and increasing number of aged people globally, the socio-economic burden of diseases and states associated with cellular damage is increasing exponentially. While the symptomatic therapy of many age-associated diseases and conditions has progressed considerably, there remains a huge need to prevent, delay the onset, or slow down the expected progression of cellular degeneration underlying these diseases. Such peripheral and central degenerative diseases and conditions associated with aging include Alzheimer's disease and other forms of dementia, amyotrophic lateral sclerosis, atherosclerosis, cancer, Huntington's disease, ischemic or hemorrhagic stroke, liver cirrhosis and non-alcoholic liver diseases, metabolic disorders, multiple sclerosis, noise induced hearing loss, Parkinson's disease, retinal degeneration, and renal diseases.

It has become apparent that while such diseases or states may have their unique etiological factors, they share many common molecular mechanisms leading to impaired function and reduced cellular viability in various target organs and their compartments. Lipids, proteins and DNA are sensitive to oxidative damage. One common pathological feature of age-associated diseases is increased and aberrant oxidation of lipids (reviewed for example in Negre-Salvayre et al. Free Radic Res 2010 44(10):1125-1171), which is known to be an important factor leading to cell death.

The process of lipid peroxidation is mediated through both enzymatic and non-enzymatic pathways. Enzymatic pathways involve lipo-oxygenases and cyclo-oxygenases acting at the polyunsaturated fatty acids (PUFAs) present as free or engaged in lipid complexes such as cell membrane phospholipids or lipoproteins. Non-enzymatic reactions on PUFAs (such as linoleic acid, arachidonic acid) involve ferryl radical, peroxynitrite, hydroperoxyl and hydroxyl radicals among others as possible mediators. Several factors, such as impaired mitochondrial function or inflammation, occurring in central nervous system and peripheral disorders can contribute to the generation of the above mentioned reactive oxygen and nitrogen mediators attacking vital phospholipid components in biological membranes. Lipid hydroperoxides (LOON) themselves are reactive oxygen species capable of oxidizing other macromolecules. Majority of the lipid hydroperoxides is, however, converted non-enzymatically to secondary products including electrophiles causing further dysfunction and damage in cells and leading to the acceleration of secondary lipid peroxidation and ultimately to cell death. Enhanced lipid peroxidation also contributes to the generation of inflammatory response and propagation of inflammatory processes in diseased tissues.

Diseases or states, either acute or chronic, involving aberrant cellular lipid peroxidation in the central nervous system or in the periphery of the body are known to include Alzheimer's disease and other forms of dementia including tauopathies, such as frontotemporal dementia and parkinsonism linked to chromosome 17, progressive supranuclear palsy and corticobasal degeneration, amyotrophic lateral sclerosis, atherosclerosis, cancer, Huntington's disease, ischemic or hemorrhagic stroke, ischemic bowel disease and limb ischemia, liver cirrhosis and non-alcoholic liver diseases, metabolic disorders, multiple sclerosis, myocardial ischemia, noise induced hearing loss, Parkinson's disease, retinal degeneration, renal diseases as well as traumatic brain or spinal cord injury, radiation associated normal tissue injury, liver transplantation induced stenosis, neonatal hypoxic-ischemic injury, adverse cerebral outcomes after cardiac bypass surgery, and HIV-associated neurocognitive disorders.

The cells employ various enzymatic and chemical reactions to defend against the formation and accumulation of lipid hydroperoxides. However, the function of most of the cellular antioxidant systems is dependent on reducing equivalents such as glutathione, which is depleted upon aging and in early stages of pathogenic processes, rendering these defense mechanisms vulnerable.

Therefore, treatment strategies based on elimination of lipid hydroperoxides and limiting their detrimental effects on cellular macromolecules is expected to provide cytoprotection and be of great advantage in the treatment or prophylaxis of age-associated degenerative diseases and other states related to aberrant lipid peroxidation. An object of the present disclosure is to provide compounds useful as cytoprotectants and which may be used for the treatment or prophylaxis of peripheral and central degenerative disorders, in particular in the treatment of mammals, including humans.

Known from CAPlus-database and available from commercial sources are 4,4-dimethyl-2,4,5,6-tetrahydropyrazolo[4,3-c]phenothiazine and 4,4-dimethyl-2-phenyl-2,4,5,6-tetrahydropyrazolo[4,3-c]phenothiazine which fall under the definition of the present invention. However, no field of use or identification data is given for these molecules.

BRIEF DESCRIPTION OF THE INVENTION

It has been surprisingly found that a specific group of compounds containing an arylthiazine backbone as disclosed in the present application can limit the damage caused by lipid hydroperoxides and/or increase the viability of cells exposed to harmful lipid hydroperoxides, act as potent molecules preventing oxidative, nitrosative and/or mitochondrial dysfunction induced cell death in vitro and/or suppress production of inflammatory mediators. They can also increase the viability and integrity of dopaminergic neurons upon neurotoxic insult in nematode *C. elegans* in vivo.

The present invention provides compounds of formula (I) for use as medicaments, in particular for use in the treatment of a condition where elimination of lipid hydroperoxides and/or limiting their detrimental effects on cellular macromolecules is desired. The present invention further provides compounds of formula (I) for use in the treatment or prevention of diseases or states, either acute or chronic, involving aberrant cellular lipid peroxidation in the central nervous system or in the periphery of the body.

The present invention also provides novel arylthiazine compounds of formula (I). The present invention further provides pharmaceutical compositions comprising one or more compounds of formula (I). The present invention also provides a method for the preparation of novel compounds of formula (I).

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figure 1A:
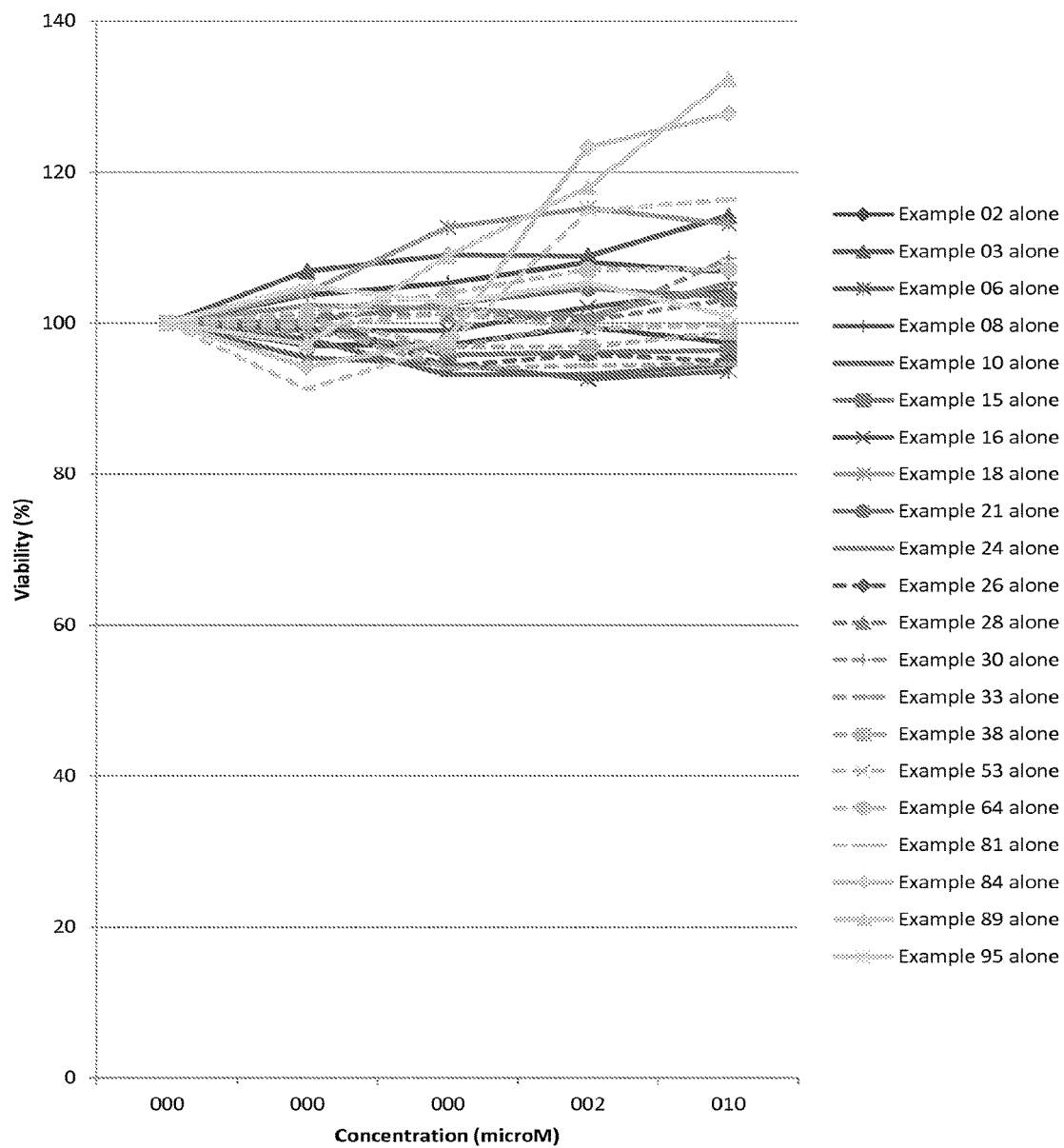
FIG. 1A, 1B: summarize data showing the percentage of viable cells when incubated in the presence of increasing (0-10 µM) concentrations of specified example compounds of the present invention a) without linoleic acid hydroperoxide (LOOH) (FIG. 1A) or b) upon LOOH induced cell death in undifferentiated PC12 cells (FIG. 1B)

The present invention relates to arylthiazine compounds having formula (I), $$(R1)_m \text{—[arylthiazine ring with } G_1, G_2, G_3, G_4, G_5, G_6, G_7, G_8, \text{ N—H, S(=O)}_i\text{]} \quad (I)$$

wherein
(i) G1, G2, G3, and G4 are each C or N, provided that at least one of G1, G2, G3, and G4 is C;
(ii-a) G5 is C=O; and
G6 is N(R6) or C(R7)$_2$; or (ii-b) G5 and G6 form together a 5 or 6 membered unsaturated heterocyclic ring comprising one or two heteroatoms selected from N, O, and S, optionally substituted one or two times with R5;
(iii) G7 is C(R7)$_2$, N(R6), O, S, SO, or SO$_2$, provided that when G6 and G8 are each —CH$_2$—, G7 is N(R6), O, S, SO, or SO$_2$; and
(iv) G8 is [CH$_2$]$_k$C(R8)$_2$, C(R8)$_2$CH$_2$, C(R8)$_2$C(R8)$_2$, [CH$_2$]$_n$, or (C=O);
whereby
each R1 is independently selected from a group consisting of halogen, cyano, nitro, OR', C$_{1-6}$-(per)haloalkoxy, N(R')$_2$, SR'. SOR', SO$_2$R', C$_{1-6}$-alkyl, C$_{1-6}$-(per)haloalkyl, COOR', and CON(R')$_2$; and/or two adjacent R1 together with the ring atoms they are attached to form a 5 to 7 membered ring optionally comprising 1 to 3 heteroatoms selected from N, O, and S, in particular from a group consisting of halogen, cyano, nitro, OR', C$_{1-6}$-(per)haloalkoxy, N(R')$_2$, C$_{1-6}$-alkyl, C$_{1-6}$-(per)haloalkyl, COOR', and CON(R')$_2$; and/or two adjacent R1 together with the ring atoms they are attached to form a 5 to 7 membered ring optionally comprising 1 to 3 heteroatoms selected from N, O, and S;
each R5 is independently selected from a group consisting of halogen, cyano, nitro, OR', oxo, C$_{1-6}$-(per)haloalkoxy, N(R')$_2$, C$_{1-6}$-alkyl, C$_{1-6}$-(per)haloalkyl, COOR', CON(R')$_2$; —[CH$_2$]$_k$Ar, and C$_{1-3}$-alkyl-(C=O)— in particular from a group consisting of halogen, cyano, nitro, OR', C$_{1-6}$-(per)haloalkoxy, N(R')$_2$, C$_{1-6}$-alkyl, C$_{1-6}$-(per)haloalkyl, COOR', CON(R')$_2$; —[CH$_2$]$_k$Ar, and C$_{1-3}$-alkyl-(C=O)—;
each R6 is independently selected from a group consisting of H, C$_{1-6}$-alkyl, C$_{1-6}$-(per)haloalkyl, C$_{2-6}$-alkenyl, C$_{2-6}$-alkynyl, OR', N(R'')$_2$, C$_{1-3}$-alkyl-(C=O)—, C$_{1-3}$-alkyl-(C=O)—NH—, —[CH$_2$]$_k$Ar, and —[CH$_2$]$_k$Cy;
each R7 is independently selected from a group consisting of H, C$_{1-6}$-alkyl, C$_{1-6}$-(per)haloalkyl, OR''—C$_{1-3}$-alkylenyl, N(R')$_2$—C$_{1-3}$-alkylenyl, (R')$_2$NCO—C$_{1-3}$-alkylenyl, COOR', —[CH$_2$]$_k$Ar, and —[CH$_2$]$_k$Cy; or two R7 attached to a same ring carbon form together with the said ring carbon a 3 to 7 membered aliphatic carbocyclic or heterocyclic ring optionally substituted one or two times with R5;
each R8 is independently C$_{1-6}$-alkyl, or C$_{1-6}$-(per)haloalkyl; or two R8 together with the ring carbon they are attached to form a 3 to 7 membered aliphatic or heteroaliphatic ring optionally substituted one or two times with R5;
or one R7 and one R8 located on G7 and G8, respectively, form together a further bond between G7 and G8; and the other R7 and the other R8 are each independently H or as defined above or form together with the ring carbons they are attached to a 5 to 7 membered unsaturated carbocyclic or heterocyclic ring optionally substituted one or two times with R5;
or one R7 and one R8 located on G7 and G8, respectively, form together with the ring carbons they are attached to a 3 to 7 membered aliphatic carbocyclic or heterocyclic ring optionally substituted one or two times with R5; and the other R7 and the other R8 are each H;
each R' is independently H or C$_{1-6}$-alkyl; or when attached to N each R' may alternatively be C$_{1-3}$-alkoxy-C$_{1-3}$-alkylenyl, or two R' may form together with the N they are attached to a 5 to 6 membered saturated heterocyclic ring optionally comprising one further heteroatom selected form N, O and S;
each R'' is independently selected from a group consisting of R', CN—C$_{1-3}$-alkylenyl, C$_{1-3}$-alkoxy-C$_{1-3}$-alkylenyl, C$_{1-6}$-alkenyl, C$_{1-6}$-alkynyl, and C$_{1-3}$-alkyl-(C=O)—; or each R'' forms together with a R7 or R8, respectively, an C$_{1-3}$-alkylene bridge, in particular each R'' is independently selected from a group consisting of R', $C_{1-3}$-alkoxy-$C_{1-3}$-alkylenyl, $C_{1-6}$-alkenyl, $C_{1-6}$-alkynyl, and $C_{1-3}$-alkyl-(C=O)—; or each R" forms together with a R7 or R8, respectively, an $C_{1-3}$-alkylene bridge;

Ar is phenyl or 5 to 6 membered aromatic heterocyclic ring comprising one, two or three N atoms, said phenyl or ring being optionally substituted one or two times with R5;

Cy is 3 to 7 membered aliphatic carbocyclic or heterocyclic ring optionally substituted one or two times with R5;

i is 0, 1, or 2;

k is 0 or 1;

m is 0, 1, 2, 3, or 4;

n is 0, 1, 2, or 3;

or metabolite, N-oxide, pharmaceutically acceptable salt, hydrate, or solvate thereof;

for use in treatment of a condition where elimination of lipid hydroperoxides and/or limiting their detrimental effects on cellular macromolecules is desired, or in treatment or prevention of a disease or state, either acute or chronic, involving aberrant cellular lipid peroxidation in the central nervous system or in the periphery of the body.

The present invention relates to arylthiazine compounds having formula (I),

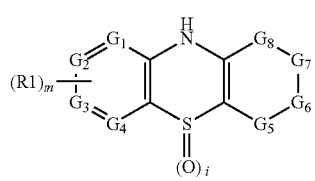

(I)

wherein (i) G1, G2, G3, and G4 are each C or N, provided that at least one of G1, G2, G3, and G4 is C;

(ii-a) G5 is C=O; and

G6 is N(R6) or C(R7)$_2$; or (ii-b) G5 and G6 form together a 5 or 6 membered unsaturated heterocyclic ring comprising one or two heteroatoms selected from N, O, and S, optionally substituted one or two times with R5;

(iii) G7 is C(R7)$_2$, N(R6), O, S, SO, or SO$_2$, provided that when G6 and G8 are each —CH$_2$—, G7 is N(R6), O, S, SO, or SO$_2$; and (iv) G8 is [CH$_2$]$_k$C(R8)$_2$, C(R8)$_2$CH$_2$, C(R8)$_2$C(R8)$_2$, [CH$_2$]$_n$, or (C=O);

whereby each R1 is independently selected from a group consisting of halogen, cyano, nitro, OR', $C_{1-6}$-(per)haloalkoxy, N(R')$_2$, SR'. SOR', SO$_2$R', $C_{1-6}$-alkyl, $C_{1-6}$-(per)haloalkyl, COOR', and CON(R')$_2$; and/or two adjacent R1 together with the ring atoms they are attached to form a 5 to 7 membered ring optionally comprising 1 to 3 heteroatoms selected from N, O, and S, in particular from a group consisting of halogen, cyano, nitro, OR', $C_{1-6}$-(per)haloalkoxy, N(R')$_2$, $C_{1-6}$-alkyl, $C_{1-6}$-(per)haloalkyl, COOR', and CON(R')$_2$; and/or two adjacent R1 together with the ring atoms they are attached to form a 5 to 7 membered ring optionally comprising 1 to 3 heteroatoms selected from N, O, and S;

each R5 is independently selected from a group consisting of halogen, cyano, nitro, OR', oxo, $C_{1-6}$-(per)haloalkoxy, N(R')$_2$, $C_{1-6}$-alkyl, $C_{1-6}$-(per)haloalkyl, COOR', CON(R')$_2$; —[CH$_2$]$_k$Ar, and $C_{1-3}$-alkyl-(C=O)— in particular from a group consisting of halogen, cyano, nitro, OR', $C_{1-6}$-(per)haloalkoxy, N(R')$_2$, $C_{1-6}$-alkyl, $C_{1-6}$-(per)haloalkyl, COOR', CON(R')$_2$; —[CH$_2$]$_k$Ar, and $C_{1-3}$-alkyl-(C=O)—;

each R6 is independently selected from a group consisting of H, $C_{1-6}$-alkyl, $C_{1-6}$-(per)haloalkyl, $C_{2-6}$-alkenyl, $C_{2-6}$-alkynyl, OR', N(R")$_2$, $C_{1-3}$-alkyl-(C=O)—, $C_{1-3}$-alkyl-(C=O)—NH—, —[CH$_2$]$_k$Ar, and —[CH$_2$]$_k$Cy;

each R7 is independently selected from a group consisting of H, $C_{1-6}$-alkyl, $C_{1-6}$-(per)haloalkyl, OR"'—$C_{1-3}$-alkylenyl, N(R')$_2$—$C_{1-3}$-alkylenyl, (R')$_2$NCO—$C_{1-3}$-alkylenyl, COOR', —[CH$_2$]$_k$Ar, and —[CH$_2$]$_k$Cy; or two R7 attached to a same ring carbon form together with the said ring carbon a 3 to 7 membered aliphatic carbocyclic or heterocyclic ring optionally substituted one or two times with R5;

each R8 is independently $C_{1-6}$-alkyl, or $C_{1-6}$-(per)haloalkyl; or two R8 together with the ring carbon they are attached to form a 3 to 7 membered aliphatic or heteroaliphatic ring optionally substituted one or two times with R5;

or one R7 and one R8 located on G7 and G8, respectively, form together a further bond between G7 and G8; and the other R7 and the other R8 are each independently H or as defined above or form together with the ring carbons they are attached to a 5 to 7 membered unsaturated carbocyclic or heterocyclic ring optionally substituted one or two times with R5;

or one R7 and one R8 located on G7 and G8, respectively, form together with the ring carbons they are attached to a 3 to 7 membered aliphatic carbocyclic or heterocyclic ring optionally substituted one or two times with R5; and the other R7 and the other R8 are each H;

each R' is independently H or $C_{1-6}$-alkyl; or when attached to N each R' may alternatively be $C_{1-3}$-alkoxy-$C_{1-3}$-alkylenyl, or two R' may form together with the N they are attached to a 5 to 6 membered saturated heterocyclic ring optionally comprising one further heteroatom selected form N, O and S;

each R" is independently selected from a group consisting of R', CN—$C_{1-3}$-alkylenyl, $C_{1-3}$-alkoxy-$C_{1-3}$-alkylenyl, $C_{1-6}$-alkenyl, $C_{1-6}$-alkynyl, and $C_{1-3}$-alkyl-(C=O)—; or each R" forms together with a R7 or R8, respectively, an $C_{1-3}$-alkylene bridge, in particular each R" is independently selected from a group consisting of R', $C_{1-3}$-alkoxy-$C_{1-3}$-alkylenyl, $C_{1-6}$-alkenyl, $C_{1-6}$-alkynyl, and $C_{1-3}$-alkyl-(C=O)—; or each R" forms together with a R7 or R8, respectively, an $C_{1-3}$-alkylene bridge;

Ar is phenyl or 5 to 6 membered aromatic heterocyclic ring comprising one, two or three N atoms, said phenyl or ring being optionally substituted one or two times with R5;

Cy is 3 to 7 membered aliphatic carbocyclic or heterocyclic ring optionally substituted one or two times with R5;

i is 0, 1, or 2;

k is 0 or 1;

m is 0, 1, 2, 3, or 4;

n is 0, 1, 2, or 3;

or metabolite, N-oxide, pharmaceutically acceptable salt, hydrate, or solvate thereof;

excluding 8-chloro-2,3-dihydro-1H-benzo[b]pyridazino[4,5-e][1,4]thiazine-1,4-(10H)-dione;

8-chloro-2,3-dihydro-1H-benzo[b]pyridazino[4,5-e][1,4]thiazine-1,4-(10H)-dione 5-oxide;

8-chloro-2,3-dihydro-1H-benzo[b]pyridazino[4,5-e][1,4]thiazine-1,4-(10H)-dione 5,5-dioxide;

for use as a medicament.

The present invention further relates to novel arylthiazine compounds having formula (I)

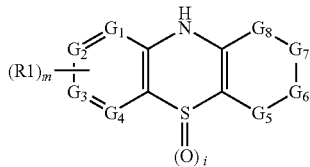

wherein
(i) G1, G2, G3, and G4 are each C or N, provided that at least one of G1, G2, G3, and G4 is C;
(ii-a) G5 is C=O; and
G6 is N(R6) or C(R7)$_2$; or
(ii-b) G5 and G6 form together a 5 or 6 membered unsaturated heterocyclic ring comprising one or two heteroatoms selected from N, O, and S, optionally substituted one or two times with R5;
(iii) G7 is C(R7)$_2$, N(R6), O, S, SO, or SO$_2$, provided that when G6 and G8 are each —CH$_2$—, G7 is N(R6), O, S, SO, or SO$_2$; and
(iv) G8 is [CH$_2$]$_k$C(R8)$_2$, C(R8)$_2$CH$_2$, C(R8)$_2$C(R8)$_2$, [CH$_2$]$_n$, or (C=O);
whereby
each R1 is independently selected from a group consisting of halogen, cyano, nitro, OR', C$_{1-6}$-(per)haloalkoxy, N(R')$_2$, SR'. SOR', SO$_2$R', C$_{1-6}$-alkyl, C$_{1-6}$-(per)haloalkyl, COOR', and CON(R')$_2$; and/or two adjacent R1 together with the ring atoms they are attached to form a 5 to 7 membered ring optionally comprising 1 to 3 heteroatoms selected from N, O, and S, in particular from a group consisting of halogen, cyano, nitro, OR', C$_{1-6}$-(per)haloalkoxy, N(R')$_2$, C$_{1-6}$-alkyl, C$_{1-6}$-(per)haloalkyl, COOR', and CON(R')$_2$; and/or two adjacent R1 together with the ring atoms they are attached to form a 5 to 7 membered ring optionally comprising 1 to 3 heteroatoms selected from N, O, and S;
each R5 is independently selected from a group consisting of halogen, cyano, nitro, OR', oxo, C$_{1-6}$-(per)haloalkoxy, N(R')$_2$, C$_{1-6}$-alkyl, C$_{1-6}$-(per)-haloalkyl, COOR', CON(R')$_2$; —[CH$_2$]$_k$Ar, and C$_{1-3}$-alkyl-(C=O)—, in particular from a group consisting of halogen, cyano, nitro, OR', C$_{1-6}$-(per)haloalkoxy, N(R')$_2$, C$_{1-6}$-alkyl, C$_{1-6}$-(per)haloalkyl, COOR', CON(R')$_2$; —[CH$_2$]$_k$Ar, and C$_{1-3}$-alkyl-(C=O)—;
each R6 is independently selected from a group consisting of H, C$_{1-6}$-alkyl, C$_{1-6}$-(per)haloalkyl, C$_{2-6}$-alkenyl, C$_{2-6}$-alkynyl, OR', N(R'')$_2$, C$_{1-3}$-alkyl-(C=O)—, C$_{1-3}$-alkyl-(C=O)—NH—, —[CH$_2$]$_k$Ar, and —[CH$_2$]$_k$Cy;
each R7 is independently selected from a group consisting of H, C$_{1-6}$-alkyl, C$_{1-6}$-(per)haloalkyl, OR''—C$_{1-3}$-alkylenyl, N(R')$_2$—C$_{1-3}$-alkylenyl, (R')$_2$NCO—C$_{1-3}$-alkylenyl, COOR', —[CH$_2$]$_k$Ar, and —[CH$_2$]$_k$Cy; or two R7 attached to a same ring carbon form together with the said ring carbon a 3 to 7 membered aliphatic carbocyclic or heterocyclic ring optionally substituted one or two times with R5;
each R8 is independently C$_{1-6}$-alkyl, or C$_{1-6}$-(per)haloalkyl; or two R8 together with the ring carbon they are attached to form a 3 to 7 membered aliphatic or heteroaliphatic ring optionally substituted one or two times with R5;
or one R7 and one R8 located on G7 and G8, respectively, form together a further bond between G7 and G8; and the other R7 and the other R8 are each independently H or as defined above or form together with the ring carbons they are attached to a 5 to 7 membered unsaturated carbocyclic or heterocyclic ring optionally substituted one or two times with R5;
or one R7 and one R8 located on G7 and G8, respectively, form together with the ring carbons they are attached to a 3 to 7 membered aliphatic carbocyclic or heterocyclic ring optionally substituted one or two times with R5; and the other R7 and the other R8 are each H;
each R' is independently H or C$_{1-6}$-alkyl; or when attached to N each R' may alternatively be C$_{1-3}$-alkoxy-C$_{1-3}$-alkylenyl, or two R' may form together with the N they are attached to a 5 to 6 membered saturated heterocyclic ring optionally comprising one further heteroatom selected form N, O and S;
each R'' is independently selected group a group consisting of R', CN—C$_{1-3}$-alkylenyl, C$_{1-3}$-alkoxy-C$_{1-3}$-alkylenyl, C$_{1-6}$-alkenyl, C$_{1-6}$-alkynyl, and C$_{1-3}$-alkyl-(C=O)—; or each R'' forms together with a R7 or R8, respectively, an C$_{1-3}$-alkylene bridge, in particular each R'' is independently selected from a group consisting of R', C$_{1-3}$-alkoxy-C$_{1-3}$-alkylenyl, C$_{1-6}$-alkenyl, C$_{1-6}$-alkynyl, and C$_{1-3}$-alkyl-(C=O)—; or each R'' forms together with a R7 or R8, respectively, an C$_{1-3}$-alkylene bridge;
Ar is phenyl or 5 to 6 membered aromatic heterocyclic ring comprising one, two or three N atoms, said phenyl or ring being optionally substituted one or two times with R5;
Cy is 3 to 7 membered aliphatic carbocyclic or heterocyclic ring optionally substituted one or two times with R5;
i is 0, 1, or 2;
k is 0 or 1;
m is 0, 1, 2, 3, or 4;
n is 0, 1, 2, or 3;
or metabolite, N-oxide, amide, ester, pharmaceutically acceptable salt, hydrate, or solvate thereof;
excluding 4,4-dimethyl-2,4,5,6-tetrahydropyrazolo[4,3-c]phenothiazine; 4,4-dimethyl-2-phenyl-2,4,5,6-tetrahydropyrazolo[4,3-c]phenothiazine, 8-chloro-2,3-dihydro-1H-benzo[b]pyridazino[4,5-e][1,4]thiazine-1,4(10H)-dione; 8-chloro-2,3-dihydro-1H-benzo[b]pyridazino[4,5-e][1,4]thiazine-1,4 (10H)-dione 5-oxide; 8-chloro-2,3-dihydro-1H-benzo[b]pyridazino[4,5-e][1,4]thiazine-1,4-(10H)-dione 5,5-dioxide; 2,3-dihydro-1H-benzo[b]pyridazino[4,5-e][1,4]thiazine-1,4 (10H)-dione; 3-methyl-2,3-dihydro-1H-benzo[b]pyridazino[4,5-e][1,4]thiazine-1,4(10H)-dione; 2,3-dimethyl-2,3-dihydro-1H-benzo[b]pyridazino[4,5-e]-[1,4]thiazine-1,4 (10H)-dione; 1-methyl-1,6-dihydropyrazolo[4,3-c]phenothiazine; 1,9-dimethyl-1,6-dihydropyrazolo[4,3-c]phenothiazine; 9-methoxy-1-methyl-1,6-dihydropyrazolo[4,3-c]phenothiazine; and 2-methyl-2,6-dihydropyrazolo-[4,3-c]phenothiazine.
Particularly the present invention relates to compounds of formula (I) as defined herein and pharmaceutically acceptable salts thereof.
In particular the present invention relates to compounds of formula (I) wherein i is 0, i.e. having formula (I').

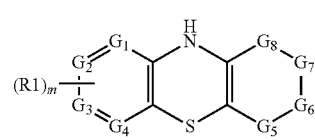

wherein G1, G2, G3, G4, G5, G6, G7, G8, R1, and m are as defined herein.

Further particularly the invention relates to compounds of formula (I) wherein G5 is —(C═O)—; and G6 is NR6 or CH$_2$.

In a class of the present invention G1, G2, G3, and G4 are each C. In another class of the invention G1, G2, and G4 are each N or C, provided that at least two of G1, G2, and G4 are C, and G3 is C. In yet another class of the invention G1, G2, and G4 are each N or C, provided that at least one of G1, G2, and G4 are C, and G3 is C. In still another class of the invention G1, G2, and G4 are each N, and G3 is C.

In a further class of the present invention m is 0, 1, or 2; and each R1 is independently selected from a group consisting of halogen, C$_{1-6}$-alkoxy, C$_{1-6}$-(per)haloalkoxy, and N(R')$_2$.

In a subclass of the invention, the invention relates to compounds of formula (I) wherein G5 is —(C═O)—; and G6 is NR6; in particular to compounds having formula (Ia)

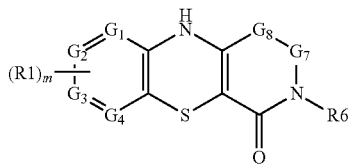

Ia wherein G1, G2, G3, G4, R1, m, G7, G8, and R6 are as defined herein.

In an aspect of this subclass R6 is H. In an alternative aspect of this subclass R6 is C$_{1-2}$-alkyl or C$_{1-2}$-(per)haloalkyl. In a further alternative aspect of this subclass R6 is OH.

In a further aspect of this subclass G1, G2, G3, and G4 are each C. In yet a further aspect of this subclass m is 0, 1, or 2. In particular each R1 is selected from a group consisting of halogen, methoxy, trifluoromethoxy, —NHMe, and —NMe$_2$.

In yet a further aspect of this subclass G7 is C(R7)$_2$. In particular both R7 are C$_{1-6}$-alkyl, such as methyl or ethyl, or methoxy-C$_{1-3}$-alkylenyl; or form together with the ring carbon they are attached to a 3 to 7 membered aliphatic carbocyclic or heterocyclic ring optionally substituted one or two times with R5. Alternatively one R7 is H and the other R7 is as defined herein, in particular C$_{1-6}$-alkyl, —[CH$_2$]$_k$Ar, —[CH$_2$]$_k$Cy, or C$_{1-3}$-alkoxy-C$_{1-3}$-alkylenyl.

In still a further aspect of this subclass G8 is CH$_2$ or —(C═O)—, in particular CH$_2$. In an alternative aspect of this subclass G8 is C(R8)$_2$. In particular both R8 are C$_{1-6}$-alkyl, such as methyl or ethyl, or form together with the ring carbon they are attached to a 3 to 7 membered aliphatic carbocyclic or heterocyclic ring optionally substituted one or two times with R5. In further alternative aspect of this subclass G7 is CH$_2$. In a further alternative aspect of this subclass G7 is CH$_2$ and G8 is [CH$_2$]$_n$, wherein n is preferably 1 or 2.

In yet a further alternative aspect of this subclass G7 is C(R7)$_2$ and G8 is C(R8)$_2$. In particular both R7 and both R8 are C$_{1-3}$-alkyl, such as methyl or ethyl, or form together with the respective ring carbon they are attached to a 3 to 7 membered aliphatic carbocyclic or heterocyclic ring optionally substituted one or two times with R5. In still another further alternative aspect of this subclass one R7 and one R8 located on G7 and G8, respectively, form together a further bond between G7 and G8; and the other R7 and the other R8 are each independently H or as defined above, in particular R8 is H and R7 is as defined herein, or form together with the ring carbons they are attached to a 5 to 7 membered unsaturated carbocyclic or heterocyclic ring optionally substituted one or two times with R5.

In another subclass of the invention, the invention relates to compounds of formula (I) wherein G5 is —(C═O)—; and G7 is O, S, or NR6, in particular NH, having formula (Ib)

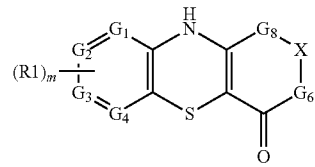

Ib wherein X is O, S, SO, SO$_2$, or NR6; and G1, G2, G3, G4, R1, m, G5, G8, and R6 are as defined herein.

In an aspect of this subclass X is NR6. In particular R6 is H, C$_{1-2}$-alkyl, or C$_{1-2}$-(per)haloalkyl. Alternatively R6 is other than H, preferably C$_{1-3}$-alkyl-(C═O)—. In a further alternative aspect of this subclass R6 is OH.

In yet an alternative aspect of this subclass X is O.

In a further aspect of this subclass G1, G2, G3, and G4 are each C. In yet a further aspect of this subclass m is 0, 1, or 2. In particular each R1 is selected from a group consisting of halogen, methoxy, trifluoromethoxy, —NHMe and —NMe$_2$.

In yet a further aspect of this subclass G6 is C(R7)$_2$. In particular both R7 are H, or C$_{1-6}$-alkyl, such as methyl or ethyl; or form together with the ring carbon they are attached to a 3 to 7 membered aliphatic carbocyclic or heterocyclic ring optionally substituted one or two times with R5. Preferably both R7 are H.

In a further aspect of this subclass G8 is CH$_2$. In an alternative aspect of this subclass G8 is C(R8)$_2$. In particular both R8 are C$_{1-6}$-alkyl, such as methyl or ethyl; or form together with the ring carbon they are attached to a 3 to 7 membered aliphatic carbocyclic or heterocyclic ring optionally substituted one or two times with R5.

In yet another subclass of the invention, the invention relates to compounds of formula (I), wherein G5 and G6 form together a 5 or 6 membered unsaturated heterocyclic ring comprising one or two heteroatoms selected from N, O, and S, in particular two N atoms.

In an aspect of this subclass the invention relates to compounds having formula (Ic)

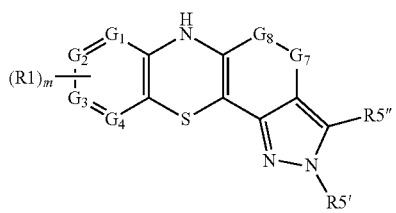

Ic wherein R5' and R5" are each independently H or R5; and G1, G2, G3, G4, R', m, G7, G8, and R5 are as defined herein. In particular G8 is C(R8)$_2$, CH$_2$ or —(C═O)—, more particularly CH$_2$ or —(C═O)—; and G7 is C(R7)$_2$. In particular R5' is C$_{1-3}$-alkyl-(C=O)— and R5" is H; or R5' is H and R5" is halogen or N(R')$_2$.

In alternative aspect of this subclass the invention relates to compounds having formula (Id)

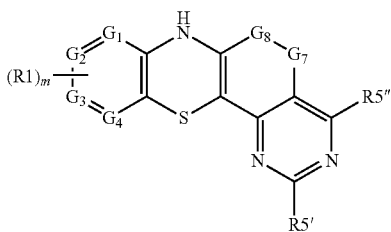

Id wherein R5' and R5" are each independently H or R5; and G1, G2, G3, G4, R1, m, G7, G8, and R5 are as defined herein. In particular G8 is C(R8)$_2$, CH$_2$ or —(C=O)—, more particularly CH$_2$ or —(C=O)—; and G7 is C(R7)$_2$. In particular one of R5' and R5" is H and the other is N(R')$_2$.

In further alternative aspect of this subclass the invention relates to compounds having formula (Ie)

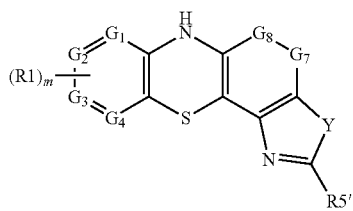

Ie wherein Y is S, NH or NR5"; R5' and R5" are each independently H or R5; and G1, G2, G3, G4, R1, m, G7, G8, and R5 are as defined herein. In particular G8 is C(R8)$_2$, CH$_2$ or —(C=O)—, more particularly CH$_2$ or —(C=O)—; and G7 is C(R7)$_2$. In particular R5' is H or N(R')$_2$. Further in particular R5" is H.

In a further aspect of this subclass G8 is —(C=O)— or CH$_2$; and G7 is C(R7)$_2$, in particular CMe$_2$. In an alternative aspect of this subclass G8 is [CH$_2$]$_n$, wherein n is 0, 1, or 2; and G7 is C(R7)$_2$, in particular G7 is CH$_2$. In yet a further alternative aspect of this subclass G7 is O or S; and G8 is CH$_2$.

In yet another alternative of this subclass of the invention, the invention relates to compounds of formula (Ig),

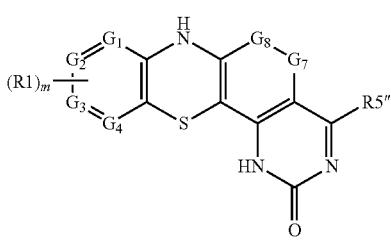

Ig

Wherein R5" is H or R5; and G1, G2, G3, G4, R1, m, G7, G8, and R5 are as defined in herein. In particular G8 is C(R8)$_2$, CH$_2$ or —(C=O)—, more particularly CH$_2$ or —(C=O)—; and G7 is C(R7)$_2$. In particular R5" is H.

In a further subclass of the invention, the invention relates to compounds of formula (I), wherein G2 and G3 are each C, and m is 0, 1, or 2; and which compounds have formula (If)

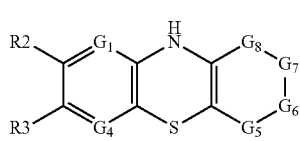

If wherein R2 and R3 are each independently H or R1; and G1, G2, G5, G6, G7, and G8 are each as defined herein, in particular in accordance with any subclass defined herein.

In an aspect of the invention each R1 is independently selected from a group consisting of halogen, C$_{1-3}$-alkoxy, C$_{1-3}$-(per)haloalkoxy, and di(C$_{1-3}$-alkyl)amino. In a further aspect of the invention each R5 is independently selected from a group consisting of halogen, C$_{1-3}$-alkoxy, C$_{1-3}$-(per)haloalkoxy, and di(C$_{1-3}$-alkyl)amino.

In a preferred aspect of the present invention compound of formula (I) is selected from the compounds of Table 1, in particular from a group consisting of:
7-chloro-8-methoxy-3,3-dimethyl-3,4-dihydro-2H-benzo[b]pyrido-[4,3-e][1,4]thiazin-1(5H)-one (1);
3,3-dimethyl-8-(trifluoromethoxy)-3,4-dihydro-2H-benzo[b]pyrido-[4,3-e][1,4]thiazin-1(5H)-one (2);
7-chloro-8-(dimethylamino)-3,3-dimethyl-3,4-dihydro-2H-benzo[b]-pyrido[4,3-e][1,4]thiazin-1(5H)-one (3);
8-methoxy-3,3-dimethyl-3,4-dihydro-2H-benzo[b]pyrido[4,3-e][1,4]-thiazin-1(5H)-one (4);
7-methoxy-1H,3H-benzo[b]pyrano[3,4-e][1,4]thiazin-4 (10H)-one (5);
7-(trifluoromethoxy)-1H,3H-benzo[b]pyrano[3,4-e][1,4]thiazin-4-(10H)-one (6);
7-(trifluoromethoxy)-1H,3H-benzo[b]thiopyrano[3,4-e][1,4]thiazin-4(10H)-one (7);
7-methoxy-1H,3H-benzo[b]thiopyrano[3,4-e][1,4]thiazin-4 (10H)-one (8);
9-methoxy-2,3,4,5-tetrahydrobenzo[5,6][1,4]thiazino[2,3-c]azepin-1(6H)-one (9);
9-(trifluoromethoxy)-2,3,4,5-tetrahydrobenzo[5,6][1,4]thiazino[2,3-c]-azepin-1(6H)-one (10);
3,3-dimethyl-8-(trifluoromethoxy)-2,3-dihydro-4H-benzo[b]pyrido-[4,3-e][1,4]thiazine-1,4(5H)-dione (11);
3,3-dimethyl-3,4-dihydro-2H-benzo[b]pyrido[4,3-e][1,4]thiazin-1(5H)-one (12);
3,3-diethyl-8-(trifluoromethoxy)-3,4-dihydro-2H-benzo[b]pyrido-[4,3-e][1,4]thiazin-1(5H)-one (13);
8-(trifluoromethoxy)-2H,4H-spiro[benzo[b]pyrido[4,3-e][1,4]thiazine-3,1'-cyclopentan]-1(5H)-one (14);
8-(trifluoromethoxy)-2',3',5',6'-tetrahydro-2H,4H-spiro[benzo[b]pyrido[4,3-e][1,4]thiazine-3,4'-pyran]-1(5H)-one (15);
2-ethyl-3,3-dimethyl-8-(trifluoromethoxy)-3,4-dihydro-2H-benzo[b]-pyrido[4,3-e][1,4]thiazin-1(5H)-one (16);
2-ethyl-8-(trifluoromethoxy)-2',3',5',6'-tetrahydro-2H,4H-spiro[benzo-[b]pyrido[4,3-e][1,4]thiazine-3,4'-pyran]-1 (5H)-one (17);
4,4-dimethyl-8-(trifluoromethoxy)-3,4-dihydro-2H-benzo[b]pyrido-[4,3-e][1,4]thiazin-1(5H)-one (18);
2-ethyl-4,4-dimethyl-8-(trifluoromethoxy)-3,4-dihydro-2H-benzo[b]-pyrido[4,3-e][1,4]thiazin-1(5H)-one (19);
4,4-dimethyl-9-(trifluoromethoxy)-2,6-dihydropyrazolo[4,3-c]phenolthiazin-5(4H)-one (20);

4,4-dimethyl-2,6-dihydropyrazolo[4,3-c]phenothiazin-5 (4H)-one (21);
8-chloro-4,4-dimethyl-2,6-dihydropyrazolo[4,3-c]phenothiazin-5(4H)-one (22);
5,5-dimethyl-10-(trifluoromethoxy)-5,7-dihydro-6H-pyrimido[5,4-c]-phenothiazine (23);
9-chloro-5,5-dimethyl-5,7-dihydro-6H-pyrimido[5,4-c]phenothiazin-6-one (24);
2-acetyl-4,4-dimethyl-9-(trifluoromethoxy)-2,6-dihydropyrazolo-[4,3-c]phenothiazin-5(4H)-one (25);
2-acetyl-4,4-dimethyl-2,6-dihydropyrazolo[4,3-c]phenothiazin-5(4H)-one (26);
2-acetyl-8-chloro-4,4-dimethyl-2,6-dihydropyrazolo[4,3-c] phenothiazin-5(4H)-one (27);
5,5-dimethyl-5,7-dihydro-6H-pyrimido[5,4-c]phenothiazin-6-one (28);
2,3,3-triethyl-8-(trifluoromethoxy)-3,4-dihydro-2H-benzo[b]pyrido-[4,3-e][1,4]thiazin-1(5H)-one (29);
4,4-dimethyl-8-(trifluoromethoxy)-3,4-dihydro-2H-benzo[b]pyrido-[4,3-e][1,4]thiazin-1(5H)-one 10-oxide (30).

In a further preferred aspect of the present invention the compound of formula (I) is selected from a group consisting of:
3,3-dimethyl-8-(trifluoromethoxy)-3,4-dihydro-2H-benzo[b]pyrido-[4,3-e][1,4]thiazin-1(5H)-one (2);
7-methoxy-1H,3H-benzo[b]thiopyrano[3,4-e][1,4]thiazin-4(10H)-one (8);
8-(trifluoromethoxy)-2',3',5',6'-tetrahydro-2H,4H-spiro [benzo[b]pyrido[4,3-e][1,4]thiazine-3,4'-pyran]-1(5H)-one (15);
2-ethyl-8-(trifluoromethoxy)-2',3',5',6'-tetrahydro-2H,4H-spiro[benzo-[b]pyrido[4,3-e][1,4]thiazine-3,4'-pyran]-1 (5H)-one (17);
2-acetyl-4,4-dimethyl-2,6-dihydropyrazolo[4,3-c]phenothiazin-5(4H)-one (26); and
5,5-dimethyl-5,7-dihydro-6H-pyrimido[5,4-c]phenothiazin-6-one (28).

In particular the present invention relates to compounds of formula (I), (I') (Ia), (Ib), (Ic), (Id), (Ie), (If) and/or (Ig), or metabolites, N-oxides, pharmaceutically acceptable salts, hydrates, or solvates thereof; preferably to said compounds; or N-oxides, pharmaceutically acceptable salts, hydrates, or solvates thereof; more preferably to said compounds or N-oxides, or pharmaceutically acceptable salts thereof; most preferably to said compounds or pharmaceutically acceptable salts thereof.

Compounds of formula (I) can be used as medicaments, in particular in the treatment or prevention of diseases or states, either acute or chronic, involving aberrant cellular lipid peroxidation in the central nervous system or in the periphery of the body.

Examples of diseases or states that may be treated with compounds of the present invention include, but are not limited to, Alzheimer's disease, dementia, tauopathies, frontotemporal dementia and parkinsonism linked to chromosome 17, progressive supranuclear palsy and corticobasal degeneration, amyotrophic lateral sclerosis, atherosclerosis, cancer, Huntington's disease, ischemic stroke, hemorrhagic stroke, ischemic bowel disease, limb ischemia, liver cirrhosis, non-alcoholic liver diseases, metabolic disorders, multiple sclerosis, myocardial ischemia, noise induced hearing loss, Parkinson's disease, retinal degeneration, renal diseases, traumatic brain or spinal cord injury, radiation associated normal tissue injury, liver transplantation induced stenosis, neonatal hypoxic-ischemic injury, adverse cerebral outcomes after cardiac bypass surgery, and HIV-associated neurocognitive disorders.

Compounds of the invention may be administered to a patient in need thereof in therapeutically effective amounts ranging usually from about 0.1 to 2000 mg per day depending on age, weight, sex, ethnic group, health of the patient, treated disease or disorder, administration route, the active ingredient used, kind of concurrent treatment, if any, frequency of treatment, and the nature of the effect desired. Compounds of the invention can be formulated into dosage forms using methods known in the art.

The term "effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

In an aspect of this invention there is provided a pharmaceutical composition comprising an effective amount of one or more compound(s) of formula (I) of the present invention together with pharmaceutically acceptable carrier, diluent, excipient, and/or other active ingredients. The pharmaceutical compositions can contain one or more of the compound(s) of the invention. The pharmaceutical compositions of the present invention can be administered to any animal that can experience the beneficial effects of the compounds of the invention. Foremost among such animals are mammals, including humans, although the invention is not intended to be so limited. Product comprising one or more compound(s) of the invention and one or more other active ingredient(s) may be used as combined preparation for simultaneous, separate, or sequential use in therapy.

The pharmaceutical compositions of the present invention can be administered by any means that achieve their intended purpose. Examples of such administrations include, but are not limited to, parenteral, subcutaneous, intravenous, intraarticular, intrathecal, intramuscular, intraperitoneal, by intradermal injections, via transdermal, rectal, buccal, oromucosal, nasal, ocular routes, via inhalation, and via implant. Alternatively, or concurrently, administration can be by the oral route.

In addition to the pharmacologically active compounds, the pharmaceutical compositions of compounds of the present invention can contain suitable pharmaceutically acceptable carriers comprising excipients and auxiliaries that facilitate processing of the active compounds into preparations that can be used pharmaceutically. The pharmaceutical compositions of the present invention are manufactured by means of conventional processes.

Furthermore, compounds of formula (I) can be used as synthesis intermediates for the preparation of other compounds, in particular of other pharmaceutically active ingredients, which are obtainable from the compounds of formula (I), for example by introduction of substituents or modification of functional groups.

The term "$C_{1-6}$-alkyl" or "$C_{1-3}$-alkyl" as used herein as such or as part of a substituent group, e.g. (per)haloalkyl, alkoxy, or hydroxyalkyl, relates to linear or branched saturated hydrocarbon group containing suitably 1 to 6 or 1 to 3, respectively, carbon atoms and thus $C_{1-2}$-alkyl includes methyl (Me) and ethyl (Et), n-propyl (n-Pr), isopropyl (iPr); and $C_{1-6}$-alkyl additionally includes n-butyl, sec-butyl, isobutyl, tert-butyl, and branched and straight chain pentyl and hexyl.

The term "$C_{1-6}$-alkylenyl" as used herein refers to a divalent group derived from a straight or branched chain hydrocarbon of having suitably 1 to 6 carbon atoms. Representative examples of alkylenyl groups include, but are not limited to, —CH$_2$—, —CH(CH$_3$)—, —C(CH$_3$)$_2$—, —CH$_2$CH$_2$—, and —CH$_2$CH$_2$CH$_2$—. As used herein, the term hydroxyalkyl (e.g. hydroxymethyl) is interchangeable with the term hydroxyalkylenyl.

The term "C$_{2-6}$-alkenyl" as used herein refers to an unsaturated linear or branched hydrocarbon groups having one or more olefinic double bond between any two carbon atoms and containing suitably 2 to 6 carbon atoms, such as ethenyl, propenyl, butenyl, pentenyl, and hexenyl. Preferred alkenyl groups of the present invention are linear alkenyl groups having a terminal double bond such as vinyl and allyl groups.

The term "C$_{2-6}$-alkynyl" as used herein refers to an unsaturated linear or branched hydrocarbon group having at least one olefinic triple bond between any two carbon atoms, such as ethynyl, propynyl, butynyl, pentynyl, and hexynyl. Examples of preferred alkynyl groups include, but are not limited to, linear alkynyls groups having a terminal triple bond.

The term "C$_{3-7}$-cycloalkyl" as used herein refers to cycloalkyl groups having 3 to 7 carbon atoms and thus includes cyclopropyl, cyclobutyl, cyclopentyl, cyclohexyl, and cycloheptyl.

The term "halogen" as used herein by itself or as part of other groups refers to elements from Group 17 IUPAC style of the periodic table and includes Cl, Br, F, and I. Preferred halogens are Cl and F.

The term "haloalkyl" as used herein refers to any of the above alkyl groups where one or more hydrogen atoms are replaced by halogen(s), preferably F or Cl. Examples of haloalkyl groups include without limitation chloromethyl and fluoromethyl. The term "perhaloalkyl" is understood to refer to an alkyl group, in which all the hydrogen atoms are replaced by halogen atoms. Preferred examples include trifluoromethyl (—CF$_3$) and trichloromethyl (—CCl$_3$).

The term "C$_{1-6}$-alkoxy" as used herein refers to a —O—(C$_{1-6}$-alkyl) group where the "C$_{1-6}$-alkyl" has the above-defined meaning. Examples of preferred alkoxy groups include methoxy, ethoxy, and n-propyloxy.

The term "di(C$_{1-6}$-alkyl)amino" used herein refers to a tertiary amine group, wherein the nitrogen atom is connected to two C$_{1-6}$-alkyl groups 5 where the "C$_{1-6}$-alkyl" has the above-defined meaning and which two alkyl groups may optionally be fused together to form together with the nitrogen atom they are attached to a 5 to 6 membered saturated heterocyclic ring which has the herein-defined meaning.

The term "5 to 6 membered unsaturated heterocyclic ring" as used herein refers to a unsaturated or aromatic ring with 5 to 6 ring atoms, of which 1 to 3 atoms are heteroatoms selected from a group consisting of N, O, and S. Examples of unsaturated heterocyclic rings include, but are not limited to, pyrrolyl, furanyl, thiophenyl (thienyl), imidazolyl, imidazonlinyl, pyrazolyl, dihydropyrazolyl, oxazolyl, isoxazolyl, dioxolanyl, thiazolyl, isothiazolyl, 1,2,4-triazol-1-yl, 1,2,3-triazolyl-1yl, tetrazolyl, and pyridinyl.

The term "5 to 7 membered ring" refers to any partially saturated, unsaturated or aromatic carbocyclic or heterocyclic ring which consists of ring carbon atoms in the case of heterocyclic ring, from 1 to 4, preferably 1 to 2 heteroatom(s) each independently selected from a group consisting of N, O, and S, wherein N when applicable represents NH or may be otherwise further substituted. Preferred saturated rings are 5 to 7 membered saturated carbocyclic or heterocyclic rings. Preferred unsaturated rings are 5 to 6 membered unsaturated carbocyclic or heterocyclic rings.

The term "3 to 7 membered saturated carbocyclic or heterocyclic ring" as used herein represents a stable 3 to 7 membered monocyclic ring which consists of ring carbon atoms and in the case of heterocyclic ring, from 1 to 4, preferably 1 to 2 heteroatom(s) each independently selected from a group consisting of N, O, and S, wherein N when applicable represents NH or may be otherwise further substituted.

The term "5 or 6 membered saturated heterocyclic ring" as used herein represents a stable 5 to 6 membered monocyclic ring and which consists of ring carbon atoms and from 1 to 4, preferably 1 to 2 in the case of saturated heterocyclic rings, heteroatom(s) each independently selected from a group consisting of N, O, and S, wherein N when applicable represents NH or may be otherwise further substituted. The heterocyclic ring may be further substituted at any carbon atom or nitrogen heteroatom suitable for substitution, wherein the substituent is preferably hydroxyl, thiol, benzyloxy, or an aforedefined alkyl, more preferably methyl. Examples of preferred saturated heterocyclic rings include, but are not limited to, pyrrolidinyl, piperidinyl, N-methyl piperidinyl, piperazinyl, N-methyl piperazinyl, and morpholinyl.

The term "optional" or "optionally" denotes that the subsequently described event or circumstance may but need not occur, and that the description includes instances where the event or circumstance occurs and instances in which it does not. The term "comprises" or "comprising" denotes that the subsequently described set may but need not include other elements.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The term "pharmaceutically acceptable salt" includes any non-toxic organic and inorganic acid or base addition salts that compounds of formula (I) can form. Illustrative inorganic acids, which form suitable salts, include, but are not limited to, hydrogen chloride, hydrogen bromide, sulphuric and phosphoric acids. Illustrative organic acids, which form suitable salts, include, but are not limited to, acetic acid, lactic acid, malonic acid, succinic acid, glutaric acid, fumaric acid, malic acid, tartaric acid, citric acid, ascorbic acid, maleic acid, benzoic acid, phenylacetic acid, cinnamic acid, methane sulfonic acid, salicylic acid, and the like. The term also comprises solvates which the compounds and salts thereof are able to form, such as, for example, hydrates, alcoholates, and the like. These salts also include salts useful for the chiral resolution of racemates. Suitable base salts include, but are not limited to, those derived from inorganic bases such as aluminum, ammonium, calcium, copper, iron, lithium, magnesium, manganese, potassium, sodium, and zinc salts.

The term "N-oxide" refers to a compound that is oxidized at any suitable nitrogen atom. The term also includes hydroxamic acid derivates of the compounds of the present invention. Thus the oxygen atom may for example suitably reside either at the thiazine nitrogen atom or at the nitrogen atom of G6 or G7 or both.

Some of the compounds disclosed herein may contain one or more asymmetric centers and may thus give rise to enantiomers, diastereomers, and other stereoisomeric forms. The present invention is also meant to encompass racemic and/or stereoisomeric mixtures, resolved forms, and mixtures thereof in all proportions, as well as the individual enantiomers and/or diastereomers that may be separated according to methods that are known to those skilled in the art. The present invention is further meant to include any eventual metabolite, prodrug, and tautomeric forms of the compounds of the present invention.

When any variable occurs more than one time in any constituent or in formula (I), its definition on each occurrence is independent of its definition at every other occurrence. Further, combinations of substituents and/or variables are permissible only if such combination results a stable compound.

EXAMPLES OF THE INVENTION

Illustrative, but not limiting examples of compounds of the present invention are those presented in the following Table 1.

TABLE 1

| # | | NMR/MS |
|---|---|---|
| 1 | 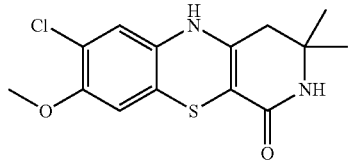<br>7-chloro-8-methoxy-3,3-dimethyl-3,4-dihydro-2H-benzo[b]pyrido[4,3-e][1,4]thiazin-1(5H)-one | 1H NMR (DMSO-d6): 1.17 (6H, s), 2.15 (2H, s), 3.71 (3H, s), 6.50 (1H, s), 6.55 (1H, s), 7.10 (1H, s), 8.17 (1H, s). m/z 309 (M − 1) |
| 2 | 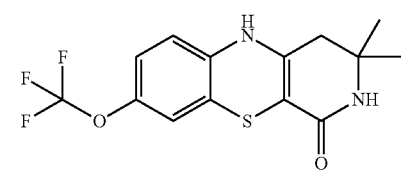 [SMILES: CC1(C)CC2=C(Sc3cc(OC(F)(F)F)ccc3N2)C(=O)N1]<br>3,3-dimethyl-8-(trifluoromethoxy)-3,4-dihydro-2H-benzo[b]pyrido[4,3-e][1,4]thiazin-1(5H)-one | 1H NMR (DMSO-d6): 1.17 (6H, s), 2.16 (2H, s), 6.47 (1H, m), 6.74 (1H, m), 6.82 (1H, m), 7.17 (1H, s), 8.40 (1H, s). m/z 331 (M + 1) |
| 3 | 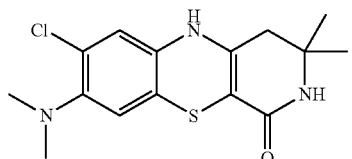<br>7-chloro-8-(dimethylamino)-3,3-dimethyl-3,4-dihydro-2H-benzo[b]pyrido[4,3-e][1,4]thiazin-1(5H)-one | 1H NMR (DMSO-d6): 1.17 (6H, s), 2.15 (2H, s), 2.57 (6H, s), 6.47 (1H, s), 6.50 (1H, s), 7.11 (1H, s), 8.21 (1H, s). m/z 324 (M + 1) |
| 4 | 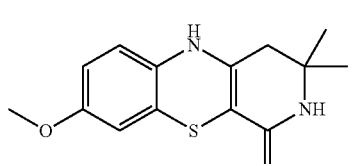<br>8-methoxy-3,3-dimethyl-3,4-dihydro-2H-benzo[b]pyrido[4,3-e][1,4]thiazin-1(5H)-one | 1H NMR (DMSO-d6): 1.16 (6H, s), 2.15 (2H, s), 3.61 (3H, s), 6.30 (1H, m), 6.39 (2H, m), 7.01 (1H, s), 8.13 (1H, s). m/z 277 (M + 1) |
| 5 | 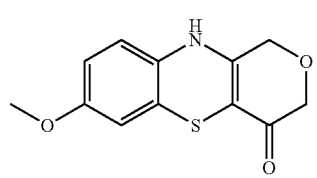 [SMILES: COc1ccc2c(c1)SC1=C(COCC1=O)N2]<br>7-methoxy-1H,3H-benzo[b]pyrano[3,4-e][1,4]-thiazin-4(10H)-one | 1H NMR (MeOH-d4): 3.69 (3H, s), 4.09 (2H, s), 4.26 (2H, s), 6.39 (1H, m), 6.47 (2H, m). m/z 250 (M + 1) |

TABLE 1-continued

| # | | NMR/MS |
|---|---|---|
| 6 | 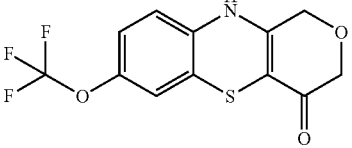 7-(trifluoromethoxy)-1H,3H-benzo[b]pyrano[3,4-e][1,4]thiazin-4(10H)-one | 1H NMR (MeOH-d4): 4.10 (2H, s), 4.26 (2H, s), 6.56 (1H, m), 6.72 (1H, m), 6.81 (1H, m). m/z 304 (M + 1) |
| 7 | 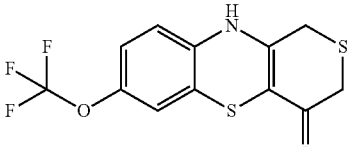 7-(trifluoromethoxy)-1H,3H-benzo[b]thiopyrano[3,4-e][1,4]thiazin-4(10H)-one | 1H NMR (MeOH-d4): 3.32 (2H, s), 3.43 (2H, s), 6.57 (1H, m), 6.71 (1H, m), 6.79 (1H, m). m/z 318 (M − 1) |
| 8 | 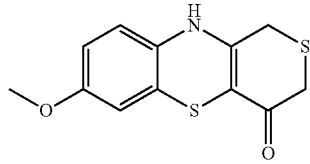 [SMILES: COc1ccc2c(c1)SC1=C(CSCC1=O)N2] 7-methoxy-1H,3H-benzo[b]thiopyrano-[3,4-e][1,4]thiazin-4(10H)-one | 1H NMR (DMSO-d6): 3.29 (2H, s), 3.45 (2H, s), 3.64 (3H,s), 6.42 (1H, m), 6.48 (1H, m), 6.55 (1H, m), 9.21 (1H, s). m/z 266 (M + 1) |
| 9 | 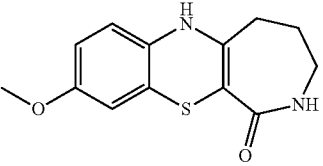 [SMILES: COc1ccc2c(c1)SC1=C(CCCNC1=O)N2] 9-methoxy-2(3,4,5-tetrahydrobenzo[5,6]-[1,4]thiazino[2,3-c]azepin-1(6H)-one | 1H NMR (DMSO-d6): 1.80 (2H, m), 2.31 (2H, m), 3.04 (2H, m), 3.62 (3H, s), 6.36 (1H, m), 6.46 (2H, m), 7.44 (1H, s), 8.18 (1H, s). m/z 263 (M + 1) |
| 10 | 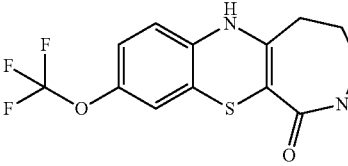 9-(trifluoromethoxy)-2,3,4,5-tetrahydrobenzo[5,6]-[1,4]thiazino[2,3-c]azepin-1(6H)-one | 1H NMR (MeOH-d4): 1.94 (2H, m), 2.42 (2H, m), 3.23 (2H, m), 6.54 (1H, m), 6.68 (1H, m), 6.79 (1H, m). m/z 317 (M + 1) |
| 11 | 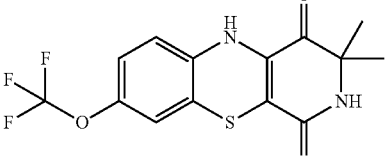 3,3-dimethyl-8-(trifluoromethoxy)-2,3-dihydro-4H-benzo[b]pyrido[4,3-e][1,4]thiazine-1,4(5H)-dione | 1H NMR (DMSO-d6): 1.48 (6H, s), 7.03 (3H, m), 8.19 (1H, s), 9.49 (1H, s). m/z 345 (M + 1) |

TABLE 1-continued

| # | Structure | NMR/MS |
|---|---|---|
| 12 | 3,3-dimethyl-3,4-dihydro-2H-benzo[b]pyrido-[4,3-e][1,4]thiazin-1(5H)-one | 1H NMR (DMSO-d6): 1.17 (6H, s), 2.16 (2H, s), 6.42 (1H, m), 6.67 (2H, m), 6.82 (1H, m), 7.09 (1H, s), 8.23 (1H, s). m/z 247 (M + 1) |
| 13 | 3,3-diethyl-8-(trifluoromethoxy)-3,4-dihydro-2H-benzo[b]pyrido[4,3-e][1,4]thiazin-1(5H)-one | 1H NMR (DMSO-d6): 0.78 (6H, t, J = 7.52 Hz), 1.39 (2H, m), 1.51 (2H, m), 2.14 (2H, s), 6.46 (1H, m), 6.74 (1H, m), 6.82 (1H, m), 7.16 (1H, s), 8.40 (1H, s). m/z 359 (M + 1) |
| 14 | 8-(trifluoromethoxy)-2H,4H-spiro[benzo[b]-pyrido[4,3-e][1,4]thiazine-3,1'-cyclopentan]-1(5H)-one | 1H NMR (DMSO-d6): 1.52 (2H, m), 1.62 (4H, m), 1.68 (2H, m), 2.24 (2H, s), 6.46 (1H, m), 6.74 (1H, m), 6.82 (1H, m), 7.37 (1H, s), 8.42 (1H, s). m/z 355 (M − 1) |
| 15 | 8-(trifluoromethoxy)-2',3',5',6'-tetrahydro-2H,4H-spiro[benzo[b]pyrido[4,3-e][1,4]thiazine-3,4'-pyran]-1(5H)-one | 1H NMR (DMSO-d6): 1.62 (4H, m), 2.33 (2H, s), 3.44 (2H, m), 3.71 (2H, m), 6.47 (1H, m), 6.75 (1H, m), 6.83 (1H, m), 7.44 (1H, s), 8.47 (1H, s), m/z 373 (M + 1) |
| 16 | 2-ethyl-3,3-dimethyl-8-(trifluoromethoxy)-3,4-dihydro-2H-benzo[b]pyrido[4,3-e][1,4]thiazin-1(5H)-one | 1H NMR (DMSO-d6): 1.01 (3H, t. J = 6.96 Hz), 1.25 (6H, s), 2.22 (2H, s), 3.24 (2H, q, J = 6.96 Hz), 6.46 (1H, m), 6.74 (1H, m), 6.81 (1H, m), 8.38 (1H. s). m/z 357 (M − 1) |
| 17 | 2-ethyl-8-(trifluoromethoxy)-2',3',5'6'-tetrahydro-2H,4H-spiro[benzo[b]pyrido[4,3-e][1,4]thiazine-3,4'-pyran]-1(5H)-one | 1H NMR (DMSO-d6): 0.99 (3H, t, J = 7.00 Hz), 1.66 (2H, m), 1.89 (2H, m), 2.57 (2H, s), 3.31 (2H, q, J = 7.00 Hz), 3.38 (2H, m), 3.81 (2H, m), 6.44 (1H, m), 6.75 (1H, m), 6.82 (1H, m), 8.41 (1H, s). m/z 399 (M − 1) |

TABLE 1-continued

| # | | NMR/MS |
|---|---|---|
| 18 | 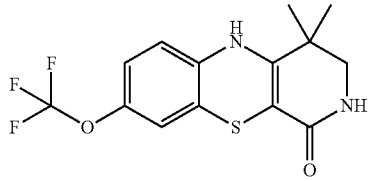 [SMILES: CC1(C)CNC(=O)C2=C1Nc1ccc(OC(F)(F)F)cc1S2]<br>4,4-dimethyl-8-(trifluoromethoxy)-3,4-dihydro-2H-benzo[b]pyrido[4,3-e][1,4]thiazin-1(5H)-one | 1H NMR (DMSO-d6): 1.12 (6H, s), 2.92 (2H, m), 6.77 (1H, m), 6.82 (1H, m), 6.87 (1H, m), 7.32 (1H, m), 7.76 (1H, s). m/z 331 (M + 1) |
| 19 | 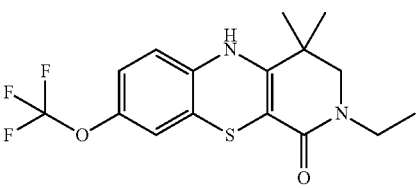 [SMILES: CCN1CC(C)(C)C2=C(Sc3cc(OC(F)(F)F)ccc3N2)C1=O]<br>2-ethyl-4,4-dimethyl-8-(trifluoromethoxy)-3,4-dihydro-2H-benzo[b]pyrido[4,3-e][1,4]thiazin-1(5H)-one | 1H NMR (DMSO-d6): 0.99 (3H, t, J = 7.12 Hz), 1.13 (6H, s), 3.06 (2H, s), 3.28 (2H, q, J = 7.12 Hz), 6.76 (1H, m), 6.80 (1H, m), 6.85 (1H, m), 7.75 (1H, s). m/z 359 (M + 1) |
| 20 | 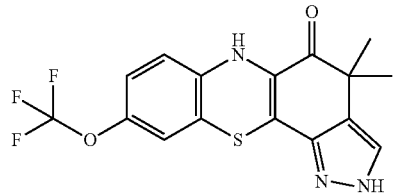 [SMILES: CC1(C)C(=O)C2=C(Sc3cc(OC(F)(F)F)ccc3N2)c2n[nH]cc21]<br>4,4-dimethyl-9-(trifluoromethoxy)-2,6-dihydro-pyrazolo[4,3-c]phenothiazin-5(4H)-one | 1H NMR (CDCl3): 1.55 (6H, s), 6.58 (1H, m), 6.68 (1H, bs), 6.83 (1H, m), 6.87 (1H, m), 7.68 (1H, s), 10.70 (1H, bs). m/z 366 (M − 1) |
| 21 | 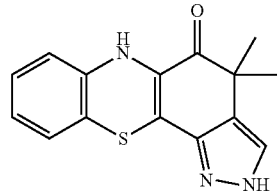 [SMILES: CC1(C)C(=O)C2=C(Sc3ccccc3N2)c2n[nH]cc21]<br>4,4-dimethyl-2,6-dihydropyrazolo[4,3-c]phenol-thiazin-5(4H)-one | 1H NMR (CDCl3): 1.54 (6H, s), 6.61 (1H, m), 6.65 (1H, bs), 6.83 (1H, m), 6.95 (1H, m), 7.01 (1H, m), 7.68 (1H, s). m/z 284 (M + 1) |
| 22 | 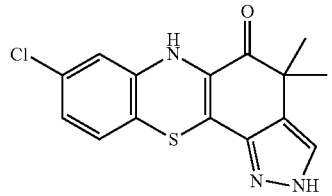 [SMILES: CC1(C)C(=O)C2=C(Sc3ccc(Cl)cc3N2)c2n[nH]cc21]<br>8-chloro-4,4-dimethyl-2,6-dihydropyrazolo-[4,3-c]phenothiazin-5(4H)-one | 1H NMR (CDCl3): 1.53 (6H, s), 6.61 (1H, m), 6.66 (1H, bs), 6.79 (1H, m), 6.84 (1H, m), 7.68 (1H, s), 10.87 (1H, bs). m/z 316 (M − 1) |
| 23 | 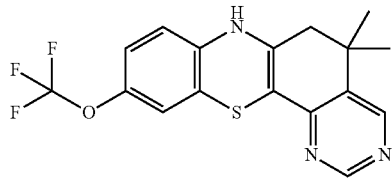 [SMILES: CC1(C)CC2=C(Sc3cc(OC(F)(F)F)ccc3N2)c2ncncc21]<br>5,5-dimethyl-10-(trifluoromethoxy)-5,7-dihydro-6H-pyrimido[5,4-c]phenothiazine | 1H NMR (CDCl3): 1.36 (6H, s), 2.26 (2H, s), 6.31 (1H, m), 6.73 (1H, m), 6.76 (1H, m), 8.33 (1H, s), 8.88 (1H, s). m/z 364 (M − 1) |

TABLE 1-continued

| # | | NMR/MS |
|---|---|---|
| 24 | 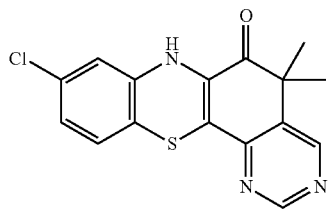 [SMILES: CC1(C)C(=O)C2=C(Sc3ccc(Cl)cc3N2)c2ncncc21]<br>9-chloro-5,5-dimethyl-5,7-dihydro-6H-pyrimido[5,4-c]phenothiazin-6-one | 1H NMR (CDCl3): 1.66 (6H, s), 6.64 (1H, m), 6.78 (1H, bs), 6.82 (2H, m), 9.12 (1H, s), 9.38 (1H, s). m/z 330 (M + 1) |
| 25 | 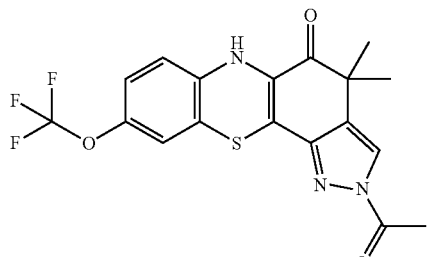<br>2-acetyl-4,4-dimethyl-9-(trifluoromethoxy)-2,6-dihydropyrazolo[4,3-c]phenothiazin-5(4H)-one | m/z 408 (M − 1) |
| 26 | 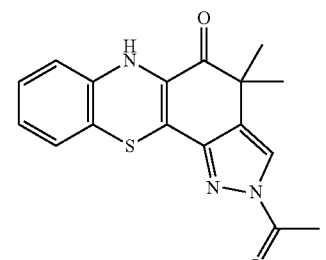<br>2-acetyl-4,4-dimethyl-2,6-dihydro-pyrazolo-[4,3-c]phenothiazin-5(4H)-one | 1H NMR (DMSO-d6): 1.53 (6H, s), 2.73 (3H, s), 6.80 (1H, m), 6.96 (1H, m), 7.00 (1H, m), 7.07 (1H, m), 8.01 (1H, s), 8.86 (1H, s). m/z 326 (M + 1) |
| 27 | 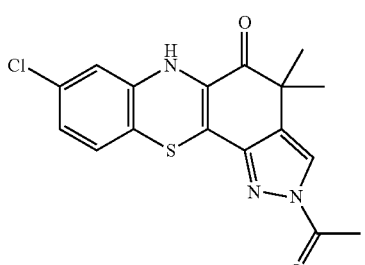<br>2-acetyl-8-chloro-4,4-dimethyl-2,6-dihydro-pyrazolo[4,3-c]phenothiazin-5(4H)-one | 1H NMR (DMSO-d6): 1.52 (6H, s), 2.72 (3H, s), 6.82 (1H, m), 6.96 (1H, m), 7.18 (1H, m), 8.28 (1H, s), 8.87 (1H, s). m/z 318 (M + 1) |
| 28 | 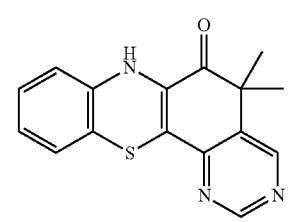 [SMILES: CC1(C)C(=O)C2=C(Sc3ccccc3N2)c2ncncc21]<br>5,5-dimethyl-5,7-dihydro-6H-pyrimido[5,4-c]phenothiazin-6-one | 1H NMR (CDCl3): 1.67 (6H, s), 6.63 (1H, m), 6.77 (1H, bs), 6.84 (1H, m), 6.93 (1H, m), 7.03 (1H, m), 9.12 (1H, s), 9.38 (1H, s). m/z 296 (M + 1) |

TABLE 1-continued

| # | | NMR/MS |
|---|---|---|
| 29 | 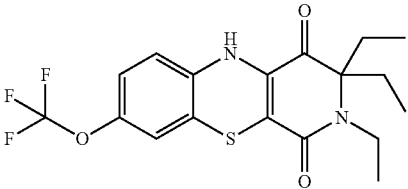<br>2,3,3-triethyl-8-(trifluoromethoxy)-3,4-dihydro-2H-benzo[b]pyrido[4,3-e][1,4]thiazin-1(5H)-one | 1H NMR (DMSO-d6): 0.83 (6H, t, J = 7.44 Hz), 1.04 (3H, t, J = 6.92 Hz), 1.61 (4H, m), 2.22 (2H, s), 3.20 (2H, q, J = 6.92 Hz), 6.45 (1H, m), 6.74 (1H, m), 6.81 (1H, m), 8.36 (1H, s). m/z 385 (M − 1) |
| 30 | 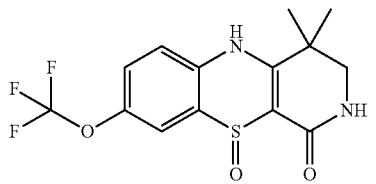 [SMILES: CC1(C)CNC(=O)C2=C1Nc1ccc(OC(F)(F)F)cc1S2=O]<br>4,4-dimethyl-8-(trifluoromethoxy)-3,4-dihydro-2H-benzo[b]pyrido[4,3-e][1,4]thiazin-1(5H)-one 10-oxide | 1H NMR (CDCl3): 1.37 (3H, s), 1.41 (3H, s), 3.21 (1H, m), 3.33 (1H, m), 6.16 (1H, bs), 7.17 (1H, m), 7.27 (1H, m), 7.59 (1H, m), 8.08 (1H, m). m/z 347 (M + 1) |
| 31 | 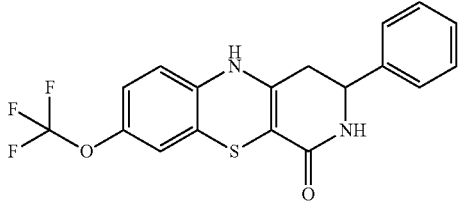 [SMILES: O=C1NC(c2ccccc2)CC2=C1Sc1cc(OC(F)(F)F)ccc1N2]<br>3-phenyl-8-(trifluoromethoxy)-3,4-dihydro-2H-benzo[b]pyrido[4,3-e][1,4]thiazin-1(5H)-one | 1H NMR (d6-DMSO): 2.38 (1H, m), 2.59 (1H, m), 4.60 (1H, m), 6.43 (1H, m), 6.76 (1H, m), 6.81 (1H, m), 7.25-7.40 (5H, m), 7.59 (1H, s), 8.45 (1H, s). m/z 379 (M + 1) |
| 32 | 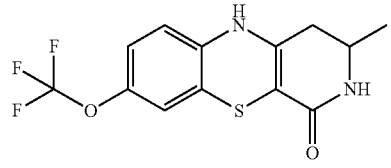 [SMILES: CC1CC2=C(Sc3cc(OC(F)(F)F)ccc3N2)C(=O)N1]<br>3-methyl-8-trifluoromethoxy)-3,4-dihydro-2H-benzo[b]pyrido[4,3-e][1,4]thiazin-1(5H)-one | 1H NMR (d6-DMSO): 1.10 (3H, d, J = 6,4 Hz), 2.05 (1H, m), 2.20 (1H, m), 3.49 (1H, m), 6.48 (1H, m), 6.74 (1H, m), 6.82 (1H, m), 7.17 (1H, s), 8.45 (1H, s). m/z 317 (M + 1) |
| 33 | 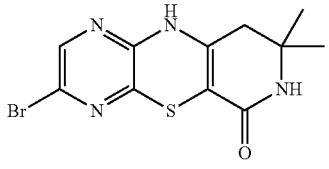 [SMILES: CC1(C)CC2=C(Sc3nc(Br)cnc3N2)C(=O)N1]<br>3-bromo-8,8-dimethyl-8,9dihydro-7H-pyrazino-[2,3-b]pyrido[4,3-e][1,4]thiazin-6(10H)-one | 1H NMR (d6-DMSO): 1.17 (6H, s), 2.17 (2H, s), 7.47 (1H, s), 7.63 (1H, s), 9.29 (1H, s). m/z 327 (M + 1) |
| 34 | 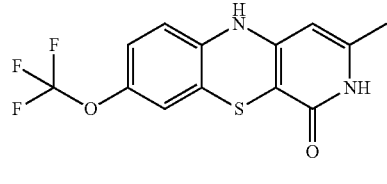 [SMILES: Cc1cc2c(c(=O)[nH]1)Sc1cc(OC(F)(F)F)ccc1N2]<br>3-methyl-8-(trifluoromethoxy)-2H-benzo[b]-pyrido[4,3-e][1,4]thiazin-1(5H)-one | 1H NMR (d6-DMSO): 2.02 (3H, s), 5.40 (1H, s), 6.51 (1H, m), 6.83 (1H, m), 6.85 (1H, m), 8.71 (1H, s), 11.17 (1H, s). m/z 313 (M − 1) |

TABLE 1-continued

| # | | NMR/MS |
|---|---|---|
| 35 | 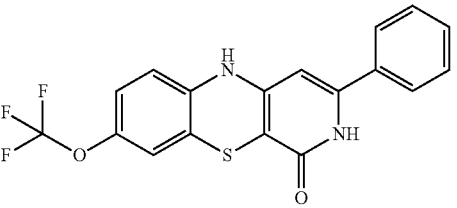 [SMILES: O=c1[nH]c(-c2ccccc2)cc2c1Sc1cc(OC(F)(F)F)ccc1N2]<br>3-phenyl-8-(trifluoromethoxy)-2H-benzo[b]-pyrido[4,3-e][1,4]thiazin-1(5H)-one | 1H NMR (d4-MeOH): 5.97 (1H, s), 6.51 (1H, m), 6.73 (1H, m), 6.80 (1H, m), 7.49 (3H, m), 7.58 (2H, m). m/z 377 (M + 1) |
| 36 | 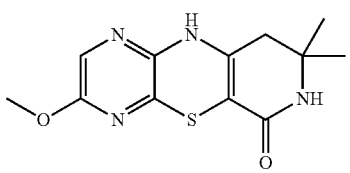<br>3-methoxy-8,8-dimethyl-8,9-dihydro-7H-pyrazino-[2,3-b]-pyrido[4,3-e][1,4]thiazin-6(10H)-one | 1H NMR (d6-DMSO): 1.17 (6H, s), 2.17 (2H, s), 3.71 (3H, s), 7.26 (1H, s), 7.29 (1H, s), 8.85 (1H, s). m/z 279 (M + 1) |
| 37 | 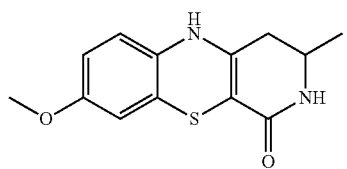<br>8-methoxy-3-methyl-3,4-dihydro-2H-benzo[b]-pyrido[4,3-e][1,4]thiazin-1(5H)-one | 1H NMR (d6-DMSO): 1.10 (3H, d, J = 6,3 Hz), 2.03 (1H, m), 2.19 (1H, m), 3.46 (1H, m), 3.62 (3H, s), 6.31 (1H, m), 6.39 (1H, m), 6.41 (1H, m), 7.01 (1H, s), 8.17 (1H, s). m/z 263 (M + 1) |
| 38 | 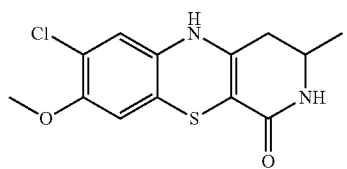<br>7-chloro-8-methoxy-3-methyl-3,4-dihydro-2H-benzo[b]pyrido[4,3-e][1,4]thiazin-1(5H)-one | 1H NMR (d6-DMSO): 1.10 (3H, d, J = 6,3 Hz), 2.04 (1H, m), 2.18 (1H, m), 3.49 (1H, m), 3.71 (3H, s), 6.50 (1H, s), 6.55 (1H, s), 7.10 (1H, s), 8.22 (1H, s). m/z 295 (M − 1) |
| 39 | 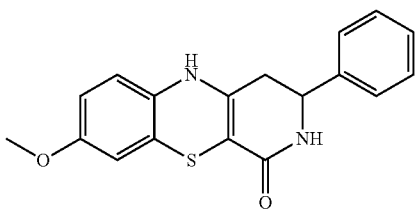 [SMILES: COc1ccc2c(c1)SC1=C(CC(c3ccccc3)NC1=O)N2]<br>8-methoxy-3-phenyl-3,4-dihydro-2H-benzo[b]-pyrido[4,3-e][1,4]thiazin-1(5H)-one | 1H NMR (d6-DMSO): 2.39 (1H, m), 2.58 (1H, m), 3.61 (3H, s), 4.57 (1H, m), 6.31 (1H, m), 6.34 (1H, m), 6.40 (1H, m), 7.25-7.40 (5H, m), 7.43 (1H, s), 8.17 (1H, s). m/z 325 (M + 1) |
| 40 | 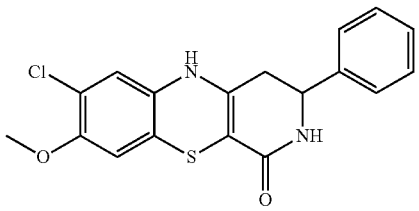 [SMILES: COc1cc2c(cc1Cl)NC1=C(S2)C(=O)NC(c2ccccc2)C1]<br>7-chloro-8-methoxy-3-phenyl-3,4-dihydro-2H-benzo[b]pyrido[4,3-e][1,4]thiazin-1(5H)-one | 1H NMR (d6-DMSO): 2.36 (1H, m), 2.58 (1H, m), 3.71 (3H, s), 4.60 (1H, m), 6.45 (1H, s), 6.56 (1H, s), 7.25-7.40 (5H, m), 7.52 (1H, s), 8.22 (1H, s). m/z 359 (M + 1) |

TABLE 1-continued

| # | | NMR/MS |
|---|---|---|
| 41 | 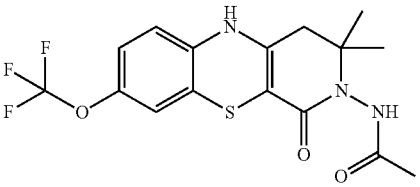 [SMILES: CC(=O)NN1C(=O)C2=C(CC1(C)C)Nc1ccc(OC(F)(F)F)cc1S2]<br>N-(3,3-dimethyl-1-oxo-8-(trifluoromethoxy)-1,3,4,5-tetrahydro-2H-benzo[b]pyrido[4,3-e][1,4]thiazin-2-yl)acetamide | 1H NMR (DMSO-d6): 1.17 (6H, s), 1.86 (3H, s), 2.23 (1H, m), 2.51 (1H, m), 6.51 (1H, m), 6.80 (1H, m), 6.84 (1H, m), 8.61 (1H, s), 9.47 (1H, s). m/z 386 (M − 1) |
| 42 | 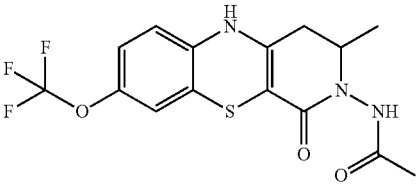 [SMILES: CC(=O)NN1C(=O)C2=C(CC1C)Nc1ccc(OC(F)(F)F)cc1S2]<br>N-(3-methyl-1-oxo-8-(trifluoromethoxy)-1,3,4,5-tetrahydro-2H-benzo[b]pyrido[4,3-e][1,4]thiazin-2-yl)acetamide | 1H NMR (d6-DMSO): 1.11 (3H, d, J = 6.4 Hz), 1.84 (3H, s), 2.24 (1H, m), 2.52 (1H, m), 378 (1H, m), 6.52 (1H, m), 6.80 (1H, m), 6.85 (1H, m), 8.68 (1H, s), 9.78 (1H, s). m/z 372 (M − 1) |
| 43 | 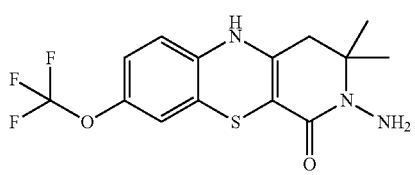 [SMILES: CC1(C)CC2=C(Sc3cc(OC(F)(F)F)ccc3N2)C(=O)N1N]<br>2-amino-3,3-dimethyl-8-(trifluoromethoxy)-3,4-dihydro-2H-benzo[b]pyrido[4,3-e][1,4]thiazin-1(5H)-one | 1H NMR (DMSO-d6): 1.20 (6H, s), 2.29 (2H, s), 4.39 (2H, s), 6.48 (1H, m), 6.77 (1H, m), 6.83 (1H, m), 8.46 (1H, s) m/z 346 (M + 1) |
| 44 | 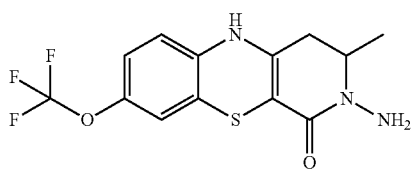 [SMILES: CC1CC2=C(Sc3cc(OC(F)(F)F)ccc3N2)C(=O)N1N]<br>2-amino-3-methyl-8-(trifluoromethoxy)-3,4-dihydro-2H-benzo[b]pyrido[4,3-e][1,4]thiazin-1(5H)-one | 1H NMR (d6-DMSO): 1.15 (3H, d, J = 6.4 Hz), 2.09 (1H, m), 2.59 (1H, m), 3.56 (1H, m), 4.57 (2H, s), 6.48 (1H, m), 6.77 (1H, m), 6.83 (1H, m), 8.48 (1H, s). m/z 332 (M + 1) |
| 45 | 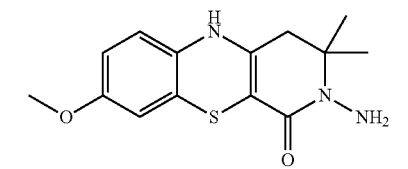<br>2-amino-8-methoxy-3,3-dimethyl-3,4-dihydro-2H-benzo[b]pyrido[4,3-e][1,4]thiazin-1(5H)-one | 1H NMR (DMSO-d6): 1.19 (6H, s), 2.28 (2H, s), 3.62 (3H, s), 4.35 (2H, s), 6.32 (1H, m), 6.39 (1H, m), 6.42 (1H, m), 8.18 (1H, s) m/z 292 (M + 1) |
| 46 | 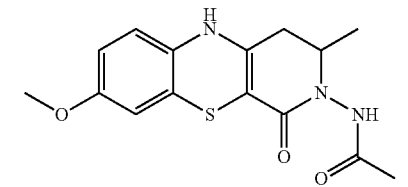 [SMILES: COc1ccc2c(c1)SC1=C(CC(C)N(NC(C)=O)C1=O)N2]<br>N-(8-methoxy-3-methyl-1-oxo-1,3,4,5-tetrahydro-2H-benzo[b]pyrido[4,3-e][1,4]thiazin-2-yl)acetamide | 1H NMR (d6-DMSO): 1.10 (3H, d, J = 6.4 Hz), 1.83 (3H, s), 2.23 (1H, m), 2.46 (1H, m), 3.62 (3H, s), 3.77 (1H, m), 6.36 (1H, m), 6.43 (2H, m), 8.42 (1H, s), 9.72 (1H, s). m/z 320 (M + 1) |

TABLE 1-continued

| # | Structure | NMR/MS |
|---|---|---|
| 47 | 2-amino-8-methoxy-3-methyl-3,4-dihydro-2H-benzo[b]pyrido[4,3-e][1,4]thiazin-1(5H)-one | 1H NMR (d6-DMSO): 1.14 (3H, d, J = 6.4 Hz), 2.08 (1H, m), 2.57 (1H, m), 3.53 (1H, m), 3.62 (3H, s), 4.53 (2H, s), 6.32 (1H, m), 6.39 (1H, m), 6.42 (1H, m), 8.21 (1H, s). m/z 278 (M + 1) |
| 48 | N-(7-chloro-8-methoxy-3,3-dimethyl-1-oxo-1,3,4,5-tetrahydro-2H-benzo[b]pyrido[4,3-e][1,4]thiazin-2-yl)acetamide | 1H NMR (DMSO-d6): 1.17 (6H, s), 1.85 (3H, s), 2.20 (1H, m), 2.54 (1H, m), 3.72 (3H, s), 6.53 (1H, s), 6.60 (1H, s), 8.40 (1H, s), 9.44(1H, s). m/z 366 (M − 1) |
| 49 | 2-amino-7-chloro-8-methoxy-3,3-dimethyl-3,4-dihydro-2H-benzo[b]pyrido[4,3-e][1,4]thiazin-1(5H)-one | 1H NMR (DMSO-d6): 1.19 (6H, s), 2.28 (2H, s), 3.71 (3H, s), 4.37 (2H, s), 6.50 (1H, s), 6.57 (1H, s), 8.23 (1H, s). m/z 326 (M − 1) |
| 50 | N-(7-chloro-8-methoxy-3-methyl-1-oxo-1,3,4,5-tetrahydro-2H-benzo[b]pyrido[4,3-e][1,4]thiazin-2-yl)acetamide | 1H NMR (d6-DMSO): 1.10 (3H, d, J = 6.3 Hz), 1.83 (3H, s), 2.23 (1H, m), 2.45 (1H, m), 3.72 (3H, s), 3.77 (1H, m), 6.53 (1H, s), 6.61 (1H, s), 8.46 (1H, s), 9.75 (1H, s). m/z 354 (M + 1) |
| 51 | 2-amino-7-chloro-8-methoxy-3-methyl-3,4-dihydro-2H-benzo[b]pyrido[4,3-e][1,4]thiazin-1(5H)-one | 1H NMR (d6-DMSO): 1.15 (3H, d, J = 6,4 Hz), 2.07 (1H, m), 2.58 (1H, m), 3.55 (1H, m), 3.71 (3H, s), 4.56 (2H, s), 6.50 (1H, s), 6.57 (1H, s), 8.26 (1H, s). m/z 312 (M + 1) |
| 52 | N-(8-methoxy-3,3-dimethyl-1-oxo-1,3,4,5-tetrahydro-2H-benzo[b]pyrido[4,3-e][1,4]thiazin-2-yl)acetamide | 1H NMR (DMSO-d6): 1.16 (6H, s), 1.85 (3H, s), 2.21 (1H, m), 2.51 (1H, m), 3.62 (3H, s), 6.35 (1H, m), 6.42 (2H, m), 8.36 (1H, s), 9.42 (1H, s). m/z 334 (M + 1) |

TABLE 1-continued

| # | | NMR/MS |
|---|---|---|
| 53 | 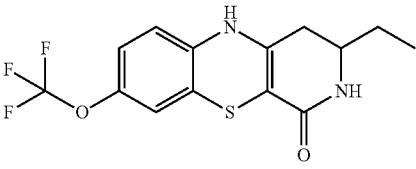 [SMILES: CCC1CC2=C(Sc3cc(OC(F)(F)F)ccc3N2)C(=O)N1]<br>3-ethyl-8-(trifluoromethoxy)-3,4-dihydro-2H-benzo[b]pyrido[4,3-e][1,4]thiazin-1(5H)-one | 1H NMR (d6-DMSO): 0.85 (3H, t, J = 7.5 Hz), 1.35-1.60 (2H, m), 2.08 (1H, m), 2.24 (1H, m), 3.28 (1H, m), 6.48 (1H, m), 6.75 (1H, m), 6.82 (1H, m), 7.18 (1H, s), 8.46 (1H, s). m/z 331 (M + 1) |
| 54 | 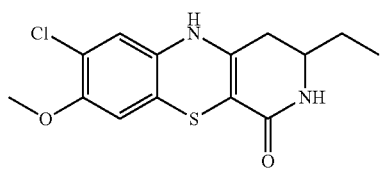 [SMILES: CCC1CC2=C(Sc3cc(OC)c(Cl)cc3N2)C(=O)N1]<br>7-chloro-3-ethyl-8-methoxy-3,4-dihydro-2H-benzo[b]pyrido[4,3-e][1,4]thiazin-1(5H)-one | 1H NMR (d6-DMSO): 0.85 (3H, t, J = 7.5 Hz), 1.35-1.60 (2H, m), 2.08 (1H, m), 2.22 (1H, m), 2.55 (1H, m), 3.71 (3H, s), 6.49 (1H, s), 6.55 (1H, s), 7.11 (1H, s), 8.23 (1H, s). m/z 311 (M + 1) |
| 55 | 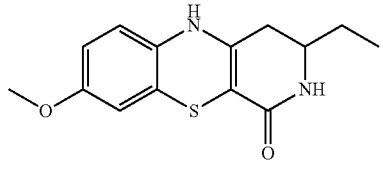 [SMILES: CCC1CC2=C(Sc3cc(OC)ccc3N2)C(=O)N1]<br>3-ethyl-8-methoxy-3,4-dihydro-2H-benzo[b]-pyrido[4,3-e][1,4]thiazin-1(5H)-one | 1H NMR (d6-DMSO): 0.85 (3H, t, J = 7.5 Hz), 1.35-1.60 (2H, m), 2.08 (1H, m), 2.22 (1H, m), 2.43 (1H, m), 3.62 (3H, s), 6.31 (1H, m), 6.40 (2H, m), 7.03 (1H, s), 8.19 (1H, s). m/z 277 (M + 1) |
| 56 | 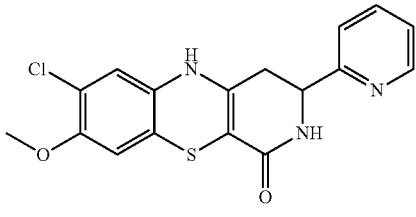 [SMILES: COc1cc2c(cc1Cl)NC1=C(S2)C(=O)NC(c2ccccn2)C1]<br>7-chloro-8-methoxy-3-(pyridin-2-yl)-3,4-dihydro-2H-benzo[b]pyrido[4,3-e][1,4]thiazin-1(5H)-one | 1H NMR (d6-DMSO): 2.75 (2H, m), 3.70 (3H, s), 4.55 (1H, m), 6.43 (1H, s), 6.53 (1H, s), 7.32 (1H, m), 7.36 (1H, m), 7.73 (1H, m), 7.84 (1H, m), 8.27 (1H, s), 8.55 (1H, m). m/z 360 (M + 1) |
| 57 | 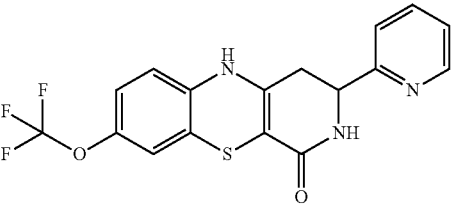<br>3-(pyridin-2-yl)-8-(trifluoromethoxy)-3,4-dihydro-2H-benzo[b]pyrido[4,3-e][1,4]thiazin-1(5H)-one | 1H NMR (d6-DMSO): 2.77 (2H, m), 4.56 (1H, m), 6.41 (1H, m), 6.72 (1H, m), 6.79 (1H, m), 7.32 (1H, m), 7.36 (1H, m), 7.79 (1H, m), 7.85 (1H, m), 8.49 (1H, s), 8.55 (1H, m). m/z 380 (M + 1) |
| 58 | 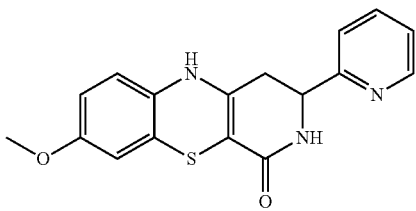 [SMILES: COc1ccc2c(c1)SC1=C(CC(c3ccccn3)NC1=O)N2]<br>8-methoxy-3-(pyridin-2-yl)-3,4-dihydro-2H-benzo-[b]pyrido[4,3-e][1,4]thiazin-1(5H)-one | 1H NMR (d6-DMSO): 2.75 (2H, m), 3.60 (3H, s), 4.54 (1H, m), 6.28 (1H, m), 6.32 (1H, m), 6.38 (1H, m), 7.31 (1H, m), 7.36 (1H, m), 7.63 (1H, m), 7.84 (1H, m), 8.22 (1H, s), 8.55 (1H, m). m/z 326 (M + 1) |

TABLE 1-continued

| # | | NMR/MS |
|---|---|---|
| 59 | 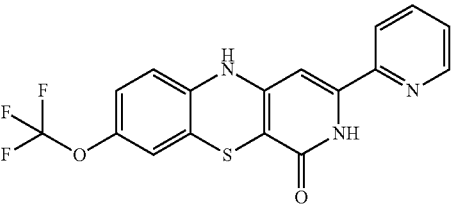 [SMILES: O=c1[nH]c(-c2ccccn2)cc2c1Sc1cc(OC(F)(F)F)ccc1N2] 3-(pyridin-2-yl)-8-(trifluoromethoxy)-2H-benzo-[b]pyrido[4,3-e][1,4]thiazin-1(5H)-one | 1H NMR (d6-DMSO): 6.50 (2H, m), 6.85 (2H, m), 7.44 (1H, m), 7.91 (2H, m), 8.63 (1H, m), 8.94 (1H, s). m/z 378 (M + 1) |
| 60 | 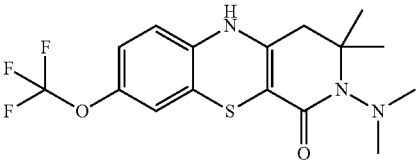 [SMILES: CN(C)N1C(=O)C2=C(CC1(C)C)Nc1ccc(OC(F)(F)F)cc1S2] 2-(dimethylamino)-3,3-dimethyl-8-(trifluoromethoxy)-3,4-dihydro-2H-benzo[b]pyrido[4(3-e][1,4]-thiazin-1(5H)-one | 1H NMR (DMSO-d6): 1.26 (6H, s), 2.28 (2H, s), 2.71 (6H, s), 6.47 (1H, m), 6.76 (1H, m), 6.82 (1H, m), 8.41 (1H, s) m/z 372 (M − 1) |
| 61 | 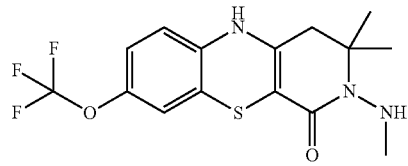 [SMILES: CNN1C(=O)C2=C(CC1(C)C)Nc1ccc(OC(F)(F)F)cc1S2] 3,3-dimethyl-2-(methylamino)-8-(trifluoromethoxy)-3,4-dihydro-2H-benzo[b]pyrido[4,3-e][1,4]-thiazin-1(5H)-one | 1H NMR (DMSO-d6): 1.20 (6H, s), 2.32 (2H, s), 2.43 (3H, d, J = 5.8 Hz), 4.77 (1H, q, J = 5.8 Hz), 6.48 (1H, m), 6.78 (1H, m), 6.83 (1H, m), 8.51 (1H, s) m/z 358 (M − 1) |
| 62 | 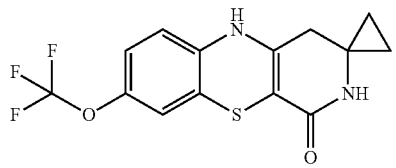 [SMILES: O=C1NC2(CC2)CC2=C1Sc1cc(OC(F)(F)F)ccc1N2] 8-(trifluoromethoxy)-2H,4H-spiro[benzo[b]-pyrido[4,3-e][1,4]thiazine-3,1'-cyclopropan]-1(5H)-one | 1H NMR (DMSO-d6): 0.58 (2H, m), 0.67 (2H, m), 2.22 (2H, s), 6.49 (1H, m), 6.77 (1H, m), 6.84 (1H, m), 7.33 (1H, s), 8.46 (1H, s). m/z 329 (M + 1) |
| 63 | 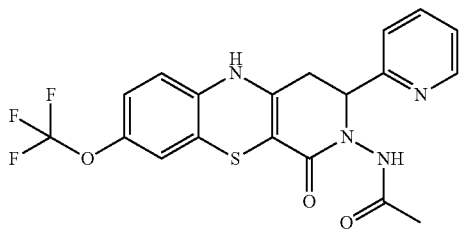 [SMILES: CC(=O)NN1C(=O)C2=C(CC1c1ccccn1)Nc1ccc(OC(F)(F)F)cc1S2] N-(1-oxo-3-(pyridin-2-yl)-8-(trifluoromethoxy)-1,3,4,5-tetrahydro-2H-benzo[b]pyrido[4,3-e]-[1,4]thiazin-2-yl)acetamide | 1H NMR (d6-DMSO): 1.73 (3H, s), 2.86 (2H, m), 4.87 (1H, m), 6.45 (1H, m), 6.80 (1H, m), 6.83 (1H, m), 7.32 (1H, m), 7.35 (1H, m), 7.84 (1H, m), 8.58 (1H, m), 8.66 (1H, s), 9.90 (1H, s). m/z 437 (M +1) |

TABLE 1-continued

| # | | NMR/MS |
|---|---|---|
| 64 | 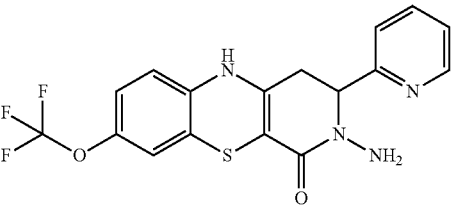 [SMILES: NN1C(=O)C2=C(CC1c1ccccn1)Nc1ccc(OC(F)(F)F)cc1S2]<br>2-amino-3-(pyridin-2-yl)-8-(trifluoromethoxy)-3,4-dihydro-2H-benzo[b]pyrido[4,3-e][1,4]thiazin-1(5H)-one | 1H NMR (d6-DMSO): 2.70 (1H, m), 3.01 (1H, m), 4.74 (1H, m), 4.77 (1H, s), 6.37 (1H, m), 6.74 (1H, m), 6.78 (1H, m), 7.13 (1H, m), 7.32 (1H, m), 7.81 (1H, m), 8.40 (1H, s), 8.56 (1H, m). m/z 395 (M + 1) |
| 65 | 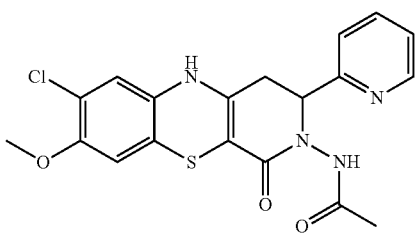 [SMILES: COc1cc2c(cc1Cl)NC1=C(S2)C(=O)N(NC(C)=O)C(c2ccccn2)C1]<br>N-(7-chloro-8-methoxy-1-oxo-3-(pyridin-2-yl)-1,3,4,5-tetrahydro-2H-benzo[b]pyrido[4,3-e]-[1,4]thiazin-2-yl)acetamide | 1H NMR (d6-DMSO): 1.72 (3H, m), 2.84 (2H, m), 3.71 (3H, s), 4.86 (1H, m), 6.46 (1H, s), 6.60 (1H, s), 7.32 (1H, m), 7.35 (1H, m), 7.84 (1H, m), 8.45 (1H, s), 8.57 (1H, m), 987 (1H, s). m/z 417 (M + 1) |
| 66 | 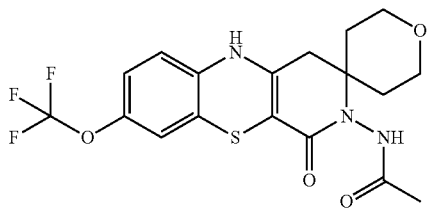 [SMILES: CC(=O)NN1C(=O)C2=C(CC13CCOCC3)Nc1ccc(OC(F)(F)F)cc1S2]<br>N-(1-oxo-8-(trifluoromethoxy)-1,2',3',5,5',6'-hexahydro-2H,4H-spiro[benzo[b]pyrido[4,3-e]-[1,4]thiazine-3,4'-pyran]-2-yl)acetamide | 1H NMR (DMSO-d6): 1.50 (1H, m), 1.62 (1H, m), 1.76 (1H, m), 1.88 (3H, s), 1.93 (1H, m), 2.59 (1H, m), 2.70 (1H, m), 3.33 (2H, m), 3.78 (2H, m), 6.49 (1H, m), 6.81 (1H, m), 6.85 (1H, m), 8.68 (1H, s), 9.54 (1H, s). m/z 430 (M + 1) |
| 67 | 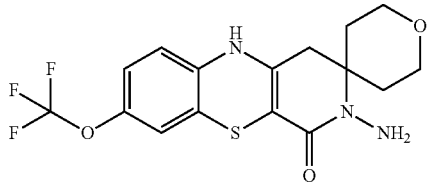 [SMILES: NN1C(=O)C2=C(CC13CCOCC3)Nc1ccc(OC(F)(F)F)cc1S2]<br>2-amino-8-(trifluoromethoxy)-2',3',5',6'-tetrahydro-2H,4H-spiro[benzo[b]pyrido[4,3-e][1,4]thiazine-3,4'-pyran]-1(5H)-one | 1H NMR (DMSO-d6): 1.42 (2H, m), 2.19 (2H, m), 2.57 (2H, s), 3.29 (2H, m), 3.82 (2H, m), 4.40 (2H, m), 6.46 (1H, m), 6.77 (1H, m), 6.83 (1H, m), 8.52 (1H, s). m/z 388 (M + 1) |
| 68 | 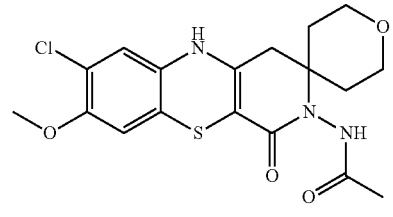 [SMILES: COc1cc2c(cc1Cl)NC1=C(S2)C(=O)N(NC(C)=O)C2(CCOCC2)C1]<br>N-(7-chloro-8-methoxy-1-oxo-1,2',3',5,5',6'-hexahydro-2H,4H-spiro[benzo[b]pyrido[4,3-e]-[1,4]thiazine-3,4'-pyran]-2-yl)acetamide | 1H NMR (DMSO-d6): 1.49 (1H, m), 1.61 (1H, m), 1.75 (1H, m), 1.88 (3H, s), 1.93 (1H, m), 2.58 (1H, m), 2.72 (1H, m), 3.33 (2H, m), 3.71 (3H, s), 378 (2H, m), 6.50 (1H, s), 6.61 (1H, s), 8.48 (1H, s), 9.51 (1H, s). m/z 410 (M + 1) |

TABLE 1-continued

| # | | NMR/MS |
|---|---|---|
| 69 | 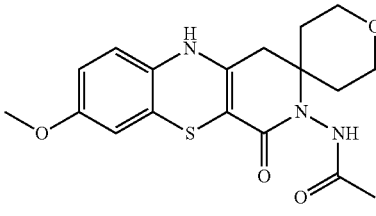<br>N-(8-methoxy-1-oxo-1,2',3',5,5',6'-hexahydro-2H,4H-spiro[benzo[b]pyrido[4,3-e][1,4]thiazine-3,4'-pyran]-2-yl)acetamide | 1H NMR (DMSO-d6): 1.48 (1H, m), 1.61 (1H, m), 1.74 (1H, m), 1.88 (3H, s), 1.93 (1H, m), 2.56 (1H, m), 2.76 (1H, m), 3.33 (2H, m), 3.62 (3H, s), 3.78 (2H, m), 6.35 (1H, m), 6.39 (1H, m), 6.44 (1H, m), 8.42 (1H, s), 9.48 (1H, s). m/z 376 (M + 1) |
| 70 | 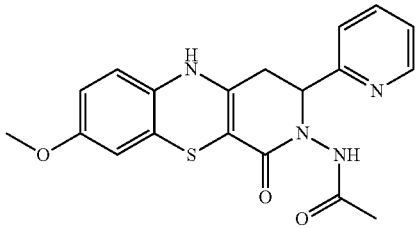 [SMILES: COc1ccc2c(c1)SC1=C(CC(c3ccccn3)N(NC(C)=O)C1=O)N2]<br>N-(8-methoxy-1-oxo-3-(pyridin-2-yl)-1,3,4,5-tetrahydro-2H-benzo[b]pyrido[4,3-e][1,4]thiazin-2-yl)acetamide | 1H NMR (d6-DMSO): 1.72 (3H, s), 2.83 (2H, m), 3.61 (3H, s), 4.85 (1H, m), 6.35 (2H, m), 6.41 (1H, m), 7.33 (2H, m), 7.84 (1H, m), 8.40 (1H, s), 8.57 (1H, m), 9.85 (1H, s). m/z 383 (M + 1) |
| 71 | 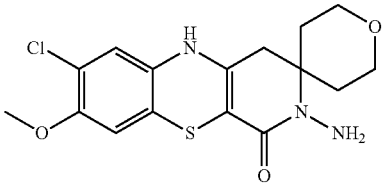 [SMILES: COc1cc2c(cc1Cl)NC1=C(S2)C(=O)N(N)C2(CCOCC2)C1]<br>2-amino-7-chloro-8-methoxy-2',3',5',6'-tetrahydro-2H,4H-spiro[benzo[b]pyrido[4,3-e][1,4]thiazine-3,4'-pyran]-1(5H)-one | 1H NMR (DMSO-d6): 1.41 (2H, m), 2.18 (2H, m), 2.56 (2H, s), 3.30 (2H, m), 3.71 (3H, s), 3.82 (2H, m), 4.39 (2H, s), 6.47 (1H, s), 6.58 (1H, s), 8.33 (1H, s). m/z 368 (M + 1) |
| 72 | 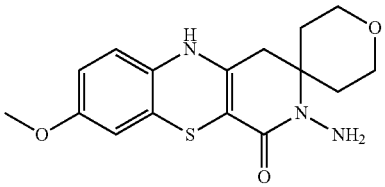 [SMILES: COc1ccc2c(c1)SC1=C(CC3(CCOCC3)N(N)C1=O)N2]<br>2-amino-8-methoxy-2',3',5',6'-tetrahydro-2H,4H-spiro[benzo[b]pyrido[4,3-e][1,4]thiazine-3,4'-pyran]-1(5H)-one | 1H NMR (DMSO-d6): 1.41 (2H, m), 2.18 (2H, m), 2.57 (2H, s), 3.30 (2H, m), 3.62 (3H, s), 3.81 (2H, m), 4.36 (2H, s), 6.33 (1H, m), 6.38 (1H, m), 6.42 (1H, m), 8.32 (1H, s). m/z 334 (M + 1) |
| 73 | 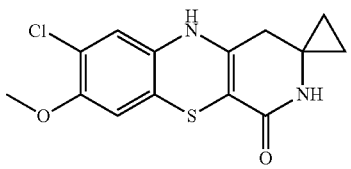 [SMILES: COc1cc2c(cc1Cl)NC1=C(S2)C(=O)NC2(CC2)C1]<br>7-chloro-8-methoxy-2H,4H-spiro[benzo[b]-pyrido[4,3-e][1,4]thiazine-3,1'-cyclopropan]-1(5H)-one | 1H NMR (DMSO-d6): 0.59 (2H, m), 0.66 (2H, m), 2.20 (2H, s), 3.72 (3H, s), 6.51 (1H, s), 6.57 (1H, s), 7.26 (1H, s), 8.21 (1H, s). m/z 309 (M + 1) |

TABLE 1-continued

| # | | NMR/MS |
|---|---|---|
| 74 | 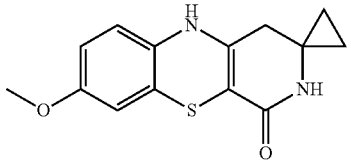 [SMILES: COc1ccc2c(c1)SC1=C(CC3(CC3)NC1=O)N2]<br>8-methoxy-2H,4H-spiro[benzo[b]pyrido[4,3-e]-[1,4]thiazine-3,1'-cyclopropan]-1(5H)-one | 1H NMR (DMSO-d6): 0.58 (2H, m), 0.65 (2H, m), 2.20 (2H, s), 3.62 (3H, s), 6.33 (1H, m), 6.39 (1H, m), 6.42 (1H, m), 7.16 (1H, s), 8.17 (1H, s). m/z 275 (M + 1) |
| 75 | 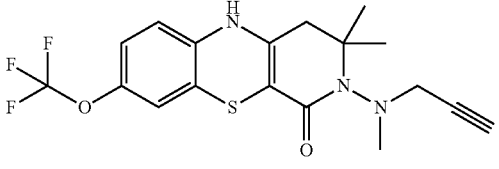 [SMILES: C#CCN(C)N1C(=O)C2=C(CC1(C)C)Nc1ccc(OC(F)(F)F)cc1S2]<br>3,3-dimethyl-2-(methyl(prop-2-yn-1-yl)amino)-8-(trifluoromethoxy)-3,4-dihydro-2H-benzo[b]-pyrido[4,3-e][1,4]thiazin-1(5H)-one | 1H NMR (CDCl3): 1.38 (3H, s), 1.53 (3H, s), 2.66 (3H, s), 2.86 (1H, m), 2.95 (1H, m), 4.58 (1H, m), 4.86 (1H, m), 5.41 (1H, m), 7.07 (1H, m), 7.13 (1H, m), 7.32 (1H, m). m/z 398 (M + 1) |
| 76 | 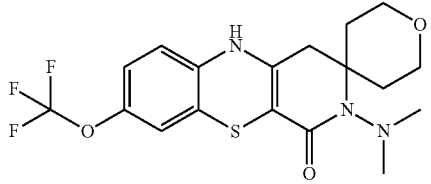<br>2-(dimethylamino)-8-(trifluoromethoxy)-2',3',5',6'-tetrahydro-2H(4H-spiro[benzo[b]pyrido[4,3-e][1,4]-thiazine-3,4'-pyran]-1(5H)-one | m/z 432 (M + 1) |
| 77 | 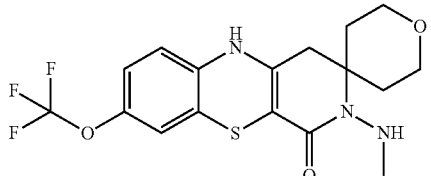<br>2-(methylamino)-8-(trifluoromethoxy)-2',3',5',6'-tetrahydro-2H(4H-spiro[benzo[b]pyrido[4,3-e][1,4]-thiazine-3,4'-pyran]-1(5H)-one | 1H NMR (DMSO-d6): 1.49 (2H, m), 2.42 (3H, d, J = 6.1 Hz), 2.55 (2H, m), 2.60 (2H, m), 3.50 (2H, s), 3.81 (2H, m), 4.83 (1H, q, J = 6.1 Hz), 6.47 (1H, m), 6.79 (1H, m), 6.83 (1H, m), 8.57 (1H, s). m/z 402 (M + 1) |
| 78 | 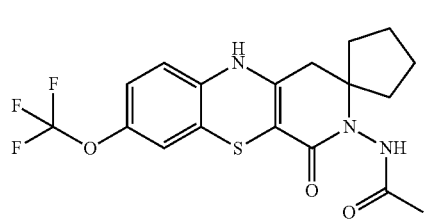 [SMILES: CC(=O)NN1C(=O)C2=C(CC13CCCC3)Nc1ccc(OC(F)(F)F)cc1S2]<br>N-(1-oxo-8-(trifluoromethoxy)-1,5-dihydro-2H,4H-spiro[benzo[b]pyrido[4,3-e][1,4]thiazine-3,1'-cyclopentan]-2-yl)acetamide | m/z 412 (M − 1) |

TABLE 1-continued

| # | | NMR/MS |
|---|---|---|
| 79 | 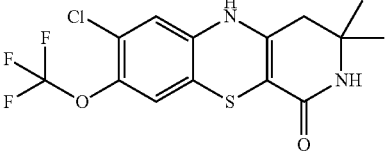<br>7-chloro-3,3-dimethyl-8-(trifluoromethoxy)-3,4-dihydro-2H-benzo[b]pyrido[4,3-e][1,4]thiazin-1(5H)-one | 1H NMR (DMSO-d6): 1.18 (6H, s), 2.16 (2H, s), 6.57 (1H, s), 6.96 (1H, s), 7.26 (1H, s), 8.48 (1H, s) m/z 365 (M + 1) |
| 80 | 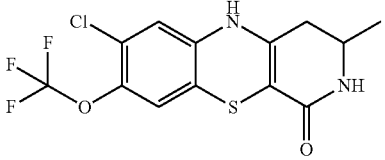 [SMILES: CC1CC2=C(Sc3cc(OC(F)(F)F)c(Cl)cc3N2)C(=O)N1]<br>7-chloro-3-methyl-8-(trifluoromethoxy)-3,4-dihydro-2H-benzo[b]pyrido[4,3-e][1,4]thiazin-1(5H)-one | 1H NMR (d6-DMSO): 1.10 (3H, d, J = 6.4 Hz), 12.05 (1H, m), 2.20 (1H, m), 3.50 (1H, m), 6.58 (1H, s), 6.96 (1H, s), 7.25 (1H, s), 8.54 (1H, s). m/z 351 (M + 1) |
| 81 | 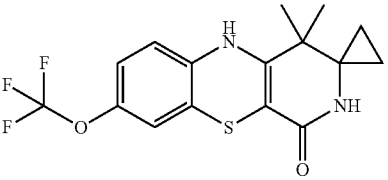 [SMILES: CC1(C)C2=C(Sc3cc(OC(F)(F)F)ccc3N2)C(=O)NC12CC2]<br>4,4-dimethyl-8-(trifluoromethoxy)-2H(4H-spiro-[benzo[b]pyrido[4,3-e][1,4]thiazine-3,1'-cyclopropan]-1(5H)-one | 1H NMR (DMSO-d6): 0.52 (2H, m), 0.81 (2H, m), 1.01 (6H, s), 6.79 (1H, m), 6.84 (1H, m), 6.88 (1H, m), 7.34 (1H, s), 7.71 (1H, s). m/z 355 (M − 1) |
| 82 | 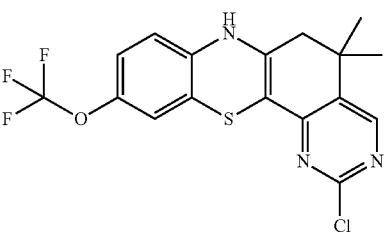<br>2-chloro-5,5-dimethyl-10-(trifluoromethoxy)-5,7-dihydro-6H-pyrimido[5,4-c]phenothiazine | 1H NMR (CDCl3): 1.53 (6H, s), 6.39 (1H, m), 6.54 (1H, m), 6.70 (1H, m), 6.74 (1H, m), 8.43 (1H, s). m/z 414 (M + 1) |
| 83 | 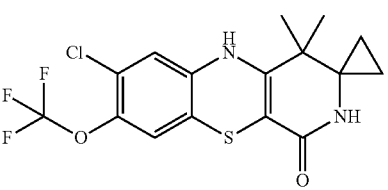 [SMILES: CC1(C)C2=C(Sc3cc(OC(F)(F)F)c(Cl)cc3N2)C(=O)NC12CC2]<br>7-chloro-4,4-dimethyl-8-(trifluoromethoxy)-2H,4H-spiro[benzo[b]pyrido[4,3-e][1,4]thiazine-3,1'-cyclopropan]-1(5H)-one | 1H NMR (DMSO-d6): 0.52 (2H, m), 0.81 (2H, m), 1.00 (6H, s), 7.00 (1H, s), 7.03 (1H, s), 7.43 (1H, s), 7.75 (1H, s). m/z 391 (M + 1) |

TABLE 1-continued

| # | | NMR/MS |
|---|---|---|
| 84 | 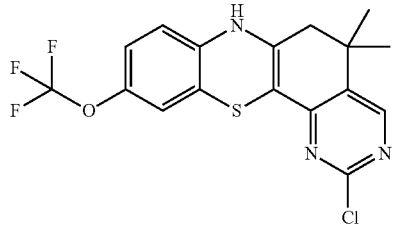 [SMILES: CC1(C)CC2=C(Sc3cc(OC(F)(F)F)ccc3N2)c2nc(Cl)ncc21]<br>2-chloro-5,5-dimethyl-10-(trifluoromethoxy)-5,7-dihydro-6H-pyrimido[5,4-c]phenothiazine | m/z 400 (M + 1) |
| 85 | 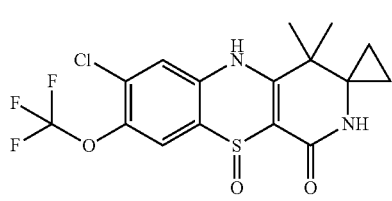 [SMILES: CC1(C)C2=C(C(=O)NC13CC3)S(=O)c1cc(OC(F)(F)F)c(Cl)cc1N2]<br>7-chloro-4,4-dimethyl-8-(trifluoromethoxy)-2H,4H-spiro[benzo[b]pyrido[4,3-e][1,4]thiazine-3,1'-cyclopropan]-1(5H)-one 10-oxide | m/z 351 (M − 1) |
| 86 | 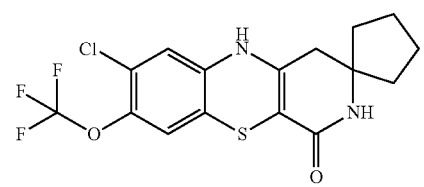 [SMILES: O=C1NC2(CCCC2)CC2=C1Sc1cc(OC(F)(F)F)c(Cl)cc1N2]<br>7-chloro-8-(trifluoromethoxy)-2H,4H-spiro[benzo[b]pyrido[4,3-e][1,4]thiazine-3,1'-cyclopentan]-1(5H)-one | 1H NMR (DMSO-d6): 1.52 (2H, m), 1.62 (4H, m), 1.69 (2H, m), 2.23 (2H, s), 6.56 (1H, s), 6.96 (1H, s), 7.45 (1H, s), 8.51 (1H, s). m/z 391 (M + 1) |
| 87 | 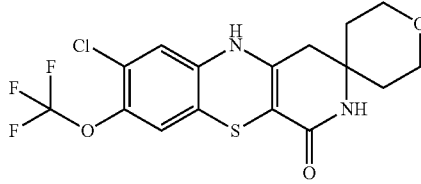<br>7-chloro-8-(trifluoromethoxy)-2',3',5',6'-tetrahydro-2H,4H-spiro[benzo[b]pyrido[4,3-e][1,4]thiazine-3,4'-pyran]-1(5H)-one | 1H NMR (DMSO-d6): 1.63 (4H, m), 2.33 (2H, s), 3.44 (2H, m), 3.71 (2H, m), 6.57 (1H, s), 6.97 (1H, s), 7.53 (1H, s), 8.56 (1H, s). m/z 407 (M + 1) |
| 88 | 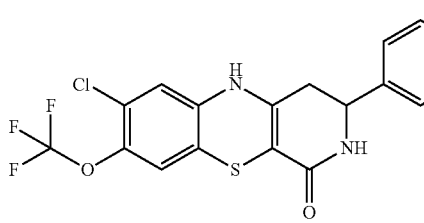<br>7-chloro-3-phenyl-8-(trifluoromethoxy)-3,4-dihydro-2H-benzo[b]pyrido[4,3-e][1,4]thiazin-1(5H)-one | 1H NMR (d6-DMSO): 2.36 (1H, m), 2.59 (1H, m), 4.61 (1H, m), 6.52 (1H, s), 6.98 (1H, s), 7.25-7.42 (5H, m), 7.68 (1H, s), 854 (1H, s). m/z 413 (M + 1) |

TABLE 1-continued

| # | | NMR/MS |
|---|---|---|
| 89 | 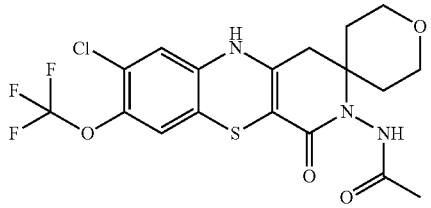 [SMILES: CC(=O)NN1C(=O)C2=C(CC13CCOCC3)Nc1cc(Cl)c(OC(F)(F)F)cc1S2]<br>N-(7-chloro-1-oxo-8-(trifluoromethoxy)-1,2',3',5,5',6'-hexahydro-2H,4H-spiro[benzo-[b]pyrido[4,3-e][1,4]thiazine-3,4'-pyranl]-yl)-acetamide | 1H NMR (DMSO-d6): 1.51 (1H, m), 1.63 (1H, m), 1.77 (1H, m), 1.89 (3H, s), 1.94 (1H, m), 2.60 (1H, m), 2.72 (1H, m), 3.77 (2H, m), 3.80 (2H, m), 6.58 (1H, s), 7.02 (1H, s), 8.77 (1H, s), 9.56 (1H, s). m/z 464 (M + 1) |
| 90 | 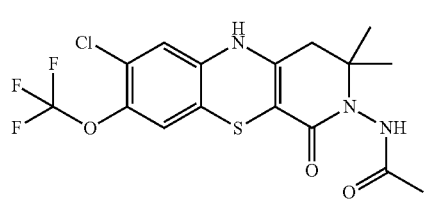 [SMILES: CC(=O)NN1C(=O)C2=C(CC1(C)C)Nc1cc(Cl)c(OC(F)(F)F)cc1S2]<br>N-(7-chloro-3,3-dimethyl-1-oxo-8-(trifluoro-methoxy)-1,3,4,5-tetrahydro-2H-benzo[b]-pyrido[4,3-e][1,4]thiazin-2-yl)acetamide | 1H NMR (DMSO-d6): 1.18 (6H, s), 1.86 (3H, s), 2.23 (1H, m), 2.51 (1H, m), 6.60 (1H, s), 7.02 (1H, s), 8.69 (1H, s), 9.50 (1H, s). m/z 422 (M + 1) |
| 91 | 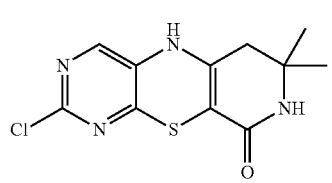 [SMILES: CC1(C)CC2=C(Sc3nc(Cl)ncc3N2)C(=O)N1]<br>2-chloro-7,7-dimethyl-7,8-dihydro-5H-pyrido-[3,4-b]pyrimido[5,4-e][1,4]thiazin-9(6H)-one | 1H NMR (DMSO-d6): 1.17 (6H, s), 2.11 (2H, s), 7.27 (1H, s), 7.38 (1H, s), 8.61 (1H, s) m/z 282 (M − 1) |
| 92 | 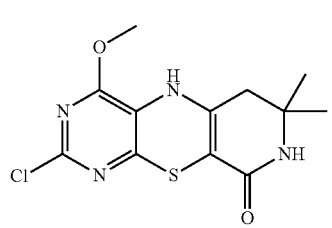 [SMILES: COc1nc(Cl)nc2c1NC1=C(S2)C(=O)NC(C)(C)C1]<br>2-chloro-4-methoxy-7,7-dimethyl-7,8-dihydro-5H-pyrido[3,4-b]pyrimido[5,4-e][1,4]thiazin-9(6H)-one | 1H NMR (DMSO-d6): 1.19 (6H, s), 2.20 (2H, s), 3.87 (3H, s), 7.34 (1H, s), 8.18 (1H, s) m/z 313 (M + 1) |
| 93 | 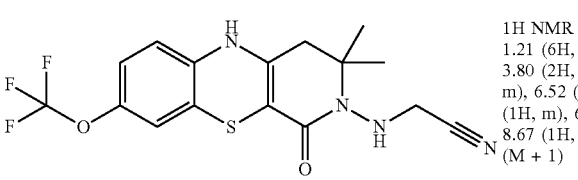<br>2-((3,3-dimethyl-1-oxo-8-(trifluoromethoxy)-1,3,4,5-tetrahydro-2H-benzo[b]pyrido[4,3-e]-[1,4]thiazin-2-yl)amino)acetonitrile | 1H NMR (DMSO-d6): 1.21 (6H, s), 2.37 (2H, s), 3.80 (2H, m), 5.60 (1H, m), 6.52 (1H, m), 6.81 (1H, m), 6.85 (1H, m), 8.67 (1H, s). m/z 385 (M + 1) |

TABLE 1-continued

| # | | NMR/MS |
|---|---|---|
| 94 | 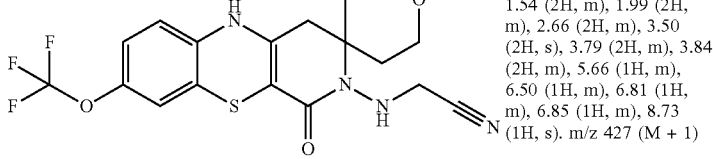<br>2-((1-oxo-8-(trifluoromethoxy)-1,2',3',5,5',6'-hex-ahydro-2H,4H-spiro[benzo[b]pyrido[4,3-e][1,4]-thiazine-3,4'-pyran]-2-yl)amino)acetonitrile | 1H NMR (DMSO-d6): 1.54 (2H, m), 1.99 (2H, m), 2.66 (2H, m), 3.50 (2H, s), 3.79 (2H, m), 3.84 (2H, m), 5.66 (1H, m), 6.50 (1H, m), 6.81 (1H, m), 6.85 (1H, m), 8.73 (1H, s). m/z 427 (M + 1) |
| 95 | 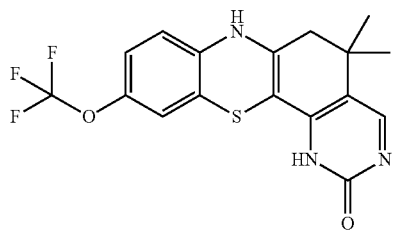 [SMILES: CC1(C)CC2=C(Sc3cc(OC(F)(F)F)ccc3N2)c2[nH]c(=O)ncc21]<br>5,5-dimethyl-10-(trifluoromethoxy)-5,7-dihydro-1H-pyrimido[5,4-c]phenothiazin-2(6H)-one | 1H NMR (DMSO-d6): 1.18 (6H, s), 2.23 (2H, s), 6.58 (1H, m), 6.84 (2H, m), 7.28 (1H, m), 9.08 (1H, s), 10.88 (1H, s). m/z 382(M + 1). |
| 96 | 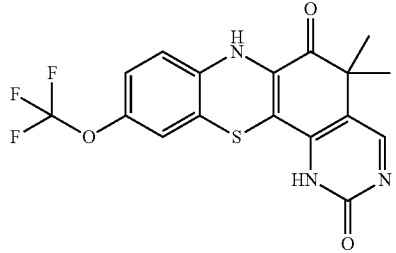 [SMILES: CC1(C)C(=O)C2=C(Sc3cc(OC(F)(F)F)ccc3N2)c2[nH]c(=O)ncc21]<br>5,5-dimethyl-10-(trifluoromethoxy)-5,7-dihydro-1H-pyrimido[5,4-c]phenothiazine-2,6-dione | 1H NMR (DMSO-d6): 1.37 (6H, s), 6.87 (1H, m), 6.92 (1H, m), 6.94 (1H, m), 7.92 (1H, s), 8.62 (1H, s), 11.79 (1H, s). m/z 396 (M + 1) |
| 97 | 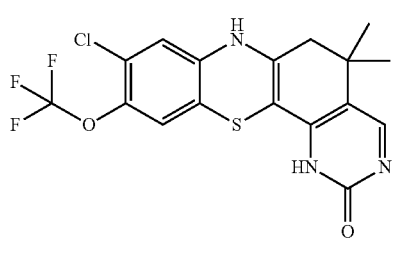 [SMILES: CC1(C)CC2=C(Sc3cc(OC(F)(F)F)c(Cl)cc3N2)c2[nH]c(=O)ncc21]<br>9-chloro-5,5-dimethyl-10-(trifluoromethoxy)-5,7-dihydro-1H-pyrimido[5,4-c]phenothiazin-2(6H)-one | 1H NMR (MeOH-d4): 1.29 (6H, s), 2.28 (2H, s), 6.41 (1H, m), 6.88 (1H, m), 7.35 (1H, s). m/z 416 (M + 1) |
| 98 | 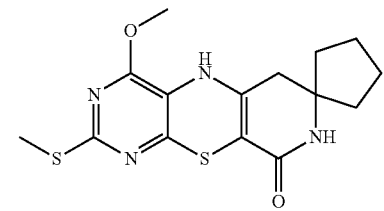 [SMILES: COc1nc(SC)nc2c1NC1=C(S2)C(=O)NC2(CCCC2)C1]<br>4'-methoxy-2'-(methylthio)-5'H,6'H-spiro[cyclo-pentane-1,7'-pyrido[3,4-b]pyrimido[5,4-e][1,4]-thiazin]-9'(8'H)-one | 1H NMR (DMSO-d6): 1.51 (2H, m), 1.58 (4H, m), 1.68 (2H, m), 2.30 (2H, s), 2.39 (3H, s), 3.87 (3H, s), 7.41 (1H, s), 7.61 (1H, s). m/z 351 (M + 1) |

TABLE 1-continued

| # | | NMR/MS |
|---|---|---|
| 99 | 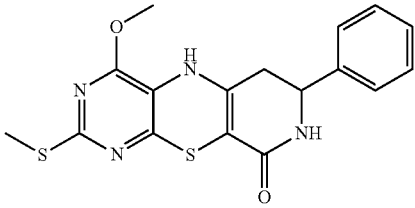 [SMILES: COc1nc(SC)nc2c1NC1=C(S2)C(=O)NC(c2ccccc2)C1]  4-methoxy-2-(methylthio)-7-phenyl-7,8-dihydro-5H-pyrido[3,4-b]pyrimido[5,4-e][1,4]thiazin-9(6H)-one | 1H NMR (d6-DMSO): 2.38 (3H, s), 2.47 (1H, m), 2.64 (1H, m), 3.85 (3H, s), 4.54 (1H, m), 7.25-7.42 (5H, m), 7.66 (1H, m), 7.72 (1H, s). m/z 373 (M + 1) |

General Procedures

Compounds of the invention can be prepared by a variety of synthetic routes analogously to methods known in the literature using suitable starting materials. Compounds of formula (I) can alternatively be prepared according to the following reaction routes. Some compounds included in the formula (I) can be obtained by converting the functional groups of other compounds of formula (I) obtained in accordance with the following reaction routes, by well-known reaction steps such as oxidation, reduction, hydrolysis, acylation, alkylation, amidation, amination, sulfonication, and others.

The compound of the present invention can be prepared by allowing a compound of formula (IIa) or (IIb)

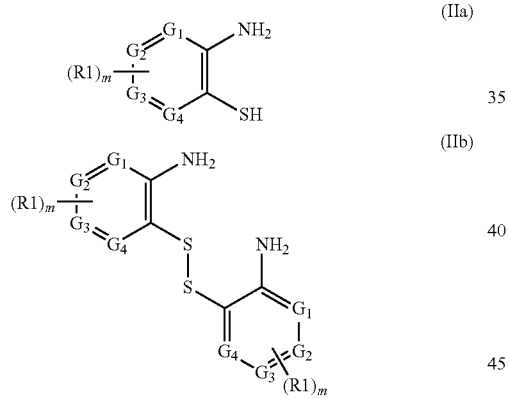

wherein G1, G2, G3, G4, R1, and m are as defined above; to react with a compound of formula (III)

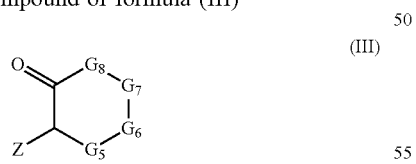

wherein G8 is $C(R8)_2$ or $[CH_2]n$; n, G5, G6, and G7 are as defined herein; and Z is H or halogen;

to obtain a compound of formula (I);

and when R8 is $CH_2$ optionally allowing the obtained compound wherein to oxidize to obtain a compound of formula (I) wherein R8 is —(C=O)—;

and optionally converting the obtained compound to a corresponding pharmaceutically acceptable salt thereof.

For example, in case where G5 is —(C=O), compounds of formula (I) can be prepared according to the following reaction scheme:

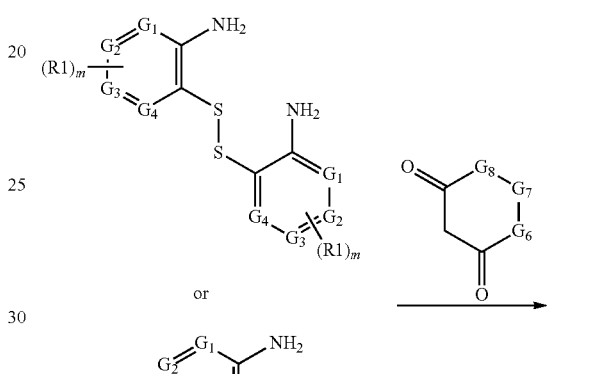

For further example, in case where G5 and G6 form together a 5 membered unsaturated cyclic ring comprising one or two heteroatoms selected from N, O, and S, and being optionally substituted one or two times with R5, compounds of formula (I) can be prepared according to one of the following reactions schemes:

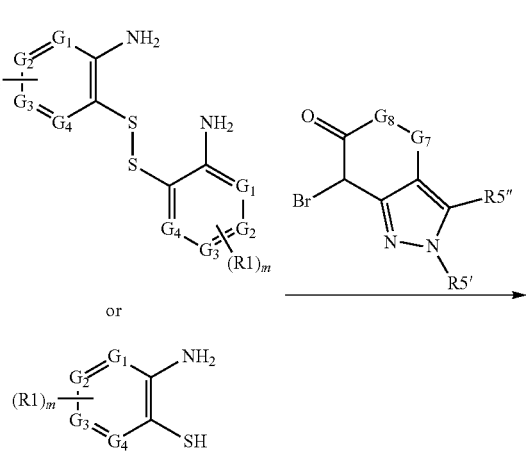

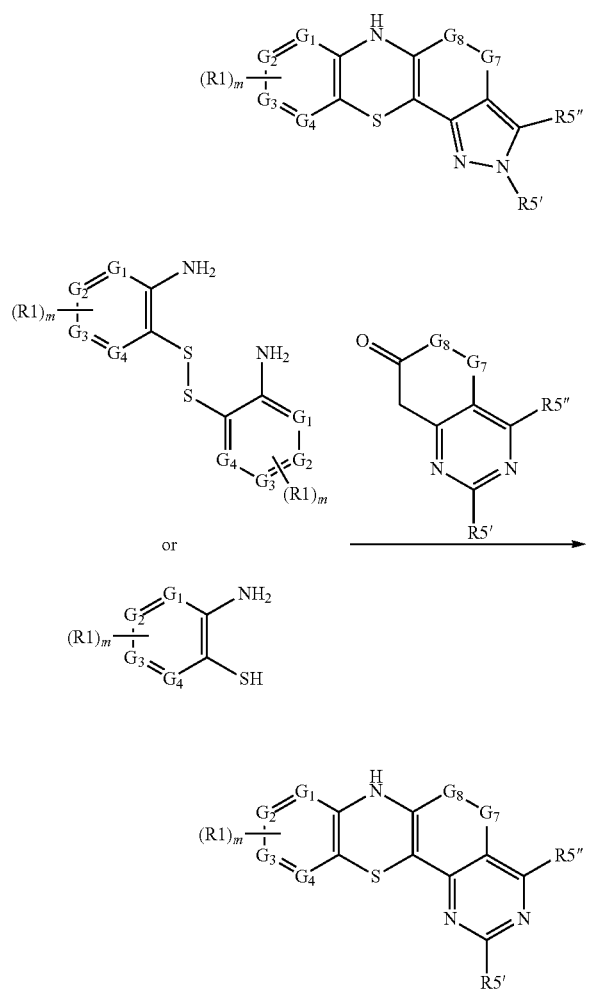

Compounds of formula (IIb) can be obtained by reacting a compound of formula (V)

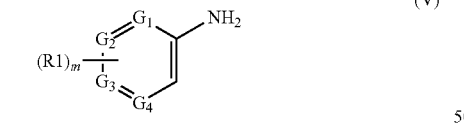

wherein G1, G2, G3, G4, R1, and m are as defined above; with potassium thiocyanate to obtain a compound of formula (IV)

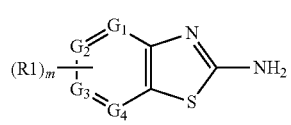

and treating the obtained compound of formula (IV) with base, preferably KOH, to obtain a corresponding compound of formula (IIb)

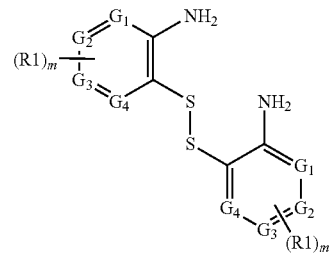

wherein G1, G2, G3, G4, R1, and m are as defined above.
For example compounds of formula (IIb) can be obtained according to the following reaction scheme:

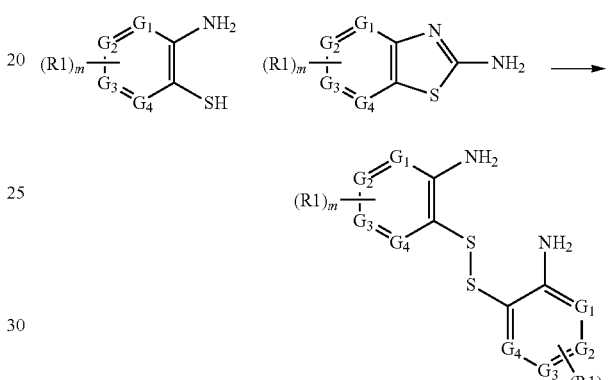

Compounds of formula (III) can be obtained from commercial sources or prepared by one of the following routes.
Compounds of formula (III). wherein G5 is —(C═O)—: G6 is NR6: and G7 is C(R7)$_2$, can for example be prepared by the following reaction scheme:

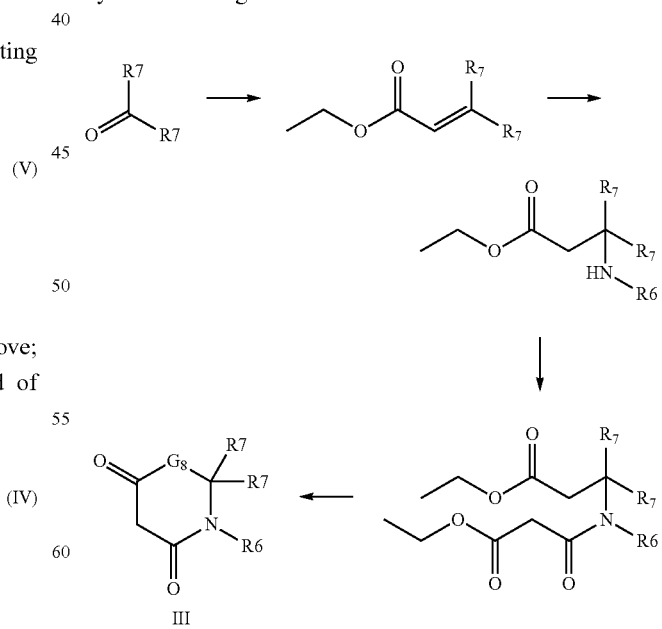

Compounds of formula (III), wherein G5 is —(C═O)—; G6 is NR6; and G8 is C(R8)$_2$, can for example be prepared by the following reaction scheme:

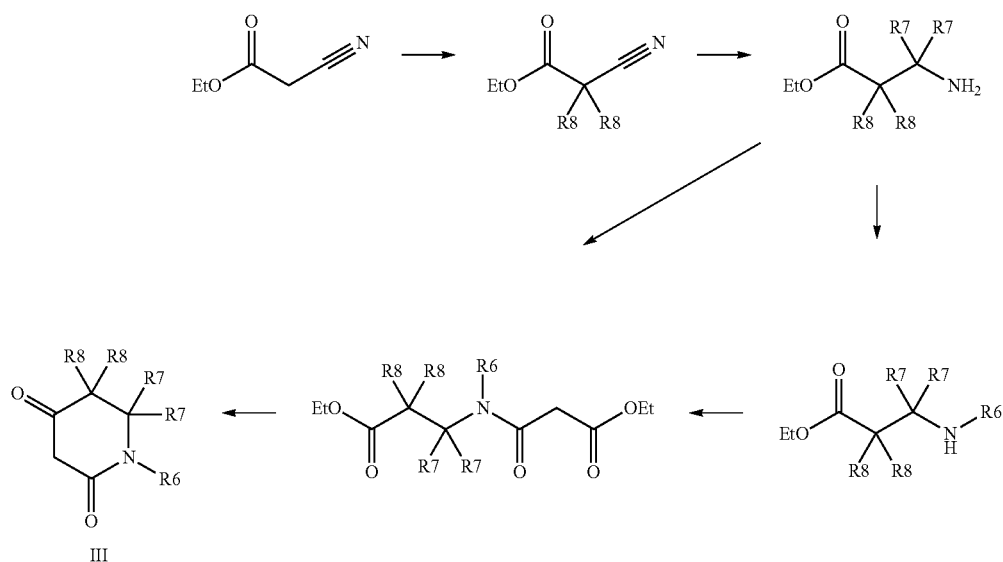

Compounds of formula (III) wherein G5 is —(C=O)—; G6 is NR6, and G8 is $[CH_2]_kC(R8)_2$ can for example be prepared by the following reaction scheme:

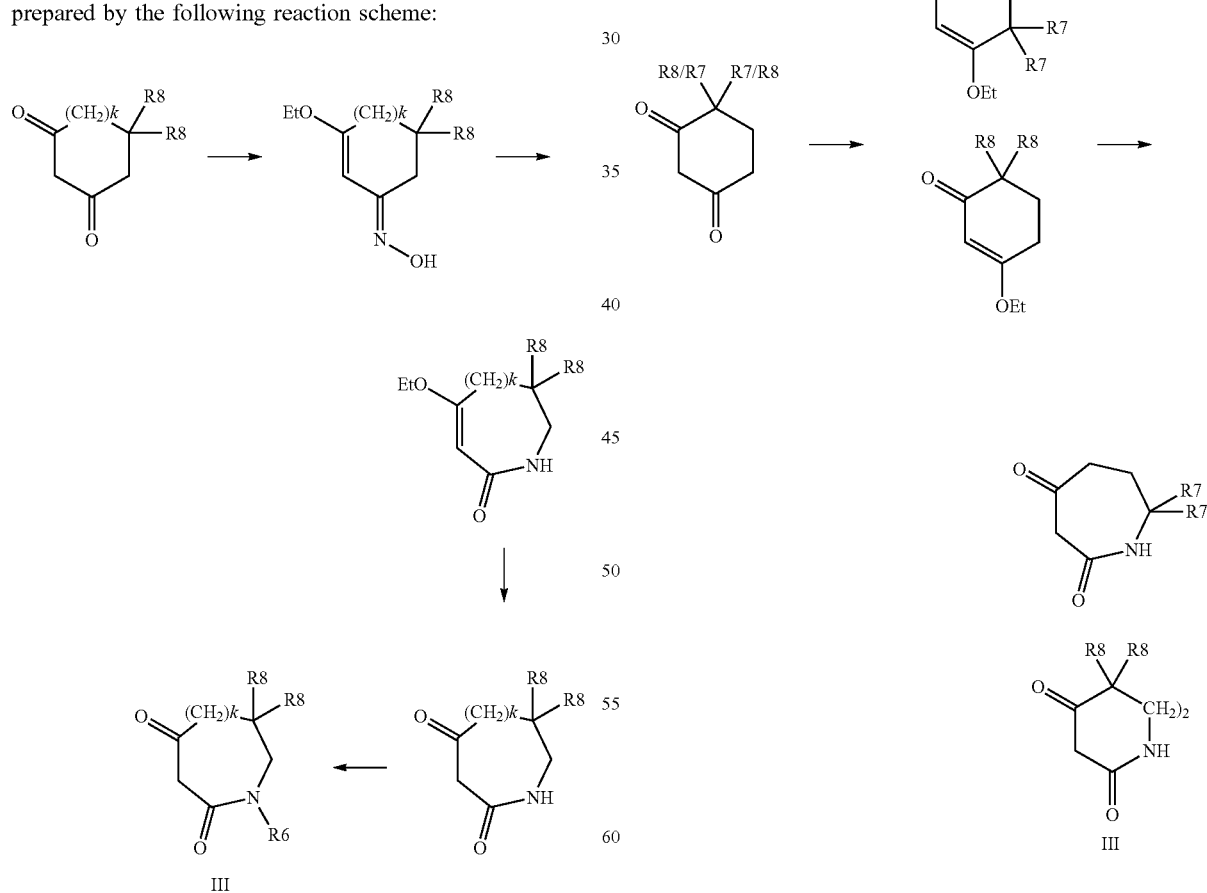

Compounds of formula (III) wherein G5 is —(C=O)—; G6 is NR6, and G8 is $C(R8)_2CH_2$; or $[CH2]_2$, can for example be prepared by the following reaction scheme:

Compounds of formula (III), wherein G5 is —(C=O)—; G6 is $CH_2$; and G7 is O, can for example be prepared by the following reaction scheme:

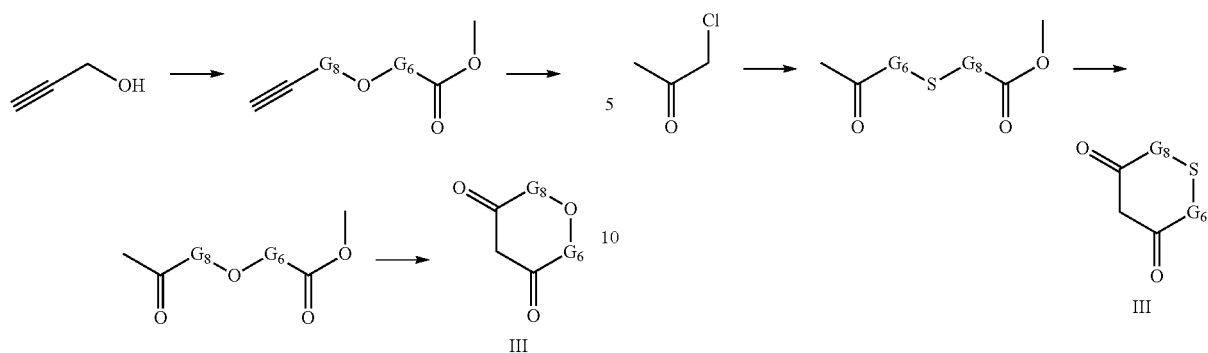

Compounds of formula (III), wherein G5 is —(C=O)—; G6 is CH$_2$; and G7 is S, can for example be Prepared by the following reaction scheme:

Compounds of formula (III), wherein G5 and G6 form together a 5 membered unsaturated cyclic ring comprising one or two heteroatoms selected from N, O, and S, optionally substituted one or two times with R5, can be prepared by the following reaction scheme:

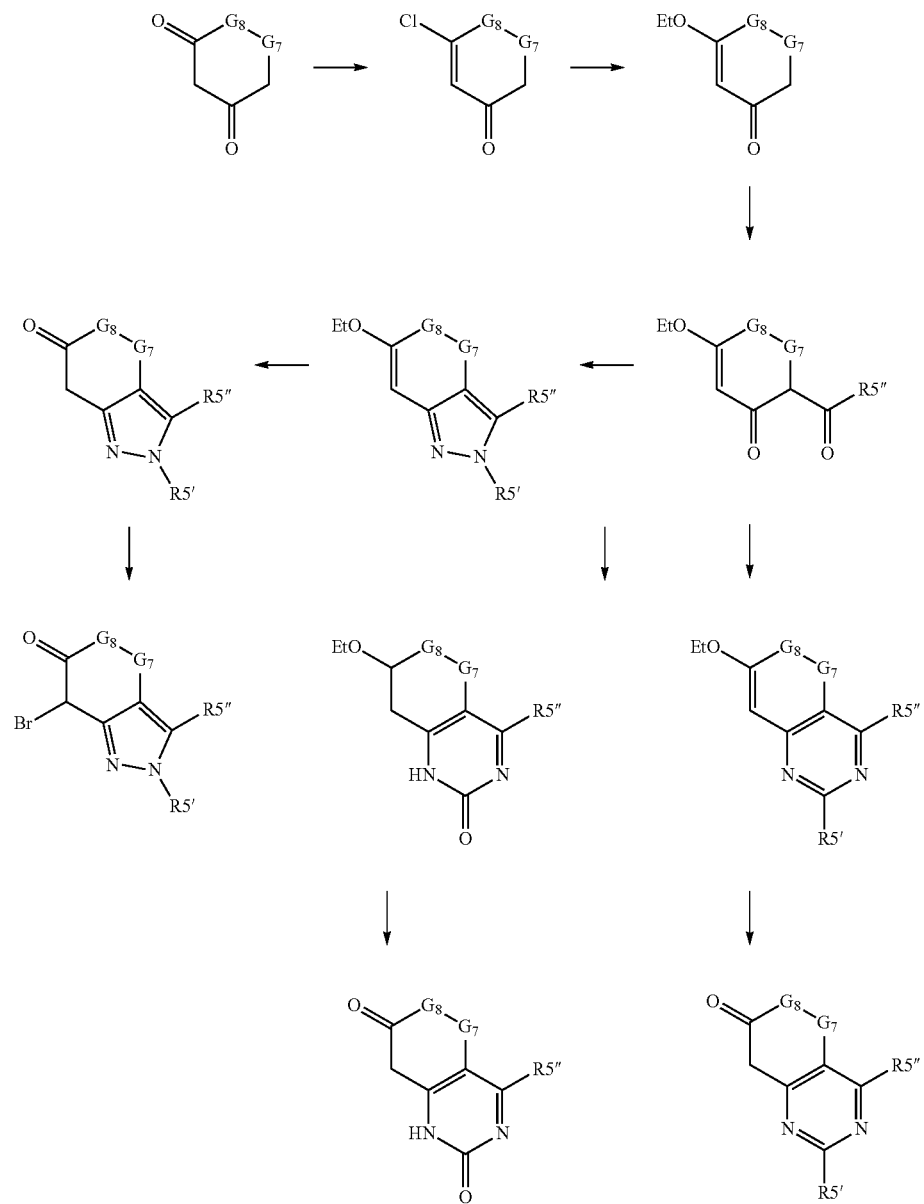

The following examples illustrate the preparation of compounds of Formula (I) or (I').

Preparation of Intermediates

Intermediate IIb-2. 2-{[2-amino-5-(trifluoromethoxy)phenyl]disulfanyl}-4-(trifluoromethoxy)aniline

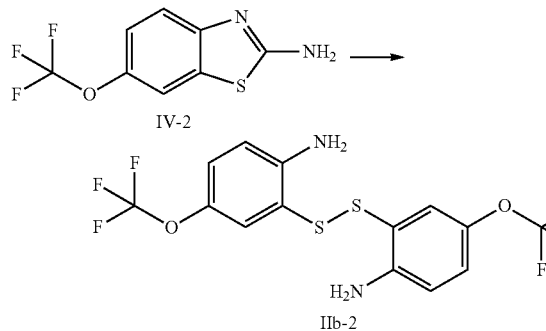

IV-2:

4-Trifluoromethoxyaniline (2 g, 11.3 mmol) and potassium thiocyanate (4.38 g, 45.1 mmol) was solved in acetic acid (20 ml). Bromine (0.57 ml, 11.3 mmol) in acetic acid (5 ml) was added dropwise. The resulting mixture was stirred at RT for 16 hours. After completion of the reaction, the reaction mixture was poured into ice water and neutralized with aqueous ammonia. The aqueous phase was extracted with ethyl acetate. The organic phase was washed with water and brine, dried over sodium sulphate and concentrated under reduced pressure. Yield of 6-(trifluoromethoxy)-1,3-benzothiazol-2-amine (IV-2) after flash chromatography (100-200 mesh size silica gel, 20% ethyl acetate in hexane) was 1.8 g.

IIb-2:

6-(trifluoromethoxy)-1,3-benzothiazol-2-amine (IV-2) (0.5 g, 2.14 mmol) was suspended with 25% aqueous KOH (20 ml) solution. The mixture was heated at 120° C. for 16 hours. After completion of the reaction the mixture was cooled to RT and poured into ice water. The mixture was neutralized with 50% HCl solution and extracted with ethyl acetate. Organic layer was separated, dried over sodium sulphate and concentrated under reduced pressure. The yield of 2-{[2-amino-5-(trifluoromethoxy)phenyl]disulfanyl}-4-(trifluoromethoxy)aniline (IIb-2) after flash chromatography (100-200 mesh size silica gel, 10% ethyl acetate in hexane) was 0.35 g.

Intermediate IIb-1. 2-[(2-amino-4-chloro-5-methoxyphenyl)disulfanyl]-5-chloro-4-methoxyaniline

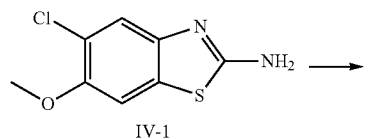

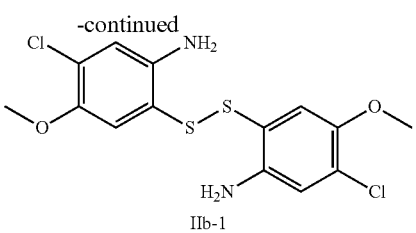

IV-1:

3-Chloro-p-Anisidine (2 g, 12.7 mmol) and potassium thiocyanate (3.8 g, 50.8 mmol) was solved in acetic acid (15 ml). The mixture was stirred at RT for 30 minutes and cooled in an ice bath to 15° C. Bromine (0.65 ml, 12.7 mmol) in acetic acid (5 ml) was added dropwise. Ice bath was removed and the resulting mixture was stirred at RT for 3.5 hours. The reaction mixture was filtered and the solid material was collected. The solid material was mixed with water (15 ml). The mixture was vigorously stirred and 25% NaOH (10 ml) was added. The mixture was filtered and the solid powder dried under vacuo. Yield of 5-chloro-6-methoxy-1,3-benzothiazol-2-amine (IIb-1) was 1.6 g.

IIb-1:

2-[(2-amino-4-chloro-5-methoxyphenyl)disulfanyl]-5-chloro-4-methoxyaniline was prepared according to the method for 2-{[2-amino-5-(trifluoromethoxy)phenyl]disulfanyl}-4-(trifluoromethoxy)aniline (IIb-2). 0.8 g (3.7 mmol) of 5-chloro-6-methoxy-1,3-benzothiazol-2-amine (IV-1) yielded after flash chromatography (100-200 mesh size silica gel, 10-15% ethyl acetate in hexane) 0.61 g of 2-[(2-amino-4-chloro-5-methoxyphenyl)disulfanyl]-5-chloro-4-methoxyaniline (IIb-1).

Intermediate IIb-3. 5,5'-disulfanediylbis(2-chloro-N1,N1-dimethylbenzene-1,4-diamine)

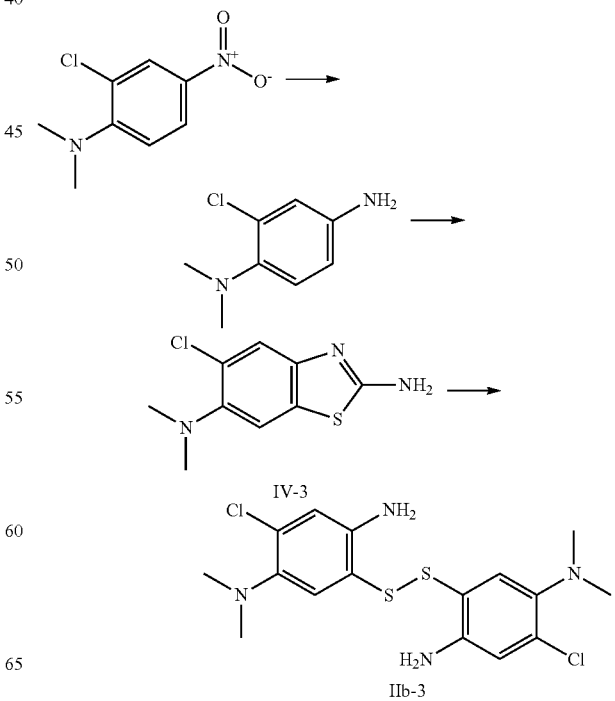

2-Chloro-4-nitroaniline (1.5 g, 8.6 mmol) was dissolved in formic acid (20 ml). The mixture was cooled to 0° C. in an ice bath and NaBH₄ (1.31 g, 34.7 mmol) was added portion wise. During the addition, the temperature was not allowed to rise above 5° C. After addition was complete, the mixture was allowed to warm to RT and stirred at RT for 2 hours. After completion of the reaction, the mixture was poured into ice water. Aqueous NH₄Cl solution was added to quench unreacted NaBH₄. The mixture was neutralized with aqueous NaHCO₃ and extracted with ethyl acetate. The organic layer was dried over sodium sulphate and concentrated under reduced pressure. The yield of 2-chloro-N,N-dimethyl-4-nitroaniline after flash chromatography (100-200 mesh size silica gel, 2% ethyl acetate in hexane) was 1.54 g.

2-chloro-N,N-dimethyl-4-nitroaniline (1.54 g, 7.6 mmol) was dissolved in methanol (30 ml). The solution was purged with N₂-gas. Platinum oxide (0.154 g, 0.68 mmol) was added under nitrogen atmosphere. The reaction assembly was made saturated with H₂-gas and stirred at RT for 2 hours under hydrogen atmosphere. After reaction was completed, the mixture was filtered through celite pad. The filtrate was collected and concentrated under reduced pressure. The yield of 2-chloro-N1,N1-dimethylbenzene-1,4-diamine after flash chromatography (100-200 mesh size silica gel, 10% ethyl acetate in hexane) was 1.1 g.

IV-3:

2-chloro-1-N,1-N-dimethylbenzene-1,4-diamine (0.5 g, 2.93 mmol) and potassium thiocyanate (1.13 g, 11.7 mmol) was solved in acetic acid (25 ml). Bromine (0.15 ml, 2.93 mmol) in acetic acid (5 ml) was added dropwise. The resulting mixture was stirred at RT for 16 hours. After completion of the reaction, the reaction mixture was poured into ice water and neutralized with aqueous ammonia. The aqueous phase was extracted with ethyl acetate. The organic phase dried over sodium sulphate and concentrated under reduced pressure. The residue was triturated with hexane and filtered. The solid was collected and dried under vacuo. The yield of 5-chloro-N6,N6-dimethylbenzo[d]thiazole-2,6-diamine (IV-3) was 0.65 g.

IIb-3:

5-chloro-N6,N6-dimethylbenzo[d]thiazole-2,6-diamine (IV-3) (0.65 g, 2.86 mmol) was suspended with 25% aqueous KOH (50 ml) solution. The mixture was heated at 120° C. for 16 hours. After completion of the reaction the mixture was cooled to RT and poured into ice water. The mixture was neutralized with 50% HCl solution and extracted with ethyl acetate. Organic layer was separated, dried over sodium sulphate and concentrated under reduced pressure. The residue was triturated in n-pentane to obtain yellow colored solid compound. The solids were collected by filtration and dried under vacuo. The yield of 5,5'-disulfanediylbis(2-chloro-N1,N1-dimethylbenzene-1,4-diamine) (IIb-3) was 0.4 g.

Intermediate IIb-4. 2-[(2-amino-5-methoxyphenyl)disulfanyl]-4-methoxyaniline

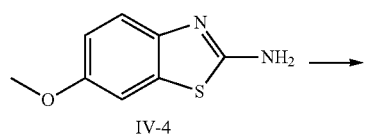

IV-4

-continued

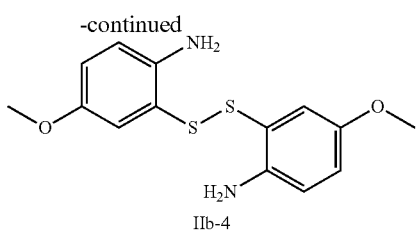

IIb-4

IV-4:

p-Anisidine (2 g, 16.2 mmol) and potassium thiocyanate (6.29 g, 64.8 mmol) was solved in acetic acid (30 ml). Bromine (0.83 ml, 16.2 mmol) in acetic acid (5 ml) was added dropwise. The resulting mixture was stirred at RT for 16 hours. After completion of the reaction, the reaction mixture was poured into ice water and neutralized with aqueous ammonia. The aqueous phase was extracted with ethyl acetate. The organic phase was washed with water and brine, dried over sodium sulphate and concentrated under reduced pressure. Yield of 6-methoxy-1,3-benzothiazol-2-amine after flash chromatography (100-200 mesh size silica gel, 25-30% ethyl acetate in hexane) was 2.3 g.

IIb-4:

6-methoxy-1,3-benzothiazol-2-amine (IV-4) (1.2 g, 6.6 mmol) was suspended with 25% aqueous NaOH (30 ml) solution. The mixture was heated at 100° C. for 16 hours. About 50% of the starting material remained unreacted and the mixture was further stirred at 150° C. for 16 hours. After completion of the reaction the mixture was cooled to RT and poured into ice water. The mixture was neutralized with 6N HCl solution and extracted with ethyl acetate. Organic layer was separated, dried over sodium sulphate and concentrated under reduced pressure. The yield of 2-[(2-amino-5-methoxyphenyl)disulfanyl]-4-methoxyaniline (IIb-4) after flash chromatography (100-200 mesh size silica gel, 10% ethyl acetate in hexane) was 0.81 g.

Intermediate IIb-33.
3-Amino-6-bromopyrazine-2-thiol

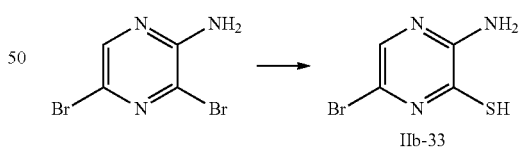

KOH (1.08 g, 19.7 mmol) was added to the solution 2-amino-3,5-dibromopyrazine (0.5 g, 1.97 mmol) in Methanol (6 ml). H₂S gas (prepared from 5.0 g of FeS and 10 ml of HCl) was purged to the mixture for 1 hour and the resulting mixture was refluxed for 3 hours. After completion of the reaction the mixture was cooled and evaporated to dryness under reduced pressure. Water (20 ml) was added and the mixture neutralized with diluted HCl solution and extracted with ethyl acetate. The organic phase was washed with brine, dried over sodium sulphate and concentrated under reduced pressure. Yield was 0.15 g.

Intermediate IIb-36.
3-amino-6-methoxypyrazine-2-thiol

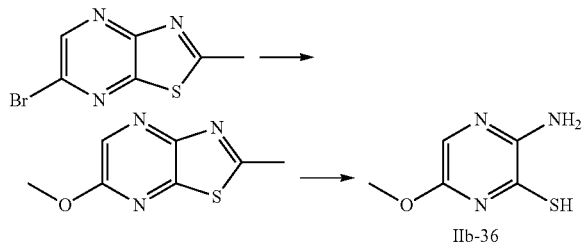

3-Amino-6-bromopyrazine-2-thiol (IIb-33) (0.3 g, 1.46 mmol) and acetic anhydride (10 ml) was placed in an sealed tube and heated at 150° C. for 18 hours. After cooling to the RT the mixture was evaporated under reduced pressure. The yield of 6-bromo-2-methyl-[1,3]thiazolo[4,5-b]pyrazine was 0.3 g.

Na-metal (80 mg, 3.49 mmol) was dissolved in methanol (10 ml). 6-Bromo-2-methyl-[1,3]thiazolo[4,5-b]pyrazine (0.3 g, 1.75 mmol) was added and the resulting mixture was refluxed for 6 hours. After cooling to the RT the solvent was removed by evaporation. Water was added and the resulting mixture was extracted with ethyl acetate. The organic phase was washed with water, dried over sodium sulphate and evaporated under reduced pressure. The yield of 6-methoxy-2-methyl-[1,3]thiazolo[4,5-b]pyrazine was 60 mg.

IIb-36:

6-Methoxy-2-methyl-[1,3]thiazolo[4,5-b]pyrazine (60 mg, 0.33 mmol) was dissolved in methanol (6 ml). NaOH (2M, 1 ml) was added and the resulting mixture was refluxed for 16 hours. Solvent was removed by evaporation. Water was added and the pH was adjusted to 6 using diluted aqueous HCl solution. The mixture was extracted with ethyl acetate. The organic phase was dried over sodium sulphate and concentrated under reduced pressure. The yield of 3-amino-6-methoxypyrazine-2-thiol was 50 mg.

Intermediate IIb-79. 2-[(2-amino-4-chloro-5-trifluoromethoxyphenyl)disulfanyl]-5-chloro-4-trifluoromethoxyaniline

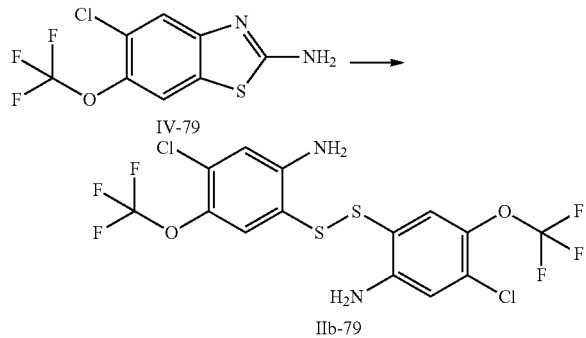

Intermediate IIb-79 was prepared according to the method described for the intermediate IIb-2. 3-Chloro-4-trifluoromethoxyaniline was used as a starting material.

Intermediate IIb-91.
5-amino-2-chloropyrimidine-4-thiol

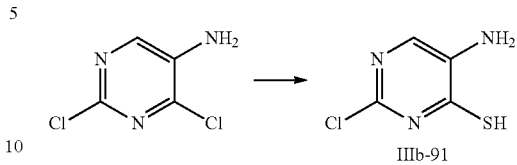

2,4-Dichloropyrimidin-5-amine (0.1 g, 0.61 mmol) and NaSH (0.1 g, 1.82 mmol) was added to DMF (2 ml) and the resulting mixture was stirred at RT for 16 hours. Water was added, pH was adjusted between 6 to 7 with acetic acid and the mixture was extracted with ethyl acetate. The organic layer was washed with water and brine, dried over sodium sulphate and concentrated under reduced pressure. The yield was 0.1 g.

Intermediate IIb-92.
5-amino-2-chloro-6-methoxypyrimidine-4-thiol

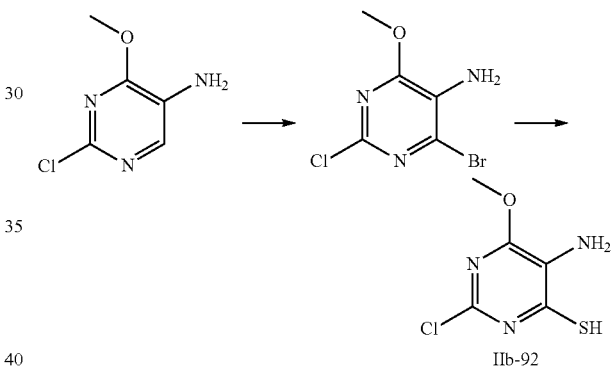

A mixture of 2,4-dichloropyrimidin-5-amine (0.5 g, 3.04 mmol), sodium methoxide (0.66 g, 12.19 mmol) and methanol (10 ml) was refluxed for 16 hours. The solvent was removed under reduced pressure. Water was added and the aqueous phase was extracted with ethyl acetate. The organic phase was washed with water and brine, dried over sodium sulphate and concentrated under reduced pressure. The yield of 2-chloro-4-methoxypyrimidin-5-amine after flash chromatography (100-200 mesh size silica gel, 20-25% ethyl acetate in hexane) was 0.35 g.

N-Bromosuccinimide (67 mg, 0.37 mmol) was added to a solution of 2-chloro-4-methoxypyrimidin-5-amine (50 mg, 0.31 mmol) in chloroform (2 ml) and the resulting mixture was stirred at RT for 3 hours. Water was added and the mixture extracted with chloroform. The organic phase was washed with water and brine, dried over sodium sulphate and concentrated under reduced pressure. The yield of 4-bromo-2-chloro-6-methoxypyrimidin-5-amine was 60 mg.

IIb-92:

5-amino-2-chloro-6-methoxypyrimidine-4-thiol was prepared according to the same method described for 5-amino-2-chloropyrimidine-4-thiol (IIb-91). The crude material was used without further flash chromatography purifications to the preparation of final compounds.

Intermediate III-15.
9-oxa-1-azaspiro[5.5]undecane-2,4-dione

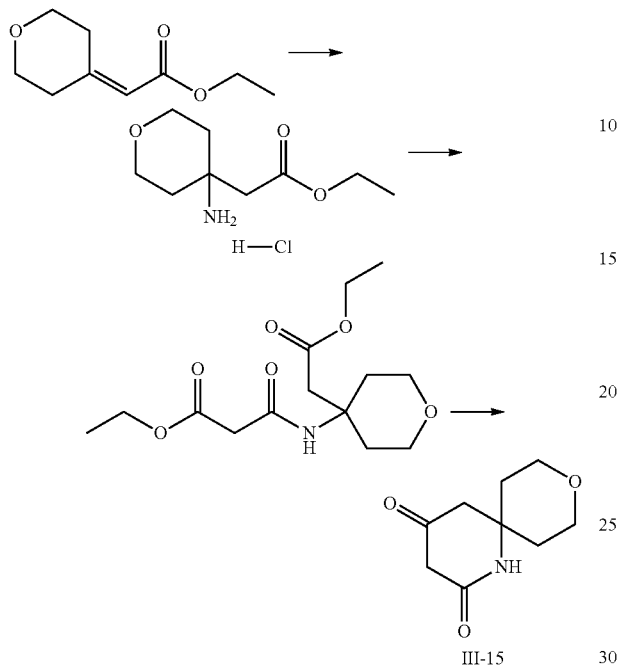

III-15

Ethyl 2-(triphenylphosphoranylidene)acetate (3.90 g, 11.18 mmol) was added to the mixture of oxan-4-one (1.0 g, 9.98 mmol) in acetonitrile (10 ml). The resulting mixture was refluxed for 16 hours. After completion of the reaction, the mixture was cooled and concentrated. Water was added and the mixture was extracted with ethyl acetate. The organic phase was washed with brine, dried over sodium sulphate and concentrated under reduced pressure. The yield of ethyl 2-(oxan-4-ylidene)acetate after flash chromatography (100-200 mesh size silica gel, 10% ethyl acetate in hexane) was 1.0 g.

Liquid ammonia (5 ml) condensed ammonia gas was added to a stirred solution of ethyl 2-(oxan-4-ylidene)acetate (1.0 g, 5.88 mmol) in ethanol (10 ml) in autoclave. The mixture was heated at 90° C. for 24 hours. Reaction was stopped and the autoclave cooled to −78° C. and the mixture was removed. The mixture was allowed to warm to RT and N2-gas was bubbled for 30 minutes into the reaction mixture to remove the excess of the ammonia gas. The reaction mixture was made acidic by purging HCl-gas at 0° C. and the solvent was removed under reduced pressure. The residue was washed with n-pentane and the compound was dried under reduced pressure. The yield of ethyl 2-(4-aminooxan-4-yl)acetate hydrochloride was 1.1 g.

Triethyl amine (9.36 ml, 67.26 mmol) was slowly added to a stirred mixture of ethyl 2-(4-aminooxan-4-yl)acetate hydrochloride (3.0 g, 13.45 mmol) in dichloromethane (60 ml). Ethyl malonylchloride (1.9 ml, 14.79 mmol) was added dropwise at 0° C. and the resulting mixture was allowed to warm up to RT and stirred at RT for 12 hours. After reaction was complete water was added. Organic phase was separated and the aqueous phase extracted with dichloromethane. The combined organic phases were washed with brine, dried over sodium sulphate and concentrated under reduced pressure. The yield of ethyl 2-{[4-(2-ethoxy-2-oxoethyl) oxan-4-yl]carbamoyl}acetate after flash chromatography (100-200 mesh size silica gel, 20% ethyl acetate in hexane) was 1.2 g.

III-15:

Ethyl 2-{[4-(2-ethoxy-2-oxoethyl)oxan-4-yl] carbamoyl}acetate (1.2 g, 3.98 mmol) in toluene (10 ml) was slowly added to the mixture of freshly made sodium ethoxide (prepared in-situ using sodium-metal 0.137 g, 5.98 mmol) in ethanol (10 ml) at 0° C. The resulting mixture was heated up and refluxed for 2 hours. After cooling to RT, water was added and the aqueous phase made acidic with diluted aqueous HCl solution. The mixture was extracted with dichloromethane. The organic phase was separated, dried over sodium sulphate and concentrated under reduced pressure. The residue was mixed with acetonitrile (10 ml) containing 1% of water and refluxed for 18 hours. After completion of the reaction confirmed by TLC, the mixture was concentrated under reduced pressure. The yield of 9-oxa-1-azaspiro[5.5]undecane-2,4-dione (III-15) was 0.45 g.

Intermediate III-1

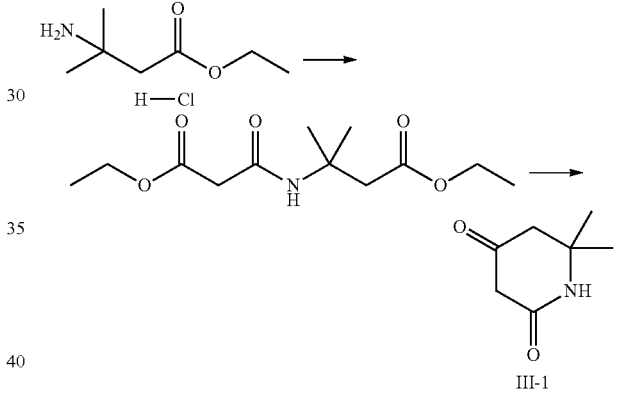

III-1

Ethyl 3-amino-3-methylbutanoate hydrochloride was prepared according to the method described for ethyl 2-(4-aminooxan-4-yl)acetate hydrochloride. Ethyl 3-methylbut-2-enoate (5 g, 29.4 mmol), ethanol (20 ml) and liquid ammonia (20 ml) was used in the reaction. The yield of ethyl 3-amino-3-methylbutanoate hydrochloride was 6.0 g.

Ethyl 3-(3-ethoxy-3-oxopropanamido)-3-methylbutanoate was prepared according to the method described for ethyl 2-{[4-(2-ethoxy-2-oxoethyl)-oxan-4-yl]carbamoyl}acetate. Ethyl 3-amino-3-methylbutanoate hydrochloride (6.0 g, 33.14 mmol), ethyl malonylchloride (4.46 ml, 34.80 mmol), triethylamine (23 ml, 165.1 mmol) and dichloromethane (60 ml) was used. The yield of ethyl 3-(3-ethoxy-3-oxopropanamido)-3-methylbutanoate after flash chromatography (100-200 mesh size silica gel, 20% ethyl acetate in hexane) was 0.9 g.

III-1:

6,6-Dimethylpiperidine-2,4-dione was prepared according to the method described for 9-oxa-1-azaspiro[5.5]undecane-2,4-dione (III-15). Ethyl 3-(3-ethoxy-3-oxopropanamido)-3-methylbutanoate (0.9 g, 3.47 mmol), Na-metal (0.12 g, 5.21 mmol), ethanol (2 ml), toluene (5 ml) and acetonitrile containing 1% of water (5 ml) was used. The yield of 6,6-dimethylpiperidine-2,4-dione (III-1) was 0.3 g.

69

Intermediate III-13. 6,6-diethylpiperidine-2,4-dione

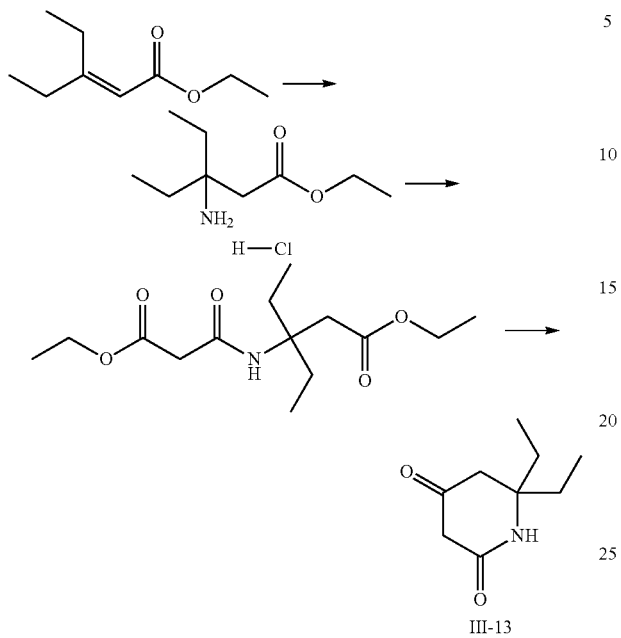

III-13

70

Intermediate III-14. 6-azaspiro[4.5]decane-7,9-dione

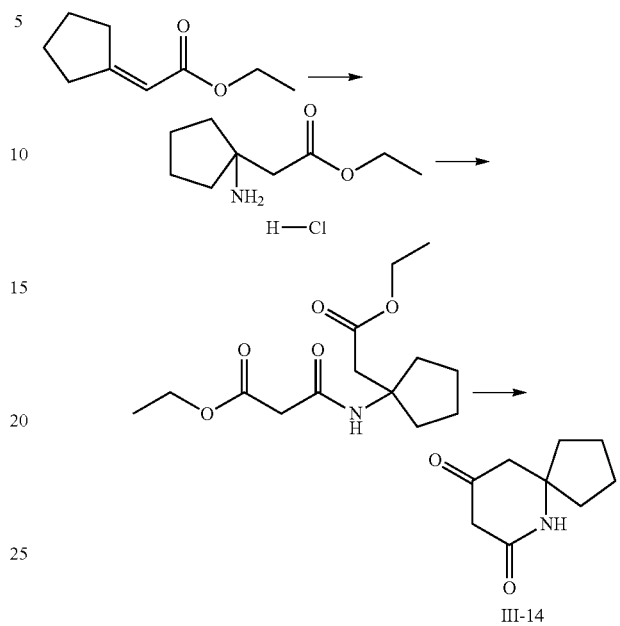

III-14

Ethyl 2-(diethoxyphosphoryl)acetate (5.0 g, 22.3 mmol) in ether (30 ml) was slowly added to the mixture of 60% sodium hydride (0.59 g, 24.5 mmol) in ether (20 ml) at 0° C. The mixture was allowed to warm up to RT and stirred for 1 hour. Pentan-3-one (2.6 ml, 24.5 mmol) was slowly added in ether (20 ml) and the resulting mixture was refluxed for 18 hours. The mixture was diluted with ether and filtered through celite pad. The filtrate was washed with 1N NaOH solution and brine, dried over sodium sulphate and concentrated under reduced pressure. The yield of ethyl 3-ethyl-pent-2-enoate after flash chromatography (100-200 mesh size silica gel, 5% ethyl acetate in hexane) was 2.5 g.

Ethyl 3-amino-3-ethylpentanoate hydrochloride was prepared according to the method described for ethyl 2-(4-aminooxan-4-yl)acetate hydrochloride. Ethyl 3-ethylpent-2-enoate (2.5 g, 16.0 mmol), ethanol (10 ml) and liquid ammonia (10 ml) was used in the reaction. The yield of ethyl 3-amino-3-ethylpentanoate hydrochloride was 3.0 g.

Ethyl 3-(3-ethoxy-3-oxopropanamido)-3-ethylpentanoate was prepared according to the method described for ethyl 2-{[4-(2-ethoxy-2-oxoethyl)oxan-4-yl]carbamoyl}acetate. Ethyl 3-amino-3-ethylpentanoate hydrochloride (3.0 g, 14.38 mmol), ethyl malonylchloride (1.93 ml, 15.07 mmol), triethylamine (10 ml, 71.7 mmol) and dichloromethane (50 ml) was used. The yield of ethyl 3-(3-ethoxy-3-oxopropanamido)-3-ethylpentanoate after flash chromatography (100-200 mesh size silica gel, 20% ethyl acetate in hexane) was 2.5 g.

III-13:

6,6-diethylpiperidine-2,4-dione was prepared according to the method described for 9-oxa-1-azaspiro[5.5]undecane-2,4-dione (III-15). Ethyl 3-(3-ethoxy-3-oxopropanamido)-3-ethylpentanoate (3.0 g, 10.45 mmol), Na-metal (0.36 g, 15.67 mmol), toluene (5 ml) and acetonitrile containing 1% of water (20 ml) was used. The yield of 6,6-diethylpiperidine-2,4-dione (III-13) was 0.2 g.

Ethyl 2-(diethoxyphosphoryl)acetate (5.86 g, 28.15 mmol) was slowly added to the mixture of 60% sodium hydride (1.05 g, 28.15 mmol) in THF (20 ml) at 0° C. The mixture was allowed to warm up to RT and stirred for 1 hour. Cyclopentanone (2.1 ml, 23.77 mmol) was slowly added in THF (10 ml) and the resulting mixture was stirred at RT for 2 hours. Water was added and the mixture was extracted with ethyl acetate. The organic phase was washed with water and brine, dried over sodium sulphate and concentrated under reduced pressure. The yield of ethyl 2-[cyclopentylidene]acetate after flash chromatography (100-200 mesh size silica gel, 5% ethyl acetate in hexane) was 3.0 g.

Ethyl 2-(1-aminocyclopentyl)acetate hydrochloride was prepared according to the method described for ethyl 2-(4-aminooxan-4-yl)acetate hydrochloride. Ethyl 2-[cyclopentylidene]acetate (3.0 g, 19.98 mmol), ethanol (15 ml) and liquid ammonia (15 ml) was used in the reaction. The yield of ethyl 2-(1-aminocyclopentyl)acetate hydrochloride was 1.3 g.

Ethyl 2-{[1-(2-ethoxy-2-oxoethyl)cyclopentyl]carbamoyl}acetate was prepared according to the method described for ethyl 2-{[4-(2-ethoxy-2-oxo-ethyl)oxan-4-yl]carbamoyl}acetate. Ethyl 2-(1-aminocyclopentyl)acetate hydrochloride (2.5 g, 12.0 mmol), ethyl malonylchloride (1.7 ml, 13.28 mmol), triethylamine (8.4 ml, 60.38 mmol) and dichloromethane (50 ml) was used. The yield of ethyl 2-{[1-(2-ethoxy-2-oxoethyl)cyclopentyl]carbamoyl}acetate after flash chromatography (100-200 mesh size silica gel, 20% ethyl acetate in hexane) was 1.3 g.

III-14:

6-Azaspiro[4.5]decane-7,9-dione was prepared according to the method described for 9-oxa-1-azaspiro[5.5]undecane-2,4-dione (III-15). Ethyl 2-{[1-(2-ethoxy-2-oxoethyl)cyclopentyl]carbamoyl}acetate (1.3 g, 4.56 mmol), Na-metal (0.16 g, 6.96 mmol), ethanol (10 ml), toluene (10 ml) and acetonitrile containing 1% of water (10 ml) was used. The yield of 6-azaspiro[4.5]decane-7,9-dione (III-14) was 0.7 g.

Intermediate III-16.
1-ethyl-6,6-dimethylpiperidine-2,4-dione

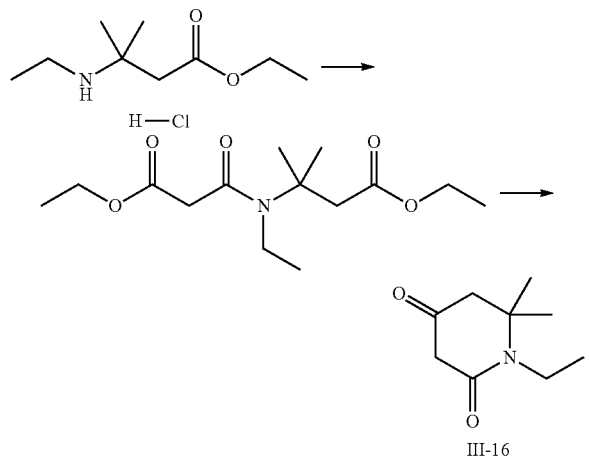

Ethyl 3-methylbut-2-enoate (0.5 g, 3.9 mmol), 2M ethylamine in THF (10 ml) and ethanol (10 ml) was placed in autoclave. The mixture was heated at 90° C. for 24 hours. Reaction was stopped and the autoclave cooled to RT and the mixture was removed. N2-gas was bubbled for 30 minutes into the reaction mixture to remove the excess of the ethylamine. The reaction mixture was made acidic by purging HCl-gas at 0° C. and the solvent was removed under reduced pressure. The residue was washed with n-pentane and the compound was dried under reduced pressure. The yield of ethyl 3-(ethylamino)-3-methylbutanoate hydrochloride was 0.6 g.

Ethyl 3-(3-ethoxy-N-ethyl-3-oxopropanamido)-3-methylbutanoate was prepared according to the method described for ethyl 2-{[4-(2-ethoxy-2-oxoethyl)oxan-4-yl]carbamoyl}acetate. Ethyl 3-(ethylamino)-3-methylbutanoate hydrochloride (0.6 g, 3.47 mmol), ethyl malonylchloride (0.46 ml, 3.64 mmol), triethylamine (2.4 ml, 17.34 mmol) and dichloromethane (10 ml) was used. The yield of ethyl 3-(3-ethoxy-N-ethyl-3-oxopropanamido)-3-methylbutanoate was 1.1 g.

III-16:

1-ethyl-6,6-dimethylpiperidine-2,4-dione was prepared according to the method described for 9-oxa-1-azaspiro[5.5]undecane-2,4-dione (III-15). Ethyl 3-(3-ethoxy-N-ethyl-3-oxopropanamido)-3-methylbutanoate (0.6 g, 2.09 mmol), Na-metal (0.072 g, 3.13 mmol), ethanol (5 ml), toluene (10 ml) and acetonitrile containing 1% of water (5 ml) was used. The yield of 1-ethyl-6,6-dimethylpiperidine-2,4-dione (III-16) was 50 mg.

Intermediate III-17.
1-ethyl-9-oxa-1-azaspiro[5.5]undecane-2,4-dione

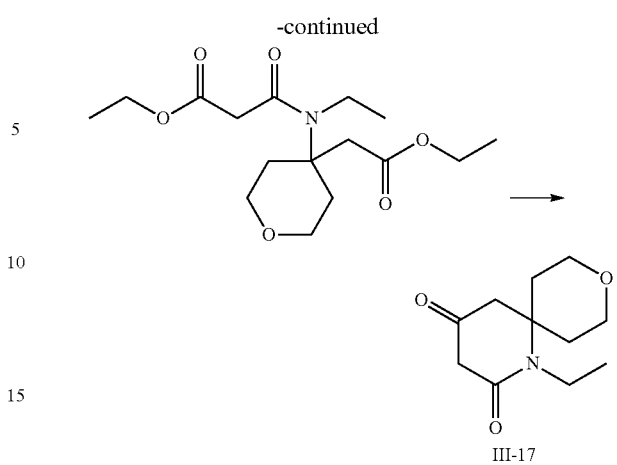

Ethyl 2-[4-(ethylamino)oxan-4-yl]acetate hydrochloride was prepared according to the method described for ethyl 3-(ethylamino)-3-methylbutanoate hydrochloride. Ethyl 2-(oxan-4-ylidene)acetate (2.0 g, 11.76 mmol), 2M ethylamine in THF (30 ml) and ethanol (20 ml) was used. The yield of ethyl 2-[4-(ethylamino)oxan-4-yl]acetate hydrochloride was 0.9 g.

Ethyl 2-{[4-(2-ethoxy-2-oxoethyl)oxan-4-yl](ethyl)carbamoyl}acetate was prepared according to the method described for ethyl 2-{[4-(2-ethoxy-2-oxoethyl)oxan-4-yl]carbamoyl}acetate. Ethyl 2-[4-(ethylamino)oxan-4-yl]acetate hydrochloride (0.9 g, 3.58 mmol), ethyl malonylchloride (0.5 ml, 3.94 mmol), triethylamine (2.49 ml, 17.92 mmol) and dichloromethane (30 ml) was used. The yield of ethyl 2-{[4-(2-ethoxy-2-oxoethyl)oxan-4-yl](ethyl)carbamoyl}-acetate was 0.45 g.

III-17:

1-ethyl-9-oxa-1-azaspiro[5.5]undecane-2,4-dione was prepared according to the method described for 9-oxa-1-azaspiro[5.5]undecane-2,4-dione (III-15). Ethyl 2-{[4-(2-ethoxy-2-oxoethyl)oxan-4-I](ethyl)carbamoyl}-acetate (0.45 g, 1.37 mmol), Na-metal (47 mg, 2.05 mmol), ethanol (5 ml), toluene (5 ml) and acetonitrile containing 1% of water (10 ml) was used. The yield of 1-ethyl-9-oxa-1-azaspiro[5.5]undecane-2,4-dione (III-17) was 0.15 g.

Intermediate III-29.
1,6,6-triethylpiperidine-2,4-dione

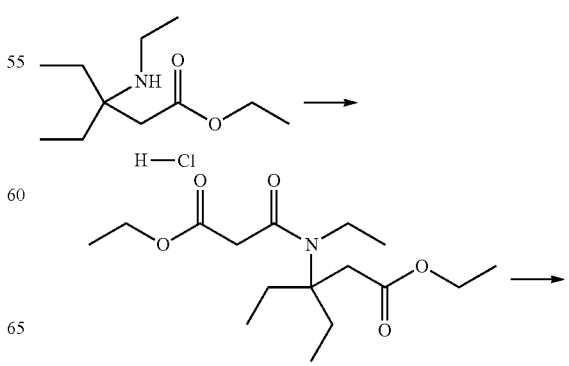

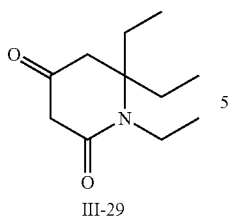

III-29

Ethyl 3-ethylpent-2-enoate (0.5 g, 3.20 mmol), 70% aqueous ethyl amine (10 ml) and ethanol (10 ml) was placed in a seal tube and heated at 90° C. for 72 hours. After cooling to RT, water was added and the mixture was extracted with ethyl acetate. Organic phase was washed with water, dried over sodium sulphate and concentrated under reduced pressure: The yield of ethyl 3-ethylpent-2-enoate after flash chromatography (100-200 mesh size silica gel, 10% methanol in dichloromethane) was 50 mg.

Ethyl 3-(3-ethoxy-N-ethyl-3-oxopropanamido)-3-ethylpentanoate was prepared according to the method described for ethyl 2-{[4-(2-ethoxy-2-oxoethyl)oxan-4-yl]carbamoyl}acetate. ethyl 3-ethyl-3-(ethylamino)pentanoate hydrochloride (50 mg, 0.25 mmol), ethyl malonylchloride (0.035 ml, 0.27 mmol), triethylamine (0.1 ml, 0.74 mmol) and dichloromethane (5 ml) was used. The yield of Ethyl 3-(3-ethoxy-N-ethyl-3-oxopropanamido)-3-ethylpentanoate was 25 mg.

III-29:

1,6,6-triethylpiperidine-2,4-dione was prepared according to the method described for 9-oxa-1-azaspiro[5.5]undecane-2,4-dione (III-15). Ethyl 3-(3-ethoxy-N-ethyl-3-oxopropanamido)-3-ethylpentanoate (50 mg, 0.17 mmol), Na-metal (0.006 g, 0.26 mmol), ethanol (2 ml), toluene (5 ml) and acetonitrile containing 1% of water (5 ml) was used. The yield of 1,6,6-triethylpiperidine-2,4-dione was 30 mg.

Intermediate III-5. Oxane-3,5-dione

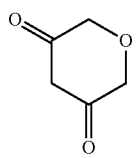

Oxane-3,5-dione (III-5) was prepared according to the method described by Altenbach et al. in Journal of Medicinal Chemistry, 49(23), 6869-6887; 2006

Intermediate III-7. Thiane-3,5-dione

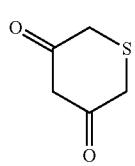

Thiane-3,5-dione (III-7) was prepared according to the method described by Camilleri et al in Journal of the Chemical Society, Perkin Transactions 2: Physical Organic Chemistry (1972-1999), (6), 833-6; 1985.

Intermediate III-9. Azepane-2,4-dione

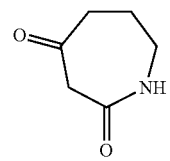

Azepane-2,4-dione (III-9) was prepared using the method described by Coleman et al in U.S. Pat. Appl. Publ., 20100234588, 16 Sep. 2010.

Intermediate III-18. 5,5-dimethylpiperidine-2,4-dione

III-18

Ethyl 2-cyanoacetate (4.7 ml, 44.24 mmol) was added slowly to the stirred mixture of 60% NaH (5.3 g, 132 mmol) in dry THF at 0° C. The resulting mixture was stirred at 0° C. for 30 minutes. Methyl iodide (6.89 ml, 110.61 mmol) was slowly added at 0° and the reaction mixture was allowed to warm up to RT. Stirring was continued at RT for 18 hours. After completion of the reaction, water was added and the mixture was extracted with ethyl acetate. Organic phase was separated, dried over sodium sulphate and concentrated under reduced pressure. The yield of ethyl 2-cyano-2,2-dimethylacetate was 2.5 g.

Ethyl 2-cyano-2,2-dimethylacetate (2.0 g, 14.18 mmol) was dissolved in methanol (20 ml) and Raney Nickel (0.4 g) was added. The system was purged with $N_2$-gas and evacuated. The reaction assembly was made saturated with $H_2$-gas and stirred at RT for 3 hours under hydrogen atmosphere. After reaction was completed, the mixture was filtered through celite pad. The filtrate was collected and concentrated under reduced pressure. The yield of ethyl 3-amino-2,2-dimethylpropanoate was 1.4 g.

Ethyl 3-(3-ethoxy-3-oxopropanamido)-2,2-dimethylpropanoate was prepared according to the method described for ethyl 2-{[4-(2-ethoxy-2-oxoethyl)oxan-4-yl]carbamoyl}acetate. Ethyl 3-amino-2,2-dimethylpropanoate (0.7 g, 4.87 mmol), ethyl malonylchloride (0.68 ml, 5.31 mmol), triethylamine (2 ml, 14.48 mmol) and dichloromethane (10 ml) was used. The yield of ethyl 3-(3-ethoxy-3-oxopropanamido)-2,2-dimethylpropanoate was 0.3 g.

III-18:

5,5-Dimethylpiperidine-2,4-dione was prepared according to the method described for 9-oxa-1-azaspiro[5.5]undecane-2,4-dione (III-15). Ethyl 3-(3-ethoxy-3-oxopropanamido)-2,2-dimethylpropanoate (0.3 g, 1.16 mmol), Na-metal (40 mg, 1.74 mmol), ethanol (2 ml), toluene (5 ml) and acetonitrile containing 1% of water (5 ml) was used. The yield of 5,5-dimethylpiperidine-2,4-dione (III-18) was 0.12 g.

Intermediate III-19.
1-ethyl-5,5-dimethylpiperidine-2,4-dione

N-(4-ethoxy-2,2-dimethyl-3-oxobutyl)-N-ethylcarbamate after flash chromatography (100-200 mesh size silica gel, 8% ethyl acetate in hexane) was 0.28 g.

Tert-butyl N-(4-ethoxy-2,2-dimethyl-3-oxobutyl)-N-ethylcarbamate (0.1 g, 0.36 mmol) was dissolved in dichloromethane. Trifluoroacetic acid (0.14 ml, 10.3 mmol) was added in an ice bath. The resulting mixture was allowed to warm up to RT and stirred for 6 hours. The mixture was concentrated under reduced pressure and the residue was washed with n-pentane. After drying under reduced pressure the yield of 1-ethoxy-3-[(ethylamino)methyl]-3-methylbutan-2-one trifluoroacetic acid salt 0.1 g.

Ethyl 2-[(4-ethoxy-2,2-dimethyl-3-oxobutyl)(ethyl)carbamoyl]acetate was prepared according to the method described for ethyl 2-{[4-(2-ethoxy-2-oxoethyl)oxan-4-yl]carbamoyl}acetate. 1-Ethoxy-3-[(ethylamino)methyl]-3-methylbutan-2-one trifluoroacetic acid salt (0.1 g, 0.57 mmol), ethyl malonylchloride (0.081 ml, 0.64 mmol), triethylamine (0.24 ml, 1.73 mmol) and dichloromethane (5 ml) was used. The yield of ethyl 2-[(4-ethoxy-2,2-dimethyl-3-oxobutyl)(ethyl)carbamoyl]acetate was 50 mg.

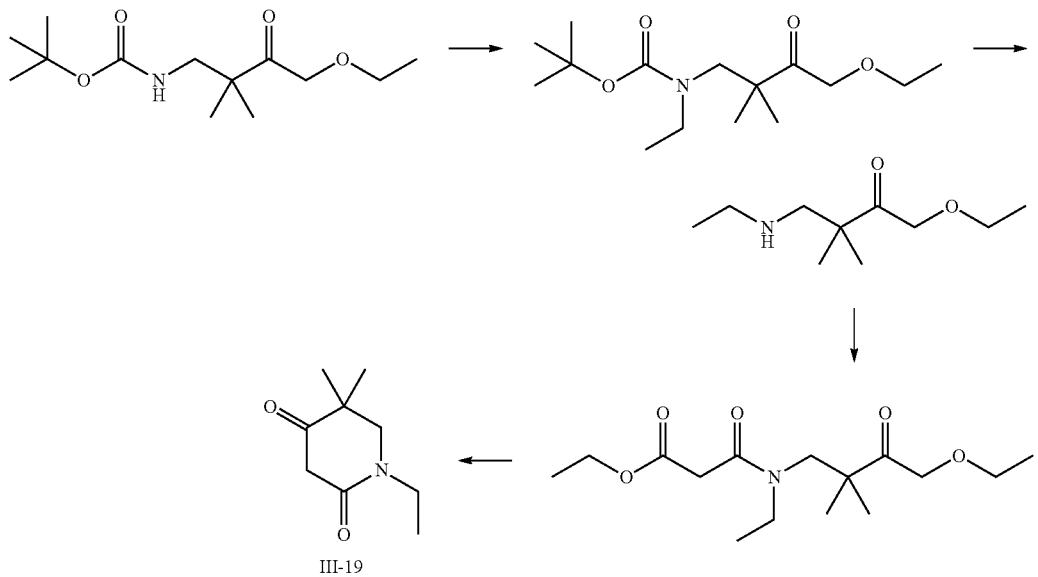

III-19

Ethyl 2-cyano-2,2-dimethylacetate (1.0 g, 7.09 mmol) was dissolved in methanol (10 ml) and Pd on C (0.1 g) and Boc-anhydride (1.85 g, 8.59 mmol) was added. The system was purged with $N_2$-gas and evacuated. The reaction assembly was made saturated with $H_2$-gas and stirred at RT for 24 hours under hydrogen atmosphere. After reaction was completed, the mixture was filtered through celite pad. The filtrate was collected and concentrated under reduced pressure. The yield of tert-butyl N-(4-ethoxy-2,2-dimethyl-3-oxobutyl)-carbamate after flash chromatography (100-200 mesh size silica gel, 10% ethyl acetate in hexane) was 0.45 g.

60% Sodium hydride (0.088 g, 2.70 mmol) was added to a solution of tert-butyl N-(4-ethoxy-2,2-dimethyl-3-oxobutyl)carbamate (0.45 g, 1.83 mmol) in dry dimethylformamide (5 ml). The mixture was stirred for 10 minutes at 0° C. and ethyl iodide (0.17 ml, 2.44 mmol) was added. The resulting mixture was allowed to warm up to RT and stirred at RT for 18 hours. The mixture was poured in ice water and extracted with ethyl acetate. The organic phase was washed with water and brine, dried over sodium sulphate and concentrated under reduced pressure. The yield of tert-butyl

III-19:

1-Ethyl-5,5-dimethylpiperidine-2,4-dione was prepared according to the method described for 9-oxa-1-azaspiro[5.5]undecane-2,4-dione (III-15). Ethyl 2-[(4-ethoxy-2,2-dimethyl-3-oxobutyl)(ethyl)carbamoyl]acetate (50 mg, 0.17 mmol), Na-metal (6 mg, 0.26 mmol), ethanol (2 ml), toluene (5 ml) and acetonitrile containing 1% of water (5 ml) was used. The yield of 1-ethyl-5,5-dimethylpiperidine-2,4-dione (III-19) was 30 mg.

Intermediate III-20. 7-bromo-4,4-dimethyl-4,5,6,7-tetrahydro-2H-indazol-6-one

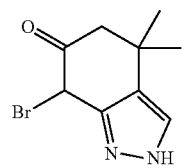

7-bromo-4,4-dimethyl-4,5,6,7-tetrahydro-2H-indazol-6-one (III-20) was prepared according to the method described by Alexander et al. in WO2009071890.

Intermediate III-23.
5,5-dimethyl-5,6,7,8-tetrahydroquinazolin-7-one

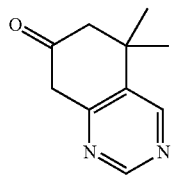

5,5-dimethyl-5,6,7,8-tetrahydroquinazolin-7-one (III-23) was prepared according to the method described by Alexander et al in PCT Int. Appl., 2009071890, 11 Jun. 2009.

Intermediate III-31. 6-Phenylpiperidine-2,4-dione

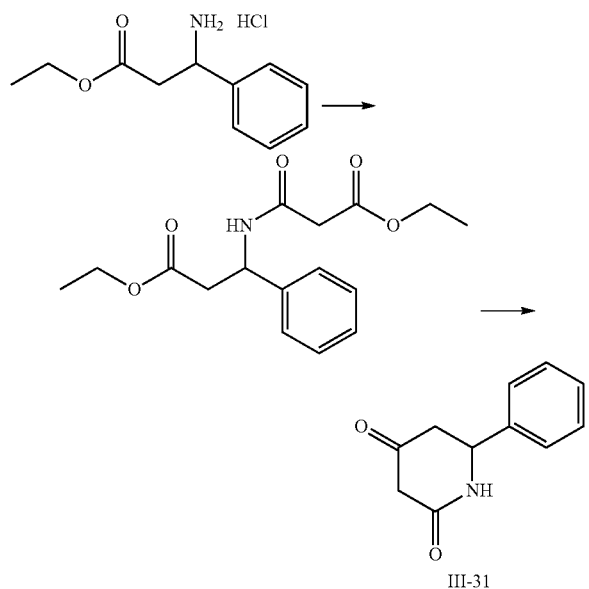

III-31

Ethyl 3-amino-3-phenylpropanoate hydrochloride was prepared according to the method described for ethyl 2-(4-aminooxan-4-yl)acetate hydrochloride. Ethyl 3-phenylprop-2-enoate (3 g, 28.4 mmol), ethanol (20 ml) and liquid ammonia (25 ml) was used in the reaction. The yield of ethyl 3-amino-3-phenylpropanoate hydrochloride was 2.0 g.

Ethyl 3-(3-ethoxy-3-oxopropanamido)-3-phenylpropanoate was prepared according to the method described for ethyl 2-{[4-(2-ethoxy-2-oxoethyl)oxan-4-yl]carbamoyl}acetate. Ethyl 3-amino-3-phenylpropanoate hydrochloride (2.0 g, 10.4 mmol), ethyl malonylchloride (1.46 ml, 11.4 mmol), triethylamine (7.2 ml, 51.8 mmol) and dichloromethane (50 ml) was used. The yield of ethyl 3-(3-ethoxy-3-oxopropanamido)-3-phenylpropanoate after flash chromatography (100-200 mesh size silica gel, 20% ethyl acetate in hexane) was 1.3 g.

III-31:
6-Phenylpiperidine-2,4-dione was prepared according to the method described for 9-oxa-1-azaspiro[5.5]undecane-2,4-dione (III-15). Ethyl 3-(3-ethoxy-3-oxopropanamido)-3-phenylpropanoate (1.3 g, 4.28 mmol), Na-metal (0.15 g, 6.35 mmol), ethanol (5 ml), toluene (10 ml) and acetonitrile containing 1% of water (10 ml) was used. The yield of 6-phenylpiperidine-2,4-dione (III-31) was 0.6 g.

Intermediate III-32. 6-Methylpiperidine-2,4-dione

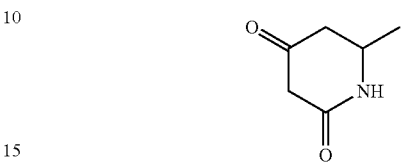

6-methylpiperidine-2,4-dione (III-32) was prepared according to the same method as described for 6-phenylpiperidine-2,4-dione (III-31). Ethyl but-2-enoate was used as a starting material.

Intermediate III-41.
1-Acetoamino-6,6-dimethylpiperidine-2,4-dione

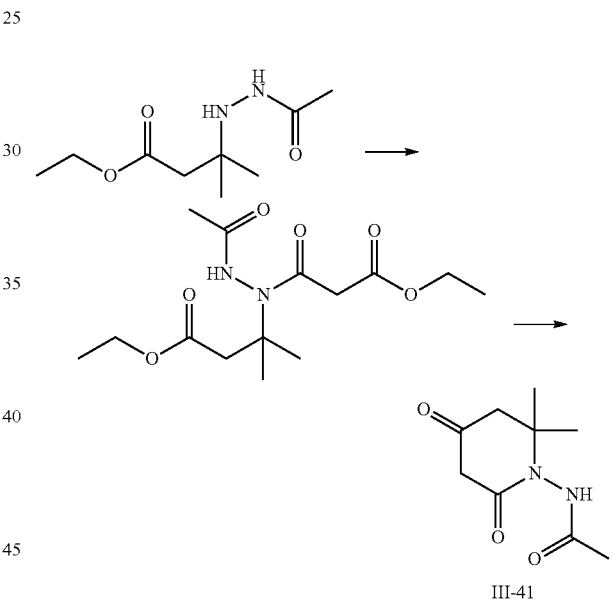

III-41

Ethyl 3-methylbut-2-enoate (5 g, 39.1 mmol) and acetohydrazine (7.2 g, 97.6 mmol) was heated at 100° C. in a sealed tube for 48 hours. After cooling to RT, water was added and the mixture extracted with dichloromethane. The organic phase was dried over sodiumsulphate and concentrated under reduced pressure. The yield of ethyl 3-acetohydrazido-3-methylbutanoate after flash chromatography (100-200 mesh size silica gel, 4% methanol in dichloromethane) was 1.5 g.

Ethyl 3-[N'-(3-ethoxy-3-oxopropanoyl)acetohydrazido]-3-methylbutanoate was prepared according to the method described for ethyl 2-{[4-(2-ethoxy-2-oxoethyl)oxan-4-yl]carbamoyl}acetate. Ethyl 3-acetohydrazido-3-methylbutanoate (1.5 g, 7.42 mmol), ethyl malonylchloride (1.05 ml, 8.16 mmol), triethylamine (1.55 ml, 11.1 mmol) and dichloromethane (30 ml) was used. The yield of ethyl 3-[N'-(3-ethoxy-3-oxopropanoyl)acetohydrazido]-3-methylbutanoate after flash chromatography (100-200 mesh size silica gel, 20% ethyl acetate in hexane) was 1.4 g.

III-41:

1-acetoamino-6,6-dimethylpiperidine-2,4-dione was prepared according to the method described for 9-oxa-1-azaspiro[5.5]undecane-2,4-dione (III-15). Ethyl 3-[N'-(3-ethoxy-3-oxopropanoyl)acetohydrazido]-3-methylbutanoate (50 mg, 0.16 mmol), Na-metal (6 mg, 0.22 mmol), ethanol (1 ml), toluene (2 ml) and acetonitrile containing 1% of water (2 ml) was used. The yield of 1-acetoamino-6,6-dimethylpiperidine-2,4-dione (III-41) was 12 mg.

Intermediate III-42.
1-Acetoamino-6-methylpiperidine-2,4-dione

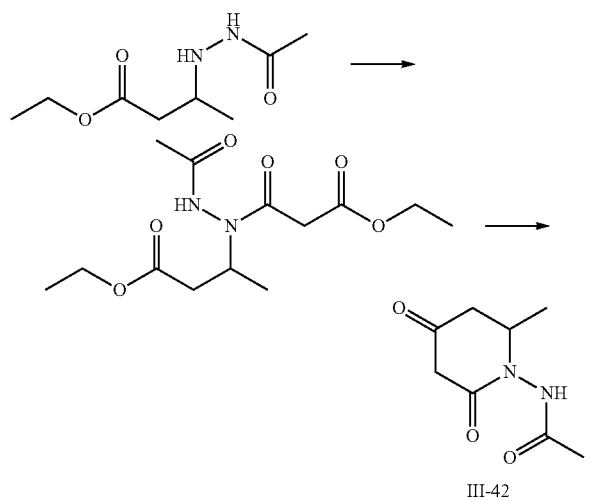

1-acetoamino-6-methylpiperidine-2,4-dione (III-42) was prepared according to the same method as described for 1-acetoamino-6,6-dimethylpiperidine-2,4-dione (III-41). Ethyl but-2-enoate was used as a starting material.

Intermediate III-53. 6-Ethylpiperidine-2,4-dione

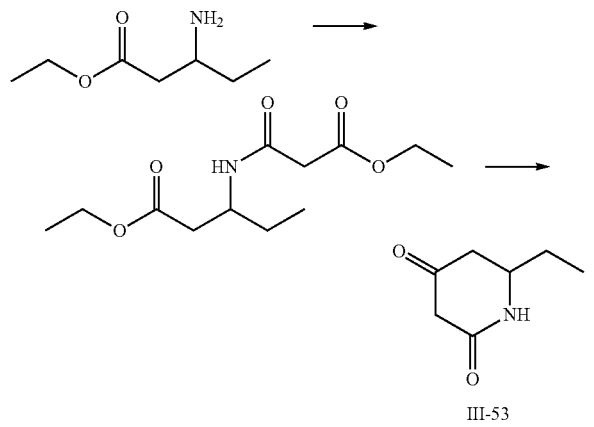

6-ethylpiperidine-2,4-dione (III-53) was prepared according to the same method as described for 6-phenylpiperidine-2,4-dione (III-31). Ethyl pent-2-enoate was used as a starting material.

Intermediate III-56.
6-(pyridin-2-yl)piperidine-2,4-dione

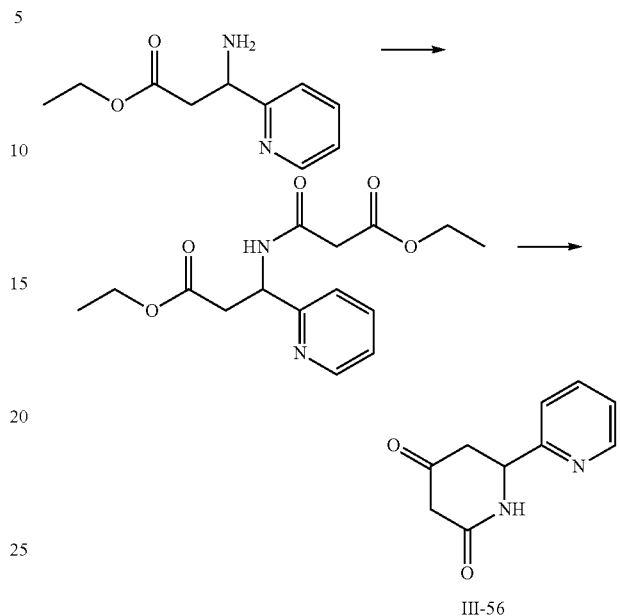

6-(pyridin-2-yl)piperidine-2,4-dione (III-56) was prepared according to the same method as described for 6-phenylpiperidine-2,4-dione (III-31). Ethyl 3-(pyridin-2-yl)prop-2-enoate was used as a starting material.

Intermediate III-62.
4-Azaspiro[2.5]octane-5,7-dione

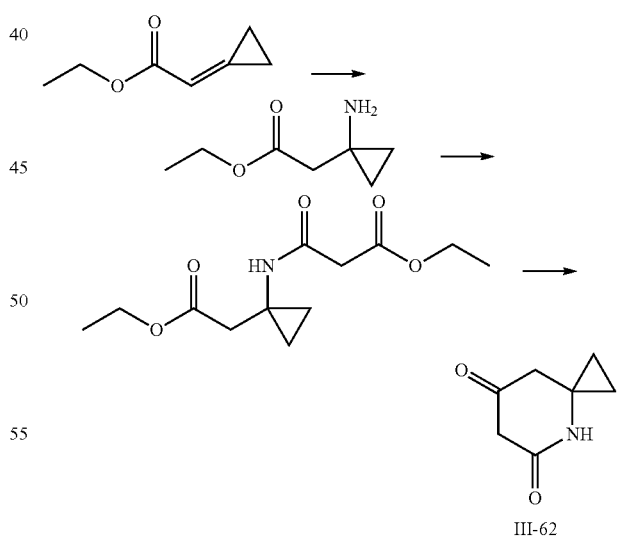

1-ethoxy-1-[(trimethylsilyl)oxy]-cyclopropane (1.7 g, 9.75 mmol) was dissolved in methanol (43 ml) and stirred at room temperature for 17 hours. The solvent was removed under vacuo and the residue dissolved in benzene (16 ml). Benzoic acid (0.24 g, 1.95 mmol) was added and the resulting mixture was refluxed gently while Ethyl 2-(triphenylphosphoranylidene)acetate (3.06 g, 8.78 mmol) in benzene (16 ml) added and the reflux continued for 2 hour after addition was complete. The mixture was cooled and solvent removed under vacuo. The yield of ethyl 2-cyclopropylideneacetate after flash chromatography (100-200 mesh size silica gel, 30% dichloromethane in hexane) was 1.2 g.

4-azaspiro[2.5]octane-5,7-dione (III-62) was prepared according to the same method described for intermediate ethyl 2-(oxan-4-ylidene)acetate in the synthesis of 9-oxa-1-azaspiro[5.5]undecane-2,4-dione (III-15). Ethyl 2-cyclopropylideneacetate was used as a starting material.

Intermediate III-63.
1-Acetamino-6-(pyridin-2-yl)piperidine-2,4-dione

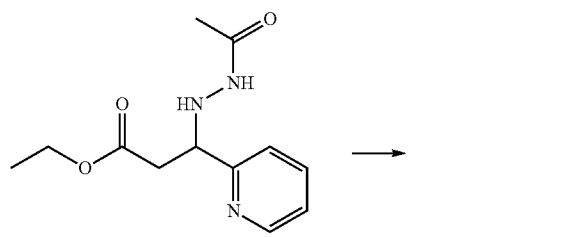

1-acetamino-6-(pyridin-2-yl)piperidine-2,4-dione (III-63) was prepared according to the same method as described for 1-acetoamino-6,6-dimethylpiperidine-2,4-dione (III-41). Ethyl 3-(pyridin-2-yl)prop-2-enoate was used as a starting material.

Intermediate III-66. N-{2,4-dioxo-9-oxa-1-azaspiro[5.5]undecan-1-yl}acetamide

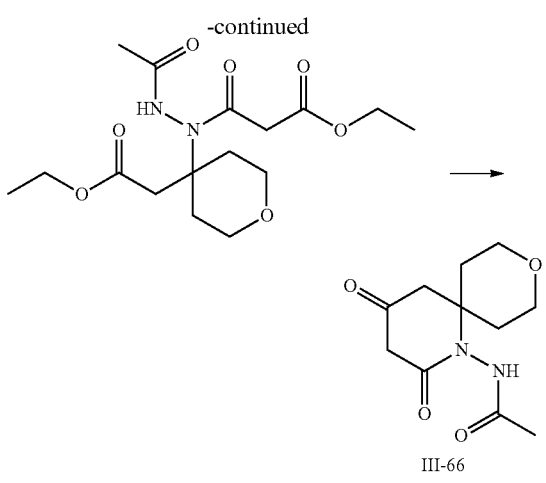

N-{2,4-dioxo-9-oxa-1-azaspiro[5.5]undecan-1-yl}acetamide (III-66) was prepared according to the same method as described for 1-acetoamino-6,6-dimethylpiperidine-2,4-dione (III-41). Ethyl 2-(oxan-4-ylidene)acetate was used as a starting material.

Intermediate III-78.
1-acetamino-6-azaspiro[4.5]decane-7,9-dione

Ethyl 2-[cyclopentylidene]acetate (500 mg, 3.25 mmol) and acetohydrazine (360 mg, 4.87 mmol) was heated at 120° C. in a sealed tube for 24 hours in microwave reactor. After cooling to RT the product was purified using flash chromatography (100-200 mesh size silica gel, 3% methanol in dichloromethane). The yield was 120 mg.

Ethyl 3-{N'-[1-(2-ethoxy-2-oxoethyl)cyclopentyl]acetohydrazido}-3-oxopropanoate was prepared according to the method described for ethyl 2-{[4-(2-ethoxy-2-oxoethyl)oxan-4-yl]carbamoyl}acetate. Ethyl 2-(1-acetohydrazidocyclopentyl)acetate (120 mg, 0.53 mmol), ethyl malonylchloride (0.13 ml, 1.05 mmol), triethylamine (0.22 ml, 1.58 mmol) and dichloromethane (10 ml) was used. The yield of ethyl 3-{N'-[1-(2-ethoxy-2-oxoethyl)cyclopentyl]acetohydrazido}-3-oxopropanoate after flash chromatography (100-200 mesh size silica gel, 2% methanol in dichloromethane) was 120 mg.

III-78:

1-acetamino-6-azaspiro[4.5]decane-7,9-dione was prepared according to the method described for 9-oxa-1-azaspiro[5.5]undecane-2,4-dione (III-15). Ethyl 3-{N'-[1-(2-ethoxy-2-oxoethyl)cyclopentyl]acetohydrazido}-3-oxopropanoate (120 mg, 0.35 mmol), NaOEt (36 mg, 0.53 mmol), ethanol (0.5 ml), toluene (6 ml) and acetonitrile containing 1% of water (6 ml) was used. The yield of 1-acetamino-6-azaspiro[4.5]decane-7,9-dione (III-78) was 55 mg.

Intermediate III-81.
8,8-Dimethyl-4-azaspiro[2.5]octane-5,7-dione

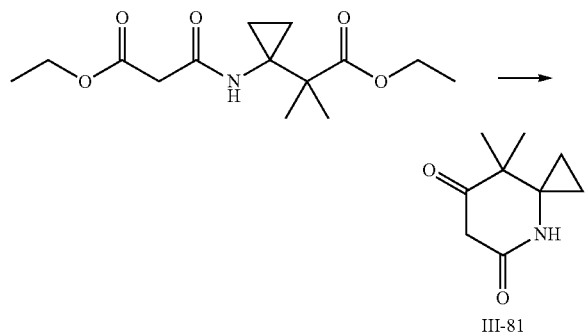

III-81

Ethyl 2-(1-aminocyclopropyl)-2-methylpropanoate was prepared according to the method described by Bertus et al. in Synlett 2003(2), 265-267. Ethyl 2-cyano-2,2-dimethylacetate (preparation described in the synthesis of III-18) was used as a starting material.

Ethyl 2-{[1-(1-ethoxy-2-methyl-1-oxopropan-2-yl)cyclopropyl]carbamoyl}acetate was prepared according to the method described for ethyl 2-{[4-(2-ethoxy-2-oxoethyl)oxan-4-yl]carbamoyl}acetate. Ethyl 2-(1-aminocyclopropyl)-2-methylpropanoate (0.7 g, 4.09 mmol), ethyl malonyl-chloride (0.8 ml, 6.14 mmol), triethylamine (1.7 ml, 12.28 mmol) and dichloromethane (10 ml) was used. The yield of ethyl 2-{[1-(1-ethoxy-2-methyl-1-oxopropan-2-yl)cyclopropyl]carbamoyl}acetate was 0.25 g.

III-81.

8,8-Dimethyl-4-azaspiro[2.5]octane-5,7-dione was prepared according to the method described for 9-oxa-1-azaspiro[5.5]undecane-2,4-dione (III-15). Ethyl 2-{[1-(1-ethoxy-2-methyl-1-oxopropan-2-yl)cyclopropyl]carbamoyl}acetate (0.25 g, 0.88 mmol), NaOEt (90 mg, 1.31 mmol), ethanol (0.5 ml), toluene (5 ml) and acetonitrile containing 1% of water (5 ml) was used. The yield of 8,8-Dimethyl-4-azaspiro[2.5]octane-5,7-dione (III-81) was 0.1 g.

Intermediate III-95. [(4-ethoxy-6,6-dimethyl-2-oxo-cyclohex-3-en-1-yl)methylidene]urea

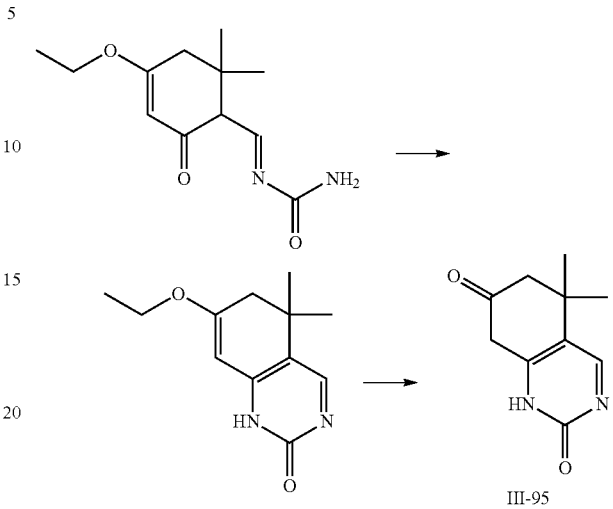

III-95

(CH$_3$)$_3$SiCl (0.56 ml, 4.48 mmol) was slowly added to a stirred mixture of 4-ethoxy-6,6-dimethyl-2-oxocyclohex-3-ene-1-carbaldehyde (prepared according to the method described by Alexander et al in PCT Int. Appl., 2009071890, 11 Jun. 2009; 0.8 g, 4.08 mmol) and urea (0.49 g, 8.16 mmol) in dry DMF (4 ml) at 0° C. The resulting mixture was stirred at 40° C. for 18 hours. After cooling to the RT, water was added. The precipitated solids were filtered, washed with water and n-pentane and dried under reduced pressure. The yield of [(4-ethoxy-6,6-dimethyl-2-oxocyclohex-3-en-1-yl)methylidene]urea was 0.65 g.

[(4-Ethoxy-6,6-dimethyl-2-oxocyclohex-3-en-1-yl)methylidene]urea (0.65 g, 2.13 mmol) was added to a solution of NaOH (0.19 g, 8.19 mmol) in water (5 ml). The resulting mixture was stirred at 70° C. for 16 hours. After cooling to the RT, the pH was adjusted to 2 with conc. HCl. The precipitated solids were filtered, washed with water and n-pentane and dried under reduced pressure. The yield of 7-ethoxy-5,5-dimethyl-1,2,5,6-tetrahydroquinazolin-2-one was 0.48 g.

III-95.

7-Ethoxy-5,5-dimethyl-1,2,5,6-tetrahydroquinazolin-2-one (0.2 g, 0.90 mmol) was mixed with 6M aqueous HCl (4 ml) and ethanol (2 ml). The mixture was stirred at 80° C. for 8 hours. Solvents were removed under reduced pressure. The yield of 5,5-dimethyl-1,2,5,6,7,8-hexahydroquinazoline-2,7-dione was 0.15 g.

Synthesis of Arylthiazine Compounds

Compound 1. 7-chloro-8-methoxy-3,3-dimethyl-3,4-dihydro-2H-benzo[b]-pyrido[4,3-e][1,4]thiazin-1(5H)-one A solution of 2-[(2-amino-4-chloro-5-methoxyphenyl)disulfanyl]-5-chloro-4-methoxyaniline (IIb-1) (0.403 g, 1.06 mmol) and 6,6-dimethylpiperidine-2,4-dione (III-1) (0.302 g, 2.1 mmol) in ethanol (25 ml) containing catalytic amount of triethylamine (5 drops) was refluxed for 16 hours. After completion of the reaction the mixture was concentrated to dryness under reduced pressure. The residue was washed with 5% dichloromethane in pentane and dried under reduced pressure. The yield was 0.24 g.

Compound 2. 3,3-dimethyl-8-(trifluoromethoxy)-3,4-dihydro-2H-benzo[b]-pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.45 g, 1.08 mmol) and 6,6-dimethylpiperidine-2,4-dione (III-1) (0.457 g, 3.24 mmol) in ethanol (25 ml) containing catalytic amount of triethylamine (5 drops) was refluxed for 16 hours. After completion of the reaction the mixture was concentrated to dryness under reduced pressure. The residue was dissolved to the minimum amount of chloroform/methanol. n-Hexane was added and the mixture was stirred for 30 minutes. The solids were collected and dried under reduced pressure. The yield was 0.5 g.

Compound 3. 7-chloro-8-(dimethylamino)-3,3-dimethyl-3,4-dihydro-2H-benzo[b]pyrido[4,3-e][1,4]thiazin-1(5H)-one A solution of 5,5'-disulfanediylbis(2-chloro-N1,N1-dimethylbenzene-1,4-diamine) (IIb-3) (0.213 g, 0.53 mmol) and 6,6-dimethylpiperidine-2,4-dione (III-1) (0.150 g, 1.06 mmol) in ethanol (10 ml) containing catalytic amount of triethylamine (5 drops) was refluxed for 16 hours. After completion of the reaction the mixture was concentrated to dryness under reduced pressure. The residue was washed with 5% dichloromethane in pentane and dried under reduced pressure. The yield was 53 mg.

Compound 4. 8-methoxy-3,3-dimethyl-3,4-dihydro-2H-benzo[b]pyrido-[4,3-e][1,4]thiazin-1(5H)-one A solution of 2-[(2-amino-5-methoxyphenyl)disulfanyl]-4-methoxyaniline (IIb-4) (0.131 g, 0.42 mmol) and 6,6-dimethylpiperidine-2,4-dione (III-1) (0.150 g, 1.06 mmol) in ethanol (15 ml) containing catalytic amount of triethylamine (4 drops) was refluxed for 16 hours. After completion of the reaction the mixture was concentrated to dryness under reduced pressure. The yield after flash chromatography (100-200 mesh size silica gel, 1.5-2% methanol in hexane) was 15 mg.

Compound 5. 7-methoxy-1H,3H-benzo[b]pyrano[3,4-e][1,4]thiazin-4(10H)-one

A solution of 2-[(2-amino-5-methoxyphenyl)disulfanyl]-4-methoxyaniline (IIb-4) (0.337 g, 1.09 mmol) and oxane-3,5-dione (III-5) (0.250 g, 2.19 mmol) in ethanol (7 ml) and triethylamine (0.5 ml) was refluxed for 16 hours. After completion of the reaction the mixture was concentrated to dryness under reduced pressure. The yield after flash chromatography (100-200 mesh size silica gel, 25% ethyl acetate in hexane) was 10 mg.

Compound 6. 7-(trifluoromethoxy)-1H,3H-benzo[b]pyrano[3,4-e][1,4]-thiazin-4(10H)-one A solution of 2-{[2-amino-5-(trifluoromethoxy)phenyl]disulfanyl}-4-(trifluoromethoxy)aniline (IIb-2) (0.456 g, 1.10 mmol) and oxane-3,5-dione (III-5) (0.250 g, 2.19 mmol) in ethanol (7 ml) and triethylamine (0.5 ml) was refluxed for 16 hours. After completion of the reaction the mixture was concentrated to dryness under reduced pressure. The yield after flash chromatography (100-200 mesh size silica gel, 25-30% ethyl acetate in hexane) was 18 mg.

Compound 7. 7-(trifluoromethoxy)-1H,3H-benzo[b]thiopyrano[3,4-e][1,4]-thiazin-4(10H)-one A solution of 2-{[2-amino-5-(trifluoromethoxy)phenyl]disulfanyl}-4-(trifluoromethoxy)aniline (IIb-2) (0.239 g, 0.57 mmol) and thiane-3,5-dione (III-7) (0.150 g, 1.15 mmol) in ethanol (1.5 ml) and triethylamine (0.4 ml) was refluxed for 16 hours. After completion of the reaction the mixture was concentrated to dryness under reduced pressure. The yield after preparative TLC (50% ethyl acetate in hexane) was 11.3 mg.

Compound 8. 7-methoxy-1H,3H-benzo[b]thiopyrano[3,4-e][1,4]thiazin-4(10H)-one A solution of 2-[(2-amino-5-methoxyphenyl)disulfanyl]-4-methoxyaniline (IIb-4) (0.177 g, 0.58 mmol) and thiane-3,5-dione (III-7) (0.150 g, 1.15 mmol) in ethanol (1.5 ml) and triethylamine (0.4 ml) was refluxed for 16 hours. After completion of the reaction the mixture was concentrated to dryness under reduced pressure. The yield after preparative TLC (50% ethyl acetate in hexane) was 2 mg.

Compound 9. 9-methoxy-2,3,4,5-tetrahydrobenzo[5,6][1,4]thiazino[2,3-c]-azepin-1(6H)-one A solution of 2-[(2-amino-5-methoxyphenyl)disulfanyl]-4-methoxyaniline (IIb-4) (0.048 g, 0.155 mmol) and azepane-2,4-dione (III-9) (0.040 g, 0.314 mmol) in ethanol (2 ml) containing catalytic amount of triethylamine (4 drops) was refluxed for 16 hours. After completion of the reaction the mixture was concentrated to dryness under reduced pressure. The residue was triturated with pentane dichloromethane mixture. The solids were collected and dried under reduced pressure. The yield was 17 mg.

Compound 10. 9-(trifluoromethoxy)-2,3,4,5-tetrahydrobenzo[5,6][1,4]-thiazino[2,3-c]azepin-1(6H)-one A solution of 2-{[2-amino-5-(trifluoromethoxy)phenyl]disulfanyl}-4-(trifluoromethoxy)aniline (IIb-2) (0.081 g, 0.196 mmol) and azepane-2,4-dione (III-9) (0.050 g, 0.393 mmol) in ethanol (2 ml) containing catalytic amount of triethylamine (0.1 ml) was refluxed for 16 hours. After completion of the reaction the mixture was concentrated to dryness under reduced pressure. The yield after preparative TLC (5% methanol in dichloromethane) was 18 mg.

Compound 11. 3,3-dimethyl-8-(trifluoromethoxy)-2,3-dihydro-4H-benzo-[b]pyrido[4,3-e][1,4]thiazine-1,4(5H)-dione 3,3-dimethyl-8-(trifluoromethoxy)-3,4-dihydro-2H-benzo[b]pyrido-[4,3-e][1,4]thiazin-1(5H)-one (2) (25 mg, 0.076 mmol) was mixed with phosphate buffer (2.5 ml, pH 7.4) and stirred at RT for 24. Acetonitrile (2.5 ml) was added and stirring continued at 40° C. for 72 hours. The mixture was concentrated to dryness under reduced pressure. The yield after preparative TLC (5% methanol in dichloromethane) was 10 mg.

Compound 12. 3,3-dimethyl-3,4-dihydro-2H-benzo[b]pyrido[4,3-e][1,4]-thiazin-1(5H)-one A solution of 2-aminobenzene-1-thiol (0.15 g, 1.198 mmol) and 6,6-dimethylpiperidine-2,4-dione (III-1) (0.169 g, 1.198 mmol) in ethanol (5 ml) containing catalytic amount of triethylamine (4 drops) was refluxed for 16 hours. After completion of the reaction the mixture was concentrated to dryness under reduced pressure. The residue was crystallized from dichloromethane pentane mixture. The yield was 0.25 g.

Compound 13. 3,3-diethyl-8-(trifluoromethoxy)-3,4-dihydro-2H-benzo-[b]pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.05 g, 0.12 mmol) and 6,6-diethylpiperidine-2,4-dione (III-13) (0.04 g, 0.24 mmol) in ethanol (5 ml) containing catalytic amount of triethylamine (4 drops) was refluxed for 16 hours. After completion of the reaction the mixture was concentrated to dryness under reduced pressure. The yield after flash chromatography (100-200 mesh size silica gel, 40% ethyl acetate in hexane) was 50 mg.

Compound 14. 8-(trifluoromethoxy)-2H,4H-spiro[benzo[b]pyrido[4,3-e]-[1,4]thiazine-3,1'-cyclopentan]-1(5H)-one A solution of 2-{[2-amino-5-(trifluoromethoxy)phenyl]disulfanyl}-4-(trifluoromethoxy)aniline (IIb-2) (0.128 g, 0.30 mmol) and 6-azaspiro[4.5]-decane-7,9-dione (III-14) (0.100 g, 0.60 mmol) in ethanol (5 ml) containing catalytic amount of triethylamine (4 drops) was refluxed for 16 hours. After completion of the reaction the mixture was concentrated to dryness under reduced pressure. The residue was dissolved in the minimum amount of dichloromethane methanol mixture (9:1). n-Pentane was added and the mixture was stirred for 30 minutes. The solids were collected, washed with n-pentane and dried under reduced pressure. The yield was 0.14 g

Compound 15. 8-(trifluoromethoxy)-2',3',5',6'-tetrahydro-2H,4H-spiro-[benzo[b]pyrido[4,3-e][1,4]thiazine-3,4'-pyran]-1(5H)-one A solution of 2-{[2-amino-5-(trifluoromethoxy)phenyl]disulfanyl}-4-(trifluoromethoxy)aniline (IIb-2) (0.128 g, 0.30 mmol) and 9-oxa-1-azaspiro-[5.5]undecane-2,4-dione (III-15) (0.109 g, 0.60 mmol) in ethanol (5 ml) containing catalytic amount of triethylamine (4 drops) was refluxed for 16 hours. After completion of the reaction the mixture was concentrated to dryness under reduced pressure. The residue was dissolved in the minimum amount of dichloromethane methanol mixture (9:1). n-Pentane was added and the mixture was stirred for 30 minutes. The solids were collected, washed with n-pentane and dried under reduced pressure. The yield was 0.15 g.

Compound 16. 2-ethyl-3,3-dimethyl-8-(trifluoromethoxy)-3,4-dihydro-2H-benzo[b]pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.05 g, 0.12 mmol) and -ethyl-6,6-dimethylpiperidine-2,4-dione (III-16) (0.04 g, 0.24 mmol) in ethanol (5 ml) containing catalytic amount of triethylamine (4 drops) was refluxed for 16 hours. After completion of the reaction the mixture was concentrated to dryness under reduced pressure. The yield after flash chromatography (100-200 mesh size silica gel, 40% ethyl acetate in hexane) was 25 mg.

Compound 17. 2-ethyl-8-(trifluoromethoxy)-2',3',5',6'-tetrahydro-2H,4H-spiro[benzo[b]pyrido[4,3-e][1,4]thiazine-3,4'-pyran]-1(5H)-one A solution of 2-{[2-amino-5-(trifluoromethoxy)phenyl]disulfanyl}-4-(trifluoromethoxy)aniline (IIb-2) (0.15 g, 0.36 mmol) and 1-ethyl-9-oxa-1-azaspiro[5.5]undecane-2,4-dione (III-17) (0.15 g, 0.72 mmol) in ethanol (5 ml) containing catalytic amount of triethylamine (4 drops) was refluxed for 16 hours. After completion of the reaction the mixture was concentrated to dryness under reduced pressure. The residue was dissolved in the minimum amount of dichloromethane methanol mixture (9:1). n-Pentane was added and the mixture was stirred for 30 minutes. The solids were collected, washed with n-pentane and dried under reduced pressure. The yield was 75 mg.

Compound 18. 4,4-dimethyl-8-(trifluoromethoxy)-3,4-dihydro-2H-benzo-[b]pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.1 g, 0.24 mmol) and 5,5-dimethylpiperidine-2,4-dione (III-18) (0.068 g, 0.48 mmol) in ethanol (5 ml) containing catalytic amount of triethylamine (4 drops) was refluxed for 16 hours. After completion of the reaction the mixture was concentrated to dryness under reduced pressure. The residue was dissolved in the minimum amount of dichloromethane methanol mixture (9:1). n-Pentane was added and the mixture was stirred for 30 minutes. The solids were collected, washed with n-pentane and dried under reduced pressure. The yield was 40 mg.

Compound 19. 2-ethyl-4,4-dimethyl-8-(trifluoromethoxy)-3,4-dihydro-2H-benzo[b]pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.04 g, 0.096 mmol) and 1-ethyl-5,5-dimethylpiperidine-2,4-dione (III-17) (0.032 g, 0.192 mmol) in ethanol (5 ml) containing catalytic amount of triethylamine (3 drops) was refluxed for 16 hours. After completion of the reaction the mixture was concentrated to dryness under reduced pressure. The residue was crystallized using mixture of dichloromethane in n-pentane. Crystals were collected and washed with n-pentane. The yield was 30 mg.

Compound 20. 4,4-dimethyl-9-(trifluoromethoxy)-2,6-dihydropyrazolo[4,3-c]phenothiazin-5(4H)-one A solution of 2-{[2-amino-5-(trifluoromethoxy)phenyl]disulfanyl}-4-(trifluoromethoxy)aniline (IIb-2) ((0.1 g, 0.24 mmol) and 7-bromo-4,4-dimethyl-4,5,6,7-tetrahydro-2H-indazol-6-one (III-20) (0.116 g, 0.48 mmol) in ethanol (5 ml) containing catalytic amount of triethylamine (4 drops) was refluxed for 16 hours. After completion of the reaction the mixture was concentrated to dryness under reduced pressure. The yield after flash chromatography (100-200 mesh size silica gel, 20% ethyl acetate in hexane) was 25 mg.

Compound 21. 4,4-dimethyl-2,6-dihydropyrazolo[4,3-c]phenothiazin-5(4H)-one

A solution of 2-aminobenzene-1-thiol (0.052 g, 0.41 mmol) and 7-bromo-4,4-dimethyl-4,5,6,7-tetrahydro-2H-indazol-6-one (III-20) (0.1 g, 0.41 mmol) in ethanol (5 ml) containing catalytic amount of triethylamine (4 drops) was refluxed for 16 hours. After completion of the reaction the mixture was concentrated to dryness under reduced pressure. The yield after flash chromatography (100-200 mesh size silica gel, 20% ethyl acetate in hexane) was 22.5 mg.

Compound 22. 8-chloro-4,4-dimethyl-2,6-dihydropyrazolo[4,3-c]phenolthiazin-5(4H)-one A solution of 2-amino-4-chlorobenzene-1-thiol (0.1 g, 0.63 mmol) and 7-bromo-4,4-dimethyl-4,5,6,7-tetrahydro-2H-indazol-6-one (III-20) (0.152 g, 0.63 mmol) in ethanol (5 ml) containing catalytic amount of triethylamine (4 drops) was refluxed for 16 hours. After completion of the reaction the mixture was concentrated to dryness under reduced pressure. The yield after flash chromatography (100-200 mesh size silica gel, 20% ethyl acetate in hexane) was 46 mg.

Compound 23. 5,5-dimethyl-10-(trifluoromethoxy)-5,7-dihydro-6H-pyrimido[5,4-c]phenothiazin-6-one A solution of 2-{[2-amino-5-(trifluoromethoxy)phenyl]disulfanyl}-4-(trifluoromethoxy)aniline (IIb-2) (0.05 g, 0.12 mmol) and 5,5-dimethyl-5,6,7,8-tetrahydroquinazolin-7-one (III-23) (0.042 g, 0.24 mmol) in ethanol (5 ml) containing catalytic amount of triethylamine (4 drops) was refluxed for 18 hours. After completion of the reaction the mixture was concentrated to dryness under reduced pressure. The yield after flash chromatography (100-200 mesh size silica gel, 50% ethyl acetate in hexane) was 10 mg.

Compound 24. 9-chloro-5,5-dimethyl-5,7-dihydro-6H-pyrimido[5,4-c]-phenothiazin-6-one A solution of 2-amino-4-chlorobenzene-1-thiol (0.05 g, 0.31 mmol) and 5,5-dimethyl-5,6,7,8-tetrahydroquinazolin-7-one (III-23) (0.055 g, 0.31 mmol) in ethanol (5 ml) containing catalytic amount of triethylamine (4 drops) was refluxed for 16 hours. The mixture was concentrated to dryness under reduced pressure. The residue was dissolved in THF (5 ml) and stirred at 50° C. for 18 hours. The mixture was concentrated to dryness under reduced pressure. The yield after flash chromatography (100-200 mesh size silica gel, 20% ethyl acetate in hexane) was 20 mg.

Compound 25. 2-acetyl-4,4-dimethyl-9-(trifluoromethoxy)-2,6-dihydropyrazolo[4,3-c]phenothiazin-5(4H)-one Di-isopropylamine (0.8 mg, 0.0078 mmol) was added to the solution of 4,4-dimethyl-9-(trifluoromethoxy)-2H,4H,5H,6H-pyrazolo[4,3-c]phenothiazin-5-one (20) (9.6 mg, 0.0026 mmol) in THF (2 ml) and the mixture was stirred for 15 minutes. Acetic anhydride (0.8 mg, 0.0078 mmol) was added and the resulting mixture was stirred at RT for 6 hours. Water was added and the mixture was extracted with ethyl acetate. The organic phase was washed with brine, dried over sodium sulphate and concentrated under reduced pressure. The yield after crystallization from dichloromethane pentane mixture was 3.5 mg.

Compound 26. 2-acetyl-4,4-dimethyl-2,6-dihydropyrazolo[4,3-c]phenolthiazin-5(4H)-one Di-isopropylamine (0.045 ml, 0.318 mmol) was added to the solution of 4,4-dimethyl-2H,4H,5H,6H-pyrazolo[4,3-c]phenothiazin-5-one (21) (30 mg, 0.106 mmol) in THF (3 ml) and the mixture was stirred for 15 minutes. Acetic anhydride (0.02 ml, 0.212 mmol) was added and the resulting mixture was stirred at RT for 6 hours. Water was added and the mixture was extracted with ethyl acetate. The organic phase was washed with brine, dried over sodium sulphate and concentrated under reduced pressure. The yield after crystallization from dichloromethane pentane mixture was 15 mg.

Compound 27. 2-acetyl-8-chloro-4,4-dimethyl-2,6-dihydropyrazolo[4,3-c]-phenothiazin-5(4H)-one Di-isopropylamine (0.019 ml, 0.142 mmol) was added to the solution of 8-chloro-4,4-dimethyl-2H,4H,5H,6H-pyrazolo[4,3-c]phenothiazin-5-one (22) (15 mg, 0.047 mmol) in THF (2 ml) and the mixture was stirred for 15 minutes. Acetic anhydride (0.014 ml, 0.142 mmol) was added and the resulting mixture was stirred at RT for 6 hours. Water was added and the mixture was extracted with ethyl acetate. The organic phase was washed with brine, dried over sodium sulphate and concentrated under reduced pressure. The yield after crystallization from dichloromethane pentane mixture was 5 mg.

Compound 28. 5,5-dimethyl-5,7-dihydro-6H-pyrimido[5,4-c]phenothiazin-6-one

A solution of 2-aminobenzene-1-thiol (0.05 g, 0.39 mmol) and 5,5-dimethyl-5,6,7,8-tetrahydroquinazolin-7-one (III-23) (0.070 g, 0.39 mmol) in ethanol (5 ml) containing catalytic amount of triethylamine (4 drops) was refluxed for 16 hours. The mixture was concentrated to dryness under reduced pressure. The residue was dissolved in THF (2 ml) and stirred at 50° C. for 18 hours. The mixture was concentrated to dryness under reduced pressure. The yield after flash chromatography (100-200 mesh size silica gel, 20% ethyl acetate in hexane) was 6 mg.

Compound 29. 2,3,3-triethyl-8-(trifluoromethoxy)-3,4-dihydro-2H-benzo-[b]pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.015 g, 0.036 mmol) and 1,6,6-triethylpiperidine-2,4-dione (III-29) (0.014 g, 0.072 mmol) in ethanol (5 ml) containing catalytic amount of triethylamine (3 drops) was refluxed for 16 hours. After completion of the reaction the mixture was concentrated to dryness under reduced pressure. The residue was crystallized using mixture of dichloromethane in n-pentane. Crystals were collected and washed with n-pentane. The yield was 5 mg.

Compound 30. 4,4-dimethyl-8-(trifluoromethoxy)-3,4-dihydro-2H-benzo-[b]pyrido[4,3-e][1,4]thiazin-1(5H)-one 10-oxide 4,4-dimethyl-8-(trifluoromethoxy)-3,4-dihydro-2H-benzo[b]pyrido-[4,3-e][1,4]thiazin-1(5H)-one (18) (20 mg, 0.061 mmol) was mixed with phosphate buffer (2.5 ml, pH 7.4) and acetonitrile (2.5 ml). The mixture was stirred at 40° C. for 96 hours. The mixture was concentrated to dryness under reduced pressure. The yield after preparative TLC was 1.1 mg.

Compound 31. 3-phenyl-8-(trifluoromethoxy)-3,4-dihydro-2H-benzo[b]-pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.1 g, 0.24 mmol) and 6-phenylpiperidine-2,4-dione (III-31) (0.09 g, 0.48 mmol) in ethanol (10 ml) containing catalytic amount of triethylamine (3 drops) was refluxed for 18 hours. After completion of the reaction the mixture was concentrated to dryness under reduced pressure. The residue was dissolved to the minimum amount of chloroform/methanol. n-Hexane was added and the mixture was stirred for 30 minutes. The solids were collected, washed with n-pentane and dried under reduced pressure. The yield was 0.13 g.

Compound 32. 3-methyl-8-(trifluoromethoxy)-3,4-dihydro-2H-benzo[b]-pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.15 g, 0.36 mmol) and 6-methylpiperidine-2,4-dione (III-32) (0.09 g, 0.72 mmol) in ethanol (10 ml) containing catalytic amount of triethylamine (3 drops) was refluxed for 18 hours. After completion of the reaction the mixture was concentrated to dryness under reduced pressure. The residue was dissolved to the minimum amount of chloroform/methanol. n-Hexane was added and the mixture was stirred for 30 minutes. The solids were collected, washed with n-pentane and dried under reduced pressure. The yield was 0.2 g.

Compound 33. 3-bromo-8,8-dimethyl-8,9-dihydro-7H-pyrazino[2,3-b]-pyrido[4,3-e][1,4]thiazin-6(10H)-one A solution of 3-amino-6-bromopyrazine-2-thiol (IIb-33) (0.1 g, 0.49 mmol) and 6,6-dimethylpiperidine-2,4-dione (III-1) (0.069 g, 0.49 mmol) in ethanol (5 ml) containing catalytic amount of triethylamine (3 drops) was stirred in autoclave at 130° C. for 4 hours. After completion of the reaction the mixture was concentrated to dryness under reduced pressure. The yield after flash chromatography (100-200 mesh size silica gel, 30% ethyl acetate in hexane) was 12 mg.

Compound 34. 3-methyl-8-(trifluoromethoxy)-2H-benzo[b]pyrido[4,3-e]-[1,4]thiazin-1(5H)-one Activated charcoal (15 mg) was added to the solution of Compound 32 (30 mg, 0.09 mmol) in acetic acid (2 ml). The resulting mixture was stirred at 120° C. under oxygen atmosphere for 30 minutes. After cooling the mixture was filtered through celite pad and the filtrate was evaporated to dryness. Water was added and the mixture was neutralized with saturated aqueous NaHCO$_3$ solution and extracted with dichloromethane. The organic phase was washed with brine, dried over sodium sulphate and concentrated under reduced pressure. The yield after preparative HPLC was 3.5 mg.

Compound 35. 3-phenyl-8-(trifluoromethoxy)-2H-benzo[b]pyrido[4,3-e]-[1,4]thiazin-1(5H)-one Compound 35 was prepared according to the same procedure used for the preparation of Compound 34. Compound 31 (30 mg, 0.08 mmol) was used as starting material. The yield after preparative HPLC was 2.0 mg.

Compound 36. 3-methoxy-8,8-dimethyl-8,9-dihydro-7H-pyrazino[2,3-b]-pyrido[4,3-e][1,4]thiazin-6(10H)-one A solution of 3-amino-6-methoxypyrazine-2-thiol (IIb-36) (50 mg, 0.318 mmol) and 6,6-dimethylpiperidine-2,4-dione (III-1) (46 mg, 0.318 mmol) in ethanol (5 ml) containing catalytic amount of triethylamine (3 drops) was refluxed for 18 hours. After completion of the reaction the mixture was concentrated to dryness under reduced pressure. The yield after flash chromatography (100-200 mesh size silica gel, 3% methanol in dichloromethane) and recrystallization from the methanol/tetrahydrofuran/n-pentane mixture was 7 mg.

Compound 37. 8-methoxy-3-methyl-3,4-dihydro-2H-benzo[b]pyrido[4,3-e]-[1,4]thiazin-1(5H)-one A solution of 2-[(2-amino-5-methoxyphenyl)disulfanyl]-4-methoxyaniline (IIb-4) (0.1 g, 0.32 mmol) and 6-methylpiperidine-2,4-dione (III-32) (83 mg, 0.64 mmol) in ethanol (5 ml) containing catalytic amount of triethylamine (3 drops) was refluxed for 18 hours. After completion of the reaction the mixture was concentrated to dryness under reduced pressure. The residue was dissolved to the minimum amount of chloroform/methanol. n-Hexane was added and the mixture was stirred for 30 minutes. The solids were collected, washed with n-hexane and dried under reduced pressure. The yield was 0.12 g.

Compound 38. 7-chloro-8-methoxy-3-methyl-3,4-dihydro-2H-benzo[b]-pyrido[4,3-e][1,4]thiazin-1(5H)-one A solution of 2-[(2-amino-4-chloro-5-methoxyphenyl)disulfanyl]-5-chloro-4-methoxyaniline (IIb-1) (0.1 g, 0.26 mmol) and 6-methylpiperidine-2,4-dione (III-32) (68 mg, 0.53 mmol) in ethanol (5 ml) containing catalytic amount of triethylamine (3 drops) was refluxed for 18 hours. After completion of the reaction the mixture was concentrated to dryness under reduced pressure. The residue was dissolved to the minimum amount of chloroform/methanol. n-Hexane was added and the mixture was stirred for 30 minutes. The solids were collected, washed with n-hexane and dried under reduced pressure. The yield was 0.105 g.

Compound 39. 8-methoxy-3-phenyl-3,4-dihydro-2H-benzo[b]pyrido[4,3-e]-[1,4]thiazin-1(5H)-one A solution of 2-[(2-amino-5-methoxyphenyl)disulfanyl]-4-methoxyaniline (IIb-4) (0.1 g, 0.32 mmol) and 6-phenylpiperidine-2,4-dione (III-31) (0.12 g, 0.64 mmol) in ethanol (5 ml) containing catalytic amount of triethylamine (3 drops) was refluxed for 18 hours. After completion of the reaction the mixture was concentrated to dryness under reduced pressure. The residue was dissolved to the minimum amount of chloroform/methanol. n-Hexane was added and the mixture was stirred for 30 minutes. The solids were collected, washed with n-hexane and dried under reduced pressure. The yield was 0.14 g.

Compound 40. 7-chloro-8-methoxy-3-phenyl-3,4-dihydro-2H-benzo[b]-pyrido[4,3-e][1,4]thiazin-1(5H)-one A solution of 2-[(2-amino-4-chloro-5-methoxyphenyl)disulfanyl]-5-chloro-4-methoxyaniline (IIb-1) (0.1 g, 0.26 mmol) and 6-phenylpiperidine-2,4-dione (III-31) (0.1 g, 0.53 mmol) in ethanol (5 ml) containing catalytic amount of triethylamine (3 drops) was refluxed for 18 hours. After completion of the reaction the mixture was concentrated to dryness under reduced pressure. The residue was dissolved to the minimum amount of chloroform/methanol. n-Hexane was added and the mixture was stirred for 30 minutes. The solids were collected, washed with n-hexane and dried under reduced pressure. The yield was 0.104 g.

Compound 41. N-(3,3-dimethyl-1-oxo-8-(trifluoromethoxy)-1,3,4,5-tetrahydro-2H-benzo[b]pyrido[4,3-e][1,4]thiazin-2-yl)acetamide A solution of 2-{[2-amino-5-(trifluoromethoxy)phenyl]disulfanyl}-4-(trifluoromethoxy)aniline (IIb-2) (10 mg, 0.024 mmol) and 1-acetoamino-6,6-dimethylpiperidine-2,4-dione (III-41) (10 mg, 0.048 mmol) in ethanol (0.5 ml) containing catalytic amount of triethylamine (1 drops) was refluxed for 18 hours. After completion of the reaction the mixture was concentrated to dryness under reduced pressure. The residue was recrystallized from the mixture of dichloromethane:n-pentane. The solids were collected, washed with n-pentane and dried under reduced pressure. The yield was 8 mg.

Compound 42. N-(3-methyl-1-oxo-8-(trifluoromethoxy)-1,3,4,5-tetrahydro-2H-benzo[b]pyrido[4,3-e][1,4]thiazin-2-yl)acetamide A solution of 2-{[2-amino-5-(trifluoromethoxy)phenyl]disulfanyl}-4-(trifluoromethoxy)aniline (IIb-2) (40 mg, 0.096 mmol) and 1-acetoamino-6-methylpiperidine-2,4-dione (III-42) (35 mg, 0.192 mmol) in ethanol (1 ml) containing catalytic amount of triethylamine (2 drops) was refluxed for 18 hours. After completion of the reaction the mixture was concentrated to dryness under reduced pressure. The yield after preparative TLC (5% methanol in dichloromethane was 4 mg.

Compound 43. 2-amino-3,3-dimethyl-8-(trifluoromethoxy)-3,4-dihydro-2H-benzo[b]pyrido[4,3-e][1,4]thiazin-1(5H)-one Compound 41 (20 mg, 0.052 mmol) was dissolved in methanol (1 ml). Concentrated HCl (0.5 ml) was added and the resulting mixture stirred at 60° C. for 5 hours. The reaction was quenched by adding saturated $NaHCO_3$ and extracted with dichloromethane. The organic layer was dried over sodium sulphate and concentrated under reduced pressure. The solids were washed with dichloromethane:n-pentane mixture. The yield after drying was 15 mg.

Compound 44. 2-amino-3-methyl-8-(trifluoromethoxy)-3,4-dihydro-2H-benzo[b]pyrido[4,3-e][1,4]thiazin-1(5H)-one Compound 42 (10 mg, 0.027 mmol) was dissolved in methanol (1 ml). Concentrated HCl (0.5 ml) was added and the resulting mixture stirred at 60° C. for 5 hours. The reaction was quenched by adding saturated $NaHCO_3$ and extracted with dichloromethane. The organic layer was dried over sodium sulphate and concentrated under reduced pressure. The solids were washed with dichloromethane:n-pentane mixture. The yield after drying was 4 mg.

Compound 45. 2-amino-8-methoxy-3,3-dimethyl-3,4-dihydro-2H-benzo[b]-pyrido[4,3-e][1,4]thiazin-1(5H)-one Compound 52 (10 mg, 0.030 mmol) was dissolved in methanol (2 ml). Concentrated HCl (0.2 ml) was added and the resulting mixture stirred at 60° C. for 5 hours. The reaction was quenched by adding saturated $NaHCO_3$ and extracted with dichloromethane. The organic layer was dried over sodium sulphate and concentrated under reduced pressure. The solids were washed with dichloromethane:n-pentane mixture. The yield after drying was 5 mg.

Compound 46. N-(8-methoxy-3-methyl-1-oxo-1,3,4,5-tetrahydro-2H-benzo-[b]pyrido[4,3-e][1,4]thiazin-2-yl)acetamide A solution of 2-[(2-amino-5-methoxyphenyl)disulfanyl]-4-methoxyaniline (IIb-4) (100 mg, 0.325 mmol) and 1-acetoamino-6-methylpiperidine-2,4-dione (III-42) (119 mg, 0.65 mmol) in ethanol (2 ml) containing catalytic amount of triethylamine (2 drops) was refluxed for 18 hours. After completion of the reaction the mixture was concentrated to dryness under reduced pressure. The residue was recrystallized from the mixture of dichloromethane:n-pentane. The solids were collected, washed with n-pentane and dried under reduced pressure. The yield was 30 mg.

Compound 47. 2-amino-8-methoxy-3-methyl-3,4-dihydro-2H-benzo[b]-pyrido[4,3-e][1,4]thiazin-1(5H)-one Compound 46 (18 mg, 0.056 mmol) was dissolved in methanol (1 ml). Concentrated HCl (0.5 ml) was added and the resulting mixture stirred at 60° C. for 5 hours. The reaction was quenched by adding saturated $NaHCO_3$ and extracted with dichloromethane. The organic layer was dried over sodium sulphate and concentrated under reduced pressure. The solids were washed with dichloromethane:n-pentane mixture. The yield after drying was 7 mg.

Compound 48. N-(7-chloro-8-methoxy-3,3-dimethyl-1-oxo-1,3,4,5-tetrahydro-2H-benzo[b]pyrido[4,3-e][1,4]thiazin-2-yl)acetamide A solution of 2-[(2-amino-4-chloro-5-methoxyphenyl)disulfanyl]-5-chloro-4-methoxyaniline (IIb-1) (100 mg, 0.27 mmol) and 1-acetoamino-6,6-dimethylpiperidine-2,4-dione (III-41) (105 mg, 0.54 mmol) in ethanol (2 ml) containing catalytic amount of triethylamine (2 drops) was refluxed for 18 hours. After completion of the reaction the mixture was concentrated to dryness under reduced pressure. The residue was recrystallized from the mixture of dichloromethane:n-pentane. The solids were collected, washed with n-pentane and dried under reduced pressure. The yield was 60 mg.

Compound 49. 2-amino-7-chloro-8-methoxy-3,3-dimethyl-3,4-dihydro-2H-benzo[b]pyrido[4,3-e][1,4]thiazin-1(5H)-one Compound 48 (30 mg, 0.082 mmol) was dissolved in methanol (2 ml). Concentrated HCl (0.5 ml) was added and the resulting mixture stirred at 60° C. for 5 hours. The reaction was quenched by adding saturated $NaHCO_3$ and extracted with dichloromethane. The organic layer was dried over sodium sulphate and concentrated under reduced pressure. The solids were washed with dichloromethane:n-pentane mixture. The yield after drying was 18 mg.

Compound 50. N-(7-chloro-8-methoxy-3-methyl-1-oxo-1,3,4,5-tetrahydro-2H-benzo[b]pyrido[4,3-e][1,4]thiazin-2-yl)acetamide A solution of 2-[(2-amino-4-chloro-5-methoxyphenyl)disulfanyl]-5-chloro-4-methoxyaniline (IIb-1) (100 mg, 0.27 mmol) and 1-acetoamino-6-methylpiperidine-2,4-dione (III-42) (98 mg, 0.54 mmol) in ethanol (2 ml) containing catalytic amount of triethylamine (2 drops) was refluxed for 18 hours. After completion of the reaction the mixture was concentrated to dryness under reduced pressure. The residue was recrystallized from the mixture of dichloromethane:n-pentane. The solids were collected, washed with n-pentane and dried under reduced pressure. The yield was 30 mg.

Compound 51. 2-amino-7-chloro-8-methoxy-3-methyl-3,4-dihydro-2H-benzo[b]pyrido[4,3-e][1,4]thiazin-1(5H)-one Compound 50 (15 mg, 0.044 mmol) was dissolved in methanol (1 ml). Concentrated HCl (0.2 ml) was added and the resulting mixture stirred at 60° C. for 5 hours. The reaction was quenched by adding saturated NaHCO₃ and extracted with dichloromethane. The organic layer was dried over sodium sulphate and concentrated under reduced pressure. The solids were washed with dichloromethane:n-pentane mixture. The yield after drying was 12 mg.

Compound 52. N-(8-methoxy-3,3-dimethyl-1-oxo-1,3,4,5-tetrahydro-2H-benzo[b]pyrido[4,3-e][1,4]thiazin-2-yl)acetamide A solution of 2-[(2-amino-5-methoxyphenyl)disulfanyl]-4-methoxyaniline (IIb-4) (90 mg, 0.29 mmol) and 1-acetoamino-6,6-dimethylpiperidine-2,4-dione (III-41) (115 mg, 0.58 mmol) in ethanol (2 ml) containing catalytic amount of triethylamine (2 drops) was refluxed for 18 hours. After completion of the reaction the mixture was concentrated to dryness under reduced pressure. The residue was recrystallized from the mixture of dichloromethane:n-pentane. The solids were collected, washed with n-pentane and dried under reduced pressure. The yield was 60 mg.

Compound 53. 3-ethyl-8-(trifluoromethoxy)-3,4-dihydro-2H-benzo[b]-pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (50 mg, 0.12 mmol) and 6-ethylpiperidine-2,4-dione (III-53) (34 mg, 0.24 mmol) in ethanol (5 ml) containing catalytic amount of triethylamine (3 drops) was refluxed for 16 hours. After completion of the reaction the mixture was concentrated to dryness under reduced pressure. The residue was crystallized from dichloromethane:n-pentane mixture. The solids were collected, washed with n-pentane and dried under reduced pressure. The yield was 25 mg.

Compound 54. 7-chloro-3-ethyl-8-methoxy-3,4-dihydro-2H-benzo[b]-pyrido[4,3-e][1,4]thiazin-1(5H)-one A solution of 2-[(2-amino-4-chloro-5-methoxyphenyl)disulfanyl]-5-chloro-4-methoxyaniline (IIb-1) (30 mg, 0.08 mmol) and 6-ethylpiperidine-2,4-dione (III-53) (23 mg, 0.16 mmol) in ethanol (5 ml) containing catalytic amount of triethylamine (3 drops) was refluxed for 16 hours. After completion of the reaction the mixture was concentrated to dryness under reduced pressure. The yield after flash chromatography (100-200 mesh size silica gel, 2% methanol in dichloromethane) was 4 mg.

Compound 55. 3-ethyl-8-methoxy-3,4-dihydro-2H-benzo[b]pyrido[4,3-e]-[1,4]thiazin-1(5H)-one A solution of 2-[(2-amino-5-methoxyphenyl)disulfanyl]-4-methoxyaniline (IIb-4) (30 mg, 0.097 mmol) and 6-ethylpiperidine-2,4-dione (III-53) (27 mg, 0.194 mmol) in ethanol (5 ml) containing catalytic amount of triethylamine (3 drops) was refluxed for 16 hours. After completion of the reaction the mixture was concentrated to dryness under reduced pressure. The yield after preparative-TLC was 1.5 mg.

Compound 56. 7-chloro-8-methoxy-3-(pyridin-2-yl)-3,4-dihydro-2H-benzo-[b]pyrido[4,3-e][1,4]thiazin-1(5H)-one A solution of 2-[(2-amino-4-chloro-5-methoxyphenyl)disulfanyl]-5-chloro-4-methoxyaniline (IIb-1) (40 mg, 0.106 mmol) and 6-(pyridin-2-yl)-piperidine-2,4-dione (III-56) (40 mg, 0.212 mmol) in ethanol (5 ml) containing catalytic amount of triethylamine (3 drops) was refluxed for 16 hours. After completion of the reaction the mixture was concentrated to dryness under reduced pressure. The residue was crystallized from dichloromethane:n-pentane mixture. The solids were collected, washed with n-pentane and dried under reduced pressure. The yield was 30 mg.

Compound 57. 3-(pyridin-2-yl)-8-(trifluoromethoxy)-3,4-dihydro-2H-benzo-[b]pyrido[4,3-e][1,4]thiazin-1(5H)-one A solution of 2-{[2-amino-5-(trifluoromethoxy)phenyl]disulfanyl}-4-(trifluoromethoxy)aniline (IIb-2) (0.1 g, 0.24 mmol) and 6-(pyridin-2-yl)piperidine-2,4-dione (III-56) (0.09 g, 0.48 mmol) in ethanol (5 ml) containing catalytic amount of triethylamine (3 drops) was refluxed for 16 hours. After completion of the reaction the mixture was concentrated to dryness under reduced pressure. The residue was crystallized from dichloromethane:n-pentane mixture. The solids were collected, washed with n-pentane and dried under reduced pressure. The yield was 0.13 g.

Compound 58. 8-methoxy-3-(pyridin-2-yl)-3,4-dihydro-2H-benzo[b]pyrido-[4,3-e][1,4]thiazin-1(5H)-one A solution of 2-[(2-amino-5-methoxyphenyl)disulfanyl]-4-methoxyaniline (IIb-4) (30 mg, 0.097 mmol) and 6-(pyridin-2-yl)piperidine-2,4-dione (III-56) (37 mg, 0.194 mmol) in ethanol (5 ml) containing catalytic amount of triethylamine (3 drops) was refluxed for 16 hours. After completion of the reaction the mixture was concentrated to dryness under reduced pressure. The yield after flash chromatography (100-200 mesh size silica gel, 5% methanol in dichloromethane) was 15 mg.

Compound 59. 3-(pyridin-2-yl)-8-(trifluoromethoxy)-2H-benzo[b]pyrido-[4,3-e][1,4]thiazin-1(5H)-one Compound 59 was prepared according to the same procedure used for the preparation of Compound 34. Compound 57 (30 mg, 0.08 mmol) was used as starting material. The yield after preparative HPLC was 3.0 mg.

Compound 60. 2-(dimethylamino)-3,3-dimethyl-8-(trifluoromethoxy)-3,4-dihydro-2H-benzo[b]pyrido[4,3-e][1,4]thiazin-1(5H)-one Methyl iodide (37 mg, 0.26 mmol) was added to the mixture of Compound 43 (30 mg, 0.087 mmol) and $K_2CO_3$ (2 mg, 0.104 mmol) in DMF (1 ml). The resulting mixture was stirred at RT for 16 hours. Brine was added to the mixture and the resulting mixture was extracted with ethyl acetate. The organic phase was dried over sodium sulphate and concentrated under reduced pressure. The yield after preparative-TLC (2% methanol in dichloromethane) was 4 mg.

Compound 61. 3,3-dimethyl-2-(methylamino)-8-(trifluoromethoxy)-3,4-dihydro-2H-benzo[b]pyrido[4,3-e][1,4]thiazin-1(5H)-one Methyl iodide (37 mg, 0.26 mmol) was added to the mixture of Compound 43 (30 mg, 0.087 mmol) and $K_2CO_3$ (2 mg, 0.104 mmol) in DMF (1 ml). The resulting mixture was stirred at RT for 16 hours. Brine was added to the mixture and the resulting mixture was extracted with ethyl acetate. The organic phase was dried over sodium sulphate and concentrated under reduced pressure. The yield after preparative-TLC (2% methanol in dichloromethane) was 6 mg.

Compound 62. 8-(trifluoromethoxy)-2H,4H-spiro[benzo[b]pyrido[4,3-e]-[1,4]thiazine-3,1'-cyclopropan]-1(5H)-one A solution of 2-{[2-amino-5-(trifluoromethoxy)phenyl]disulfanyl}-4-(trifluoromethoxy)aniline (IIb-2) (30 mg, 0.072 mmol) and 4-azaspiro[2.5]-octane-5,7-dione (III-62) (30 mg, 0.216 mmol) in ethanol (2 ml) containing catalytic amount of triethylamine (2 drops) was refluxed for 16 hours. After completion of the reaction the mixture was concentrated to dryness under reduced pressure. The yield after flash chromatography (100-200 mesh size silica gel, 2% methanol in dichloromethane) was 4 mg.

Compound 63. N-(1-oxo-3-(pyridin-2-yl)-8-(trifluoromethoxy)-1,3,4,5-tetrahydro-2H-benzo[b]pyrido[4,3-e][1,4]thiazin-2-yl)acetamide A solution of 2-{[2-amino-5-(trifluoromethoxy)phenyl]disulfanyl}-4-(trifluoromethoxy)aniline (IIb-2) (20 mg, 0.048 mmol) and 1-acetamino-6-(pyridin-2-yl)piperidine-2,4-dione (III-63) (24 mg, 0.096 mmol) in ethanol (1 ml) containing catalytic amount of triethylamine (2 drops) was refluxed for 16 hours. After completion of the reaction the mixture was concentrated to dryness under reduced pressure. The yield after preparative-TLC (10% methanol in dichloromethane) was 10 mg.

Compound 64. 2-amino-3-(pyridin-2-yl)-8-(trifluoromethoxy)-3,4-dihydro-2H-benzo[b]pyrido[4,3-e][1,4]thiazin-1(5H)-one Compound 63 (14 mg, 0.032 mmol) was dissolved in methanol (1 ml). Concentrated HCl (0.3 ml) was added and the resulting mixture stirred at 60° C. for 5 hours. The reaction was quenched by adding saturated $NaHCO_3$ and extracted with dichloromethane. The organic layer was dried over sodium sulphate and concentrated under reduced pressure. The solids were washed with dichloromethane:n-pentane mixture. The yields after drying was 3 mg.

Compound 65. N-(7-chloro-8-methoxy-1-oxo-3-(pyridin-2-yl)-1,3,4,5-tetrahydro-2H-benzo[b]pyrido[4,3-e][1,4]thiazin-2-yl)acetamide A solution of 2-[(2-amino-4-chloro-5-methoxyphenyl)disulfanyl]-5-chloro-4-methoxyaniline (IIb-1) (80 mg, 0.213 mmol) and 1-acetamino-6-(pyridin-2-yl)piperidine-2,4-dione (III-63) (105 mg, 0.425 mmol) in ethanol (2 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 9 mg.

Compound 66. N-(1-oxo-8-(trifluoromethoxy)-1,2',3',5,5',6'-hexahydro-2H,4H-spiro[benzo[b]pyrido[4,3-e][1,4]thiazine-3,4'-pyran]-2-yl)acetamide A solution of 2-{[2-amino-5-(trifluoromethoxy)phenyl]disulfanyl}-4-(trifluoromethoxy)aniline (IIb-2) (100 mg, 0.24 mmol) and N-{2,4-dioxo-9-oxa-1-azaspiro[5.5]undecan-1-yl}acetamide (III-66) (115 mg, 0.48 mmol) in ethanol (4 ml) containing catalytic amount of triethylamine (3 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 80 mg.

Compound 67. 2-amino-8-(trifluoromethoxy)-2',3',5',6'-tetrahydro-2H,4H-spiro[benzo[b]pyrido[4,3-e][1,4]thiazine-3,4'-pyran]-1(5H)-one Compound 66 (50 mg, 0.117 mmol) was dissolved in methanol (2 ml). Concentrated HCl (0.5 ml) was added and the resulting mixture stirred at 60° C. for 5 hours. The reaction was quenched by adding saturated $NaHCO_3$ and extracted with dichloromethane. The organic layer was dried over sodium sulphate and concentrated under reduced pressure. The solids were washed with dichloromethane:n-pentane mixture. The yield after drying was 30 mg.

Compound 68. N-(7-chloro-8-methoxy-1-oxo-1,2',3',5,5',6'-hexahydro-2H,4H-spiro[benzo[b]pyrido[4,3-e][1,4]thiazine-3,4'-pyran]-2-yl)acetamide A solution of 2-[(2-amino-4-chloro-5-methoxyphenyl)disulfanyl]-5-chloro-4-methoxyaniline (IIb-1) (200 mg, 0.53 mmol) and N-{2,4-dioxo-9-oxa-1-azaspiro[5.5]undecan-1-yl}acetamide (III-66) (255 mg, 1.06 mmol) in ethanol (8 ml) containing catalytic amount of triethylamine (4 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 220 mg.

Compound 69. N-(8-methoxy-1-oxo-1,2',3',5,5',6'-hexahydro-2H,4H-spiro-[benzo[b]pyrido[4,3-e][1,4]thiazine-3,4'-pyran]-2-yl)acetamide A solution of 2-[(2-amino-5-methoxyphenyl)disulfanyl]-4-methoxyaniline (IIb-4) (200 mg, 0.65 mmol) and N-{2,4-dioxo-9-oxa-1-azaspiro-[5.5]undecan-1-yl}acetamide (III-66) (312 mg, 1.30 mmol) in ethanol (8 ml) containing catalytic amount of triethylamine (4 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 270 mg.

Compound 70. N-(8-methoxy-1-oxo-3-(pyridin-2-yl)-1,3,4,5-tetrahydro-2H-benzo[b]pyrido[4,3-e][1,4]thiazin-2-yl)acetamide A solution of 2-[(2-amino-5-methoxyphenyl)disulfanyl]-4-methoxyaniline (IIb-4) (80 mg, 0.26 mmol) and 1-acetamino-6-(pyridin-2-yl)piperidine-2,4-dione (III-63) (128 mg, 0.52 mmol) in ethanol (2 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 10 mg.

Compound 71. 2-amino-7-chloro-8-methoxy-2',3',5',6'-tetrahydro-2H,4H-spiro[benzo[b]pyrido[4,3-e][1,4]thiazine-3,4'-pyran]-1(5H)-one Compound 68 (170 mg, 0.416 mmol) was dissolved in methanol (8 ml). Concentrated HCl (1 ml) was added and the resulting mixture stirred at 60° C. for 5 hours. The reaction was quenched by adding saturated NaHCO$_3$ and extracted with dichloromethane. The organic layer was dried over sodium sulphate and concentrated under reduced pressure. The yield after prep-TLC (8% MeOH in DCM) was 10 mg.

Compound 72. 2-amino-8-methoxy-2',3',5',6'-tetrahydro-2H,4H-spiro-[benzo[b]pyrido[4,3-e][1,4]thiazine-3,4'-pyran]-1(5H)-one Compound 69 (220 mg, 0.587 mmol) was dissolved in methanol (10 ml). Concentrated HCl (1.5 ml) was added and the resulting mixture stirred at 60° C. for 5 hours. The reaction was quenched by adding saturated NaHCO$_3$ and extracted with dichloromethane. The organic layer was dried over sodium sulphate and concentrated under reduced pressure. The solids were washed with dichloromethane:n-pentane mixture. The yield after drying was 50 mg.

Compound 73. 7-chloro-8-methoxy-2H,4H-spiro[benzo[b]pyrido[4,3-e]-[1,4]thiazine-3,1'-cyclopropan]-1(5H)-one A solution of 2-[(2-amino-4-chloro-5-methoxyphenyl)disulfanyl]-5-chloro-4-methoxyaniline (IIb-1) (75 mg, 0.20 mmol) and 4-azaspiro[2.5]octane-5,7-dione (III-62) (555 mg, 0.40 mmol) in ethanol (4 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 4 mg.

Compound 74. 8-methoxy-2H,4H-spiro[benzo[b]pyrido[4,3-e][1,4]thiazine-3,1'-cyclopropan]-1(5H)-one A solution of 2-[(2-amino-5-methoxyphenyl)disulfanyl]-4-methoxyaniline (IIb-4) (75 mg, 0.24 mmol) and 4-azaspiro[2.5]octane-5,7-dione (III-62) (68 mg, 0.48 mmol) in ethanol (4 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 5 mg.

Compound 75. 3,3-dimethyl-2-(methyl(prop-2-yn-1-yl)amino)-8-(trifluoromethoxy)-3,4-dihydro-2H-benzo[b]pyrido[4,3-e][1,4]thiazin-1(5H)-one Propargyl bromide (10 mg, 0.08 mmol) was added to a stirred mixture of compound 61 (15 mg, 0.04 mmol) and K$_2$O0$_3$ (7 mg, 0.05 mmol) in DMF (1 ml) at RT. The resulting mixture was stirred at RT for 4 hours. The mixture was poured in an ice water and extracted with ethyl acetate. The organic phase was washed with water, dried over sodium sulphate and concentrated under reduced pressure. The yield after preparative TLC (30% ethyl acetate in hexane) was 2.5 mg.

Compound 76. 2-(dimethylamino)-8-(trifluoromethoxy)-2',3',5',6'-tetrahydro-2H,4H-spiro[benzo[b]pyrido[4,3-e][1,4]thiazine-3,4'-pyran]-1(5H)-one Methyl iodide (44 mg, 0.31 mmol) was added to the mixture of Compound 67 (40 mg, 0.103 mmol) and K$_2$CO$_3$ (21 mg, 0.155 mmol) in DMF (1 ml). The resulting mixture was stirred at RT for 4 hours. Brine was added to the mixture and the resulting mixture was extracted with dichloromethane. The organic phase was dried over sodium sulphate and concentrated under reduced pressure. The yield after preparative-TLC (30% ethyl acetate in hexane) was 1 mg.

Compound 77. 2-(methylamino)-8-(trifluoromethoxy)-2',3',5',6'-tetrahydro-2H,4H-spiro[benzo[b]pyrido[4,3-e][1,4]thiazine-3,4'-pyran]-1(5H)-one Methyl iodide (44 mg, 0.31 mmol) was added to the mixture of Compound 67 (40 mg, 0.103 mmol) and K$_2$CO$_3$ (21 mg, 0.155 mmol) in DMF (1 ml). The resulting mixture was stirred at RT for 4 hours. Brine was added to the mixture and the resulting mixture was extracted with dichloromethane. The organic phase was dried over sodium sulphate and concentrated under reduced pressure. The yield after preparative-TLC (30% ethyl acetate in hexane) was 3 mg.

Compound 78. N-(1-oxo-8-(trifluoromethoxy)-1,5-dihydro-2H,4H-spiro-[benzo[b]pyrido[4,3-e][1,4]thiazine-3,1'-cyclopentan]-2-yl)acetamide A solution of 2-{[2-amino-5-(trifluoromethoxy)phenyl]disulfanyl}-4-(trifluoromethoxy)aniline (IIb-2) (50 mg, 0.12 mmol) and 1-acetamino-6-azaspiro[4.5]decane-7,9-dione (III-78) (54 mg, 0.24 mmol) in ethanol (2 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield after prep-TLC (5% methanol in dichloromethane) was 3 mg.

Compound 79. 7-chloro-3,3-dimethyl-8-(trifluoromethoxy)-3,4-dihydro-2H-benzo[b]pyrido[4,3-e][1,4]thiazin-1(5H)-one A solution of 2-[(2-amino-4-chloro-5-trifluoromethoxyphenyl)-disulfanyl]-5-chloro-4-trifluoromethoxyaniline (IIb-79) (100 mg, 0.207 mmol) and 6,6-dimethylpiperidine-2,4-dione (III-1) (58 mg, 0.413 mmol) in ethanol (2 ml) containing catalytic amount of triethylamine (3 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 60 mg.

Compound 80. 7-chloro-3-methyl-8-(trifluoromethoxy)-3,4-dihydro-2H-benzo[b]pyrido[4,3-e][1,4]thiazin-1(5H)-one A solution of 2-[(2-amino-4-chloro-5-trifluoromethoxyphenyl)-disulfanyl]-5-chloro-4-trifluoromethoxyaniline (IIb-79) (100 mg, 0.207 mmol) and 6-methylpiperidine-2,4-dione (III-32) (52 mg, 0.413 mmol) in ethanol (2 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 45 mg.

Compound 81. 4,4-dimethyl-8-(trifluoromethoxy)-2H,4H-spiro[benzo[b]-pyrido[4,3-e][1,4]thiazine-3,1'-cyclopropan]-1(5H)-one A solution of 2-{[2-amino-5-(trifluoromethoxy)phenyl]disulfanyl}-4-(trifluoromethoxy)aniline (IIb-2) (50 mg, 0.12 mmol) and 8,8-Dimethyl-4-azaspiro[2.5]octane-5,7-dione (III-81) (40 mg, 0.24 mmol) in ethanol (3 ml) containing catalytic amount of triethylamine (3 drops) was refluxed for 18 hours. After completion of the reaction the mixture was concentrated to dryness under reduced pressure. The yield after preparative-TLC (30% ethyl acetate in hexane) was 7 mg.

Compound 82. 2-chloro-5,5-dimethyl-10-(trifluoromethoxy)-5,7-dihydro-6H-pyrimido[5,4-c]phenothiazine A catalytic amount of DMF was added to a mixture of Compound 95 (40 mg, 0.104 mmol) in POCl$_3$ (2 ml). The mixture was stirred at 110° C. for 24 hours. After cooling to RT the solvent was removed under reduced pressure. Water was added and the pH was adjusted to 7-8. The aqueous phase was extracted with dichloromethane. The organic layer was dried over sodium sulphate and evaporated under reduced pressure. The yield after preparative-TLC (2% methanol in dichloromethane) was 2.5 mg.

Compound 83. 7-chloro-4,4-dimethyl-8-(trifluoromethoxy)-2H,4H-spiro-[benzo[b]pyrido[4,3-e][1,4]thiazine-3,1'-cyclopropan]-1(5H)-one A solution of 2-[(2-amino-4-chloro-5-trifluoromethoxyphenyl)-disulfanyl]-5-chloro-4-trifluoromethoxyaniline (IIb-79) (50 mg, 0.10 mmol) and 8,8-Dimethyl-4-azaspiro[2.5]octane-5,7-dione (III-81) (35 mg, 0.20 mmol) in ethanol (3 ml) containing catalytic amount of triethylamine (3 drops) was refluxed for 24 hours. After completion of the reaction the mixture was concentrated to dryness under reduced pressure. The yield after preparative-TLC (30% ethyl acetate in hexane) was 4.5 mg.

Compound 84. 2-chloro-5,5-dimethyl-10-(trifluoromethoxy)-5,7-dihydro-6H-pyrimido[5,4-c]phenothiazine A catalytic amount of DMF was added to a mixture of Compound 95 (40 mg, 0.104 mmol) in POCl$_3$ (2 ml). The mixture was stirred at 110° C. for 24 hours. After cooling to RT the solvent was removed under reduced pressure. Water was added and the pH was adjusted to 7-8. The aqueous phase was extracted with dichloromethane. The organic layer was dried over sodium sulphate and evaporated under reduced pressure. The yield after preparative-TLC (2% methanol in dichloromethane) was 3.5 mg.

Compound 85. 7-chloro-4,4-dimethyl-8-(trifluoromethoxy)-2H,4H-spiro-[benzo[b]pyrido[4,3-e][1,4]thiazine-3,1'-cyclopropan]-1(5H)-one 10-oxide A solution of 2-[(2-amino-4-chloro-5-methoxyphenyl)disulfanyl]-5-chloro-4-methoxyaniline (IIb-1) (20 mg, 0.13 mmol) and 8,8-Dimethyl-4-azaspiro[2.5]octane-5,7-dione (III-81) (45 mg, 0.26 mmol) in ethanol (1 ml) containing catalytic amount of triethylamine (3 drops) was refluxed for 24 hours. After completion of the reaction the mixture was concentrated to dryness under reduced pressure. The yield after preparative-TLC (30% ethyl acetate in hexane) was 3 mg.

Compound 86. 7-chloro-8-(trifluoromethoxy)-2H,4H-spiro[benzo[b]-pyrido[4,3-e][1,4]thiazine-3,1'-cyclopentan]-1(5H)-one A solution of 2-[(2-amino-4-chloro-5-trifluoromethoxyphenyl)-disulfanyl]-5-chloro-4-trifluoromethoxyaniline (IIb-79) (50 mg, 0.103 mmol) and 6-azaspiro[4.5]decane-7,9-dione (III-14) (35 mg, 0.207 mmol) in ethanol (2 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 7 mg.

Compound 87. 7-chloro-8-(trifluoromethoxy)-2',3',5',6'-tetrahydro-2H,4H-spiro[benzo[b]pyrido[4,3-e][1,4]thiazine-3,4'-pyran]-1(5H)-one A solution of 2-[(2-amino-4-chloro-5-trifluoromethoxyphenyl)-disulfanyl]-5-chloro-4-trifluoromethoxyaniline (IIb-79) (50 mg, 0.103 mmol) and 9-oxa-1-azaspiro[5.5]undecane-2,4-dione (III-15) (35 mg, 0.207 mmol) in ethanol (2 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 30 mg.

Compound 88. 7-chloro-3-phenyl-8-(trifluoromethoxy)-3,4-dihydro-2H-benzo[b]pyrido[4,3-e][1,4]thiazin-1(5H)-one A solution of 2-[(2-amino-4-chloro-5-trifluoromethoxyphenyl)-disulfanyl]-5-chloro-4-trifluoromethoxyaniline (IIb-79) (50 mg, 0.103 mmol) and 6-phenylpiperidine-2,4-dione (III-31) (39 mg, 0.207 mmol) in ethanol (2 ml) containing catalytic amount of triethylamine (2 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 28 mg.

Compound 89. N-(7-chloro-1-oxo-8-(trifluoromethoxy)-1,2',3',5,5',6'-hexahydro-2H,4H-spiro[benzo[b]pyrido[4,3-e][1,4]thiazine-3,4'-pyran]-2-yl)-acetamide A solution of 2-[(2-amino-4-chloro-5-trifluoromethoxyphenyl)-disulfanyl]-5-chloro-4-trifluoromethoxyaniline (IIb-79) (100 mg, 0.207 mmol) and N-{2,4-dioxo-9-oxa-1-azaspiro[5.5]undecan-1-yl}acetamide (III-66) (99 mg, 0.413 mmol) in ethanol (4 ml) containing catalytic amount of triethylamine (3 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 25 mg.

Compound 90. N-(7-chloro-3,3-dimethyl-1-oxo-8-(trifluoromethoxy)-1,3,4,5-tetrahydro-2H-benzo[b]pyrido[4,3-e][1,4]thiazin-2-yl)acetamide A solution of 2-[(2-amino-4-chloro-5-trifluoromethoxyphenyl)-disulfanyl]-5-chloro-4-trifluoromethoxyaniline (IIb-79) (100 mg, 0.207 mmol) and 1-acetoamino-6,6-dimethylpiperidine-2,4-dione (III-41) (82 mg, 0.413 mmol) in ethanol (2 ml) containing catalytic amount of triethylamine (3 drops) was refluxed for 16 hours. After completion of the reaction the mixture was concentrated to dryness under reduced pressure. The residue was crystallized from dichloromethane:n-pentane mixture. The solids were collected, washed with n-pentane and diethyl ether and dried under reduced pressure. The yield was 30 mg.

Compound 91. 2-chloro-7,7-dimethyl-7,8-dihydro-5H-pyrido[3,4-b]-pyrimido[5,4-e][1,4]thiazin-9(6H)-one A solution of 5-amino-2-chloropyrimidine-4-thiol (IIb-91) (50 mg, 0.31 mmol) and 6,6-dimethylpiperidine-2,4-dione (III-1) (44 mg, 0.31 mmol) in ethanol (2 ml) containing catalytic amount of triethylamine (3 drops) was refluxed for 16 hours. After completion of the reaction the mixture was concentrated to dryness under reduced pressure. The yield after preparative-TLC (2% methanol in dichloromethane) and washing of the solids with n-pentane was 4 mg.

Compound 92. 2-chloro-4-methoxy-7,7-dimethyl-7,8-dihydro-5H-pyrido-[3,4-b]pyrimido[5,4-e][1,4]thiazin-9(6H)-one A solution of crude 5-amino-2-chloro-6-methoxypyrimidine-4-thiol (IIb-92) (50 mg, 0.26 mmol) and 6,6-dimethylpiperidine-2,4-dione (III-1) (37 mg, 0.26 mmol) in ethanol (3 ml) containing catalytic amount of triethylamine (3 drops) was refluxed for 16 hours. After completion of the reaction the mixture was concentrated to dryness under reduced pressure. The yield after preparative-TLC (2% methanol in dichloromethane) and washing of the solids with n-pentane was 7 mg.

Compound 93. 2-((3,3-dimethyl-1-oxo-8-(trifluoromethoxy)-1,3,4,5-tetrahydro-2H-benzo[b]pyrido[4,3-e][1,4]thiazin-2-yl)amino)acetonitrile $K_2CO_3$ (40 mg, 0.29 mmol) was added to a stirred solution of Compound 43 (100 mg, 0.29 mmol) in DMF (1 ml). Bromoacetonitrile (70 mg, 0.58 mmol) was added and the mixture stirred at RT for 16 hours. Water was added and the mixture extracted with dichloromethane. Organic layer was dried over sodium sulphate and evaporated under reduced pressure. The yield after preparative-TLC (50% ethyl acetate in n-hexane) followed by washing with n-pentane was 11 mg.

Compound 94. 2-((1-oxo-8-(trifluoromethoxy)-1,2',3',5,5',6'-hexahydro-2H,4H-spiro[benzo[b]pyrido[4,3-e][1,4]thiazine-3,4'-pyran]-2-yl)amino)-acetonitrile $K_2CO_3$ (7 mg, 0.052 mmol) was added to a stirred solution of Compound 67 (20 mg, 0.052 mmol) in DMF (0.5 ml). Bromoacetonitrile (12 mg, 0.103 mmol) was added and the mixture stirred at RT for 16 hours. Water was added and the mixture extracted with dichloromethane. Organic layer was dried over sodium sulphate and evaporated under reduced pressure. The yield after preparative-TLC (50% ethyl acetate in n-hexane) followed by washing with n-pentane was 3 mg.

Compound 95. 5,5-dimethyl-10-(trifluoromethoxy)-5,7-dihydro-1H-pyrimido[5,4-c]phenothiazin-2(6H)-one A solution of 2-{[2-amino-5-(trifluoromethoxy)phenyl]disulfanyl}-4-(trifluoromethoxy)aniline (IIb-2) (100 mg, 0.24 mmol) and 5,5-dimethyl-1,2,5,6,7,8-hexahydroquinazoline-2,7-dione (III-95) (92 mg, 0.48 mmol) in ethanol (3 ml) containing catalytic amount of triethylamine (4 drops) was refluxed for 16 hours. After completion of the reaction the mixture was concentrated to dryness under reduced pressure. The yield after flash chromatography (100-200 mesh size silica gel, 3-5% methanol in dichloromethane) was 50 mg.

Compound 96. 5,5-dimethyl-10-(trifluoromethoxy)-5,7-dihydro-1H-pyrimido[5,4-c]phenothiazine-2,6-dione Compound 96 was formed as a side product in the synthesis of Compound 95. The yield after flash chromatography (100-200 mesh size silica gel, 3-5% methanol in dichloromethane) was 4 mg.

Compound 97. 9-chloro-5,5-dimethyl-10-(trifluoromethoxy)-5,7-dihydro-1H-pyrimido[5,4-c]phenothiazin-2(6H)-one A solution of 2-[(2-amino-4-chloro-5-trifluoromethoxyphenyl)-disulfanyl]-5-chloro-4-trifluoromethoxyaniline (IIb-79) (200 mg, 0.41 mmol) and 5,5-dimethyl-1,2,5,6,7,8-hexahydroquinazoline-2,7-dione (III-95) (158 mg, 0.82 mmol) in ethanol (5 ml) and triethylamine (0.35 ml) was refluxed for 36 hours. The mixture was concentrated to dryness under reduced pressure. The crude material was purified using flash chromatography (100-200 mesh size silica gel, 5-10% methanol in dichloromethane). The fraction containing the correct product mass was collected and concentrated under reduced pressure. Ethyl acetate was added and the organic phase was washed with water, dried over sodium sulphate and concentrated under reduced pressure. The obtained solids were washed with n-pentane and dried under reduced pressure. The yield was 13 mg.

Compound 98. 4'-methoxy-2'-(methylthio)-5'H,6'H-spiro[cyclopentane-1,7'-pyrido[3,4-b]pyrimido[5,4-e][1,4]thiazin]-9'(8'H)-one A solution of crude 5-amino-2-chloro-6-methoxypyrimidine-4-thiol (IIb-92) (114 mg, 0.60 mmol) and 6-azaspiro[4.5]decane-7,9-dione (III-14) (50 mg, 0.30 mmol) in ethanol (2 ml) containing catalytic amount of triethylamine (4 drops) was refluxed for 16 hours. After completion of the reaction the mixture was concentrated to dryness under reduced pressure. The yield after preparative-TLC (visually orange spot was isolated) and washing of the solids with n-pentane was 10 mg.

Compound 99. 4-methoxy-2-(methylthio)-7-phenyl-7,8-dihydro-5H-pyrido-[3,4-b]pyrimido[5,4-e][1,4]thiazin-9(6H)-one A solution of crude 5-amino-2-chloro-6-methoxypyrimidine-4-thiol (IIb-92) (101 mg, 0.53 mmol) and 6-phenylpiperidine-2,4-dione (III-31) (50 mg, 0.265 mmol) in ethanol (2 ml) containing catalytic amount of triethylamine (4 drops) was refluxed for 16 hours. After completion of the reaction the mixture was concentrated to dryness under reduced pressure. The yield after preparative-TLC (visually orange spot was isolated) and washing of the solids with n-pentane was 8 mg.

EXPERIMENTS

The compounds of the present invention limit the damage caused by lipid hydroperoxides, act as cytoprotectants in various cell death models in vitro, suppress the production of inflammatory mediator and provide protection against neurotoxin in vivo. Said properties are demonstrated with the pharmacological experiments described below.

Experiment 1. Determination of Efficacy Against the Cytotoxicity of Linoleic Acid Hydroperoxide (LOOH)

The compounds were tested for their potency to limit LOOH induced cell death in undifferentiated PC12 cells according to the method of Sasaki et al. 2003 with slight modifications. Undifferentiated PC12 cells (ATCC) were plated in 96-well plates at the density of 10,000 cells/well in 100 µl medium (Dulbecco's Modified Eagle Medium GlutaMAX Gibco, supplemented with 5% fetal bovine serum and 5% horse serum). Medium was replaced 48 h after plating with 100 µl serum-free medium containing various concentrations of LOOH to first establish dose response for LOOH induced cell death. The concentration of LOOH that yielded 70-90% cytotoxicity was selected for screening potential cytoprotective effects of compounds of the present invention.

Compounds were first dissolved in 100% DMSO at 10 mM and then diluted with culture medium to appropriate working solutions. Compounds were studied at concentrations of 0, 80 nM, 400 nM, 2000 nM, and 10 000 nM. Compounds were plated on cells at the same time as LOOH was added. Controls included cells exposed to plain medium (scaled to 100% viability), LOOH only, or study compounds alone without LOOH to assess potential cytotoxicity of the study compounds on PC12 cells. After 24-h incubation resazurin viability assay was performed.

Resazurin is a dye producing highly fluorescent resorufin when reduced by oxidoreductases within viable cells. Measurement of resazurin fluorescence is therefore an indicator of the viability of the cell. Following the LOOH exposure, medium was removed and replaced with 100 µl of 10 µM pre-warmed resazurin (Sigma). The working solution of resazurin was prepared from 50 mM resazurin in Hank's Buffered Salt Solution stock solution. The plates were incubated for 2 h at 37° C., 5% $CO_2$. Resorufin fluorescence was measured at 530 nm/590 nm (excitation/emission) using Victor 1420 multilabel reader. Data were saved in Excel format. The fluorescence of the blank (no cells) was subtracted from all values. Control wells which contained cells that were not exposed to LOOH were normalized to 100%. The data were presented as a percentage of viable cells as a function of compound concentration (in the presence or absence of LOOH). The study compounds were tested in 6 parallel wells at each concentration.

Student's T-test was used to determine whether the difference between the means for two measurement groups (treatment group at selected concentration vs. vehicle treated cells) was statistically significant.

Figure 1B:
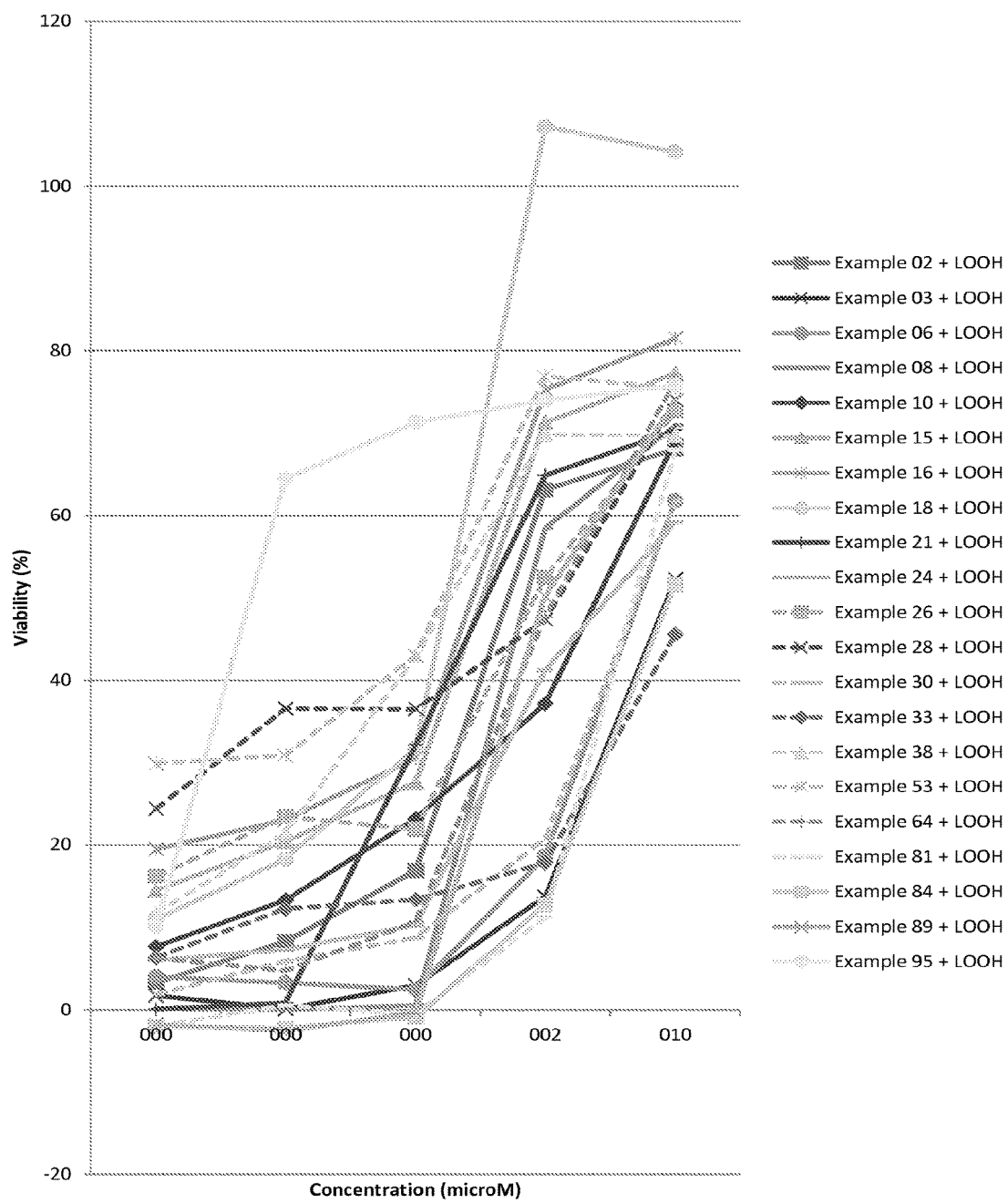

The results are presented in FIGS. 1A and 1B. The results show that the compounds of the present invention are capable of limiting LOOH induced cytotoxicity. Data also show that the compounds of the present invention are not cytotoxic to PC12 cells when incubated on PC12 cells without LOOH.

Experiment 2. Determination of Efficacy Against the Cytotoxicity of Paraquat/Sodium Nitroprusside Combination Reactive oxygen species (ROS) and reactive nitrogen species (RNS) are known to induce formation of lipid hydroperoxides. PC12 cells were therefore exposed to a combined ROS/RNS injury in order to generate a model system for studying efficacies of compounds capable of limiting lipid hydroperoxide cytotoxicity. Cell culture methods similar to Experiment 1 were used except that a combination of superoxide donor (paraquat, PQ, Aldrich) and nitric oxide releasing sodium nitroprusside (SNP, Sigma) was used as toxin. Paraquat and SNP (both at 100 µM final concentration) were mixed and plated on PC12 cells at the same time with study compounds. Resazurin viability assay was performed 24 h later as described above.

Figure 2A:
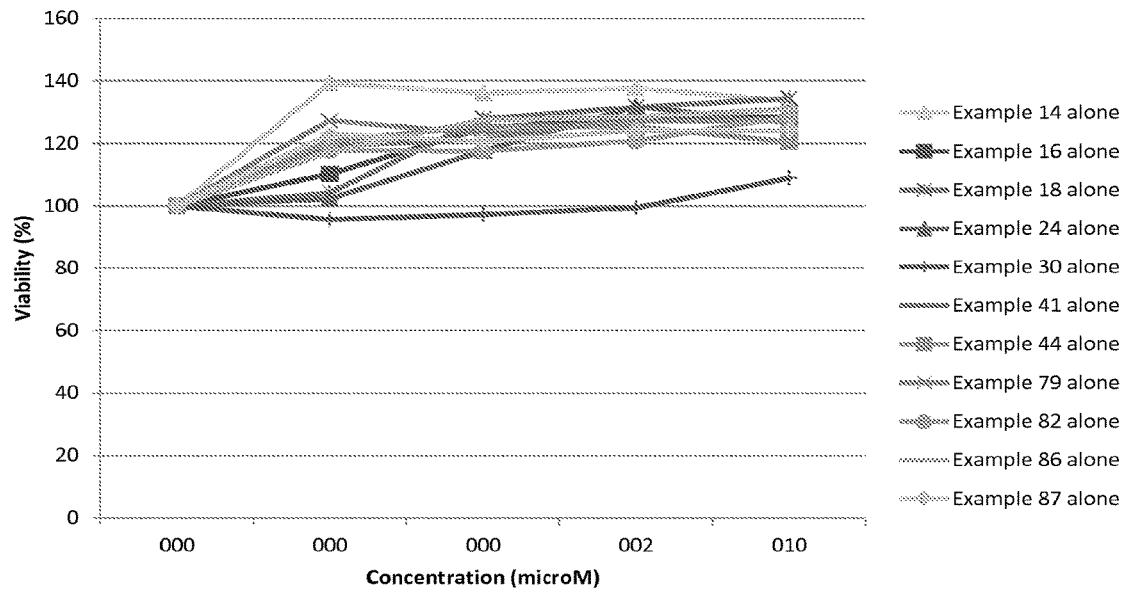
FIG. 2A, 2B: summarize data showing the percentage of viable cells in the presence of increasing (0-10 µM) concentrations of specified example compounds of the present invention a) alone (FIG. 2A) or b) upon combined paraquat and sodium nitroprusside (PQ+SNP) induced cell death in undifferentiated PC12 cells (FIG. 2B)
Figure 2B:
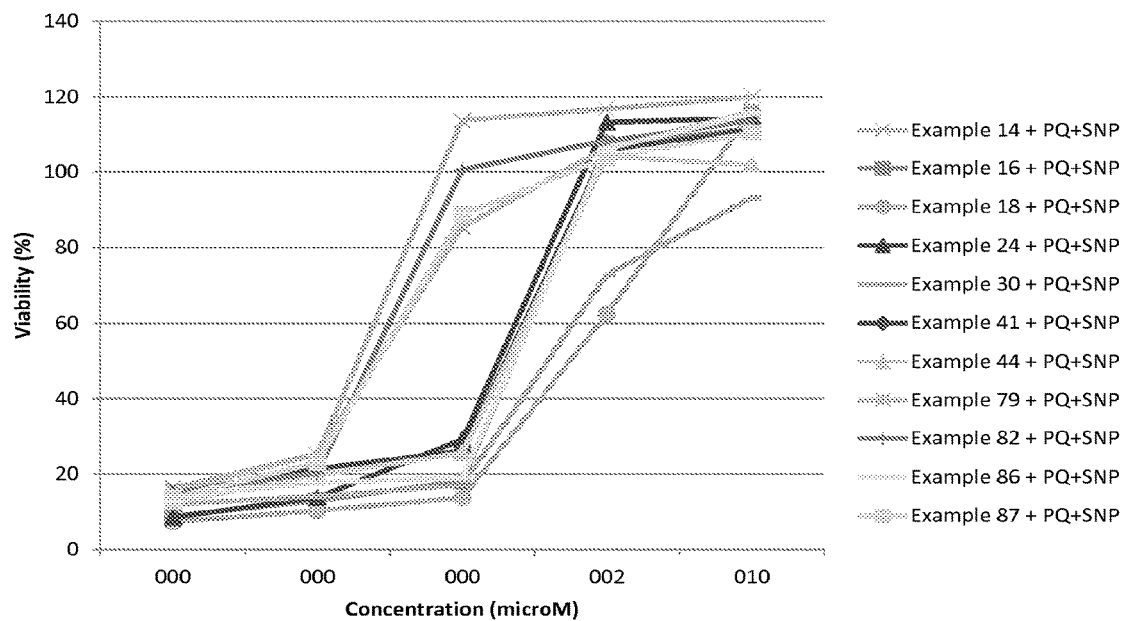

The results are presented in FIGS. 2A and 2B. The results show that the compounds of the present invention are capable of inhibiting oxidativenitrosative stress induced cell death and the compounds of the present invention are not cytotoxic on PC12 cells when incubated on PC12 cells without toxins.

Experiment 3. Determination of Inhibitory Effects Against Lipopolysaccharide Induced Nitric Oxide Release in BV2 Cells Activated glial cells coexist with degenerating neurons in virtually all neurodegenerative diseases. Bacterial lipopolysaccharide (LPS) is a widely used stimulant of glial cells leading to redox imbalance and the release of proinflammatory mediators. Compounds of the present invention were studied for their potency to suppress the production and/or secretion of pro-inflammatory nitric oxide (NO) in microglial BV2 cell line.

The murine microglial BV2 cell line was grown in RPMI-1640 medium containing 10% heat inactivated FBS supplemented with L-glutamine at 4 mM final concentration and 5 µg/ml of gentamicin at 37° C. in a humidified atmosphere of 5% $CO_2$. Cultured BV2 cells were then stimulated with 50 ng/ml LPS (Sigma) for 24 h in the absence or presence of various concentrations (2.5 µM, 5 µM, 10 µM, and 20 µM) of study compounds. NO release was analyzed as nitrite, which is the primary stable and nonvolatile breakdown product of NO, by Griess reagent system (Promega) according to manufacturer's instructions. The viability of BV2 cells, as assessed by resazurin assay as described in Experiment 1, in the presence of increasing concentrations of study compounds was noted to be unchanged. The NO release from BV2 cells exposed to LPS only was normalized to 100%.

Figure 3:
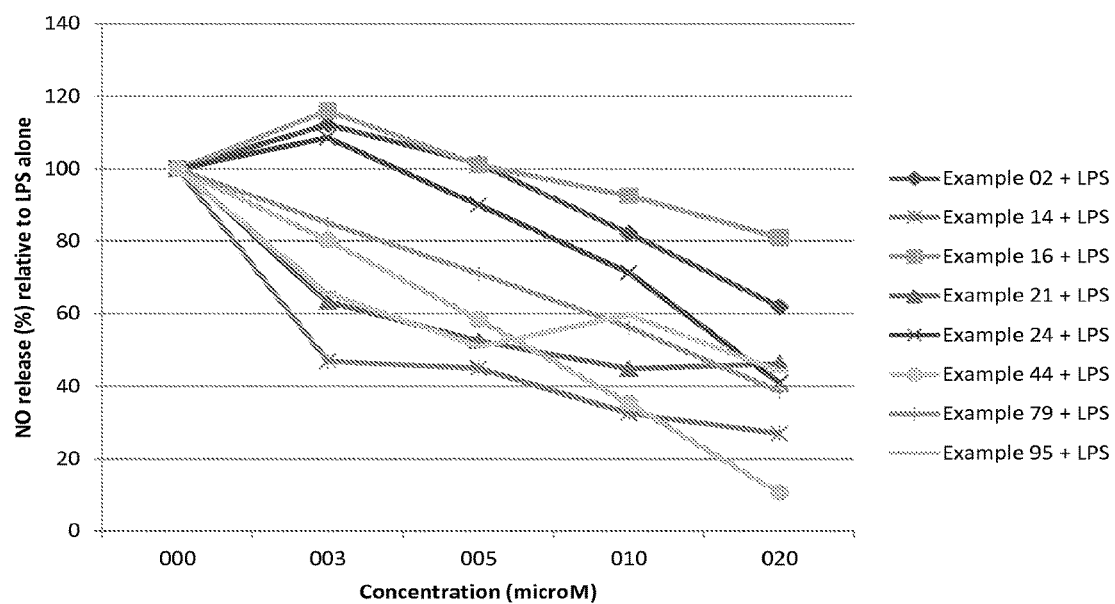
FIG. 3 summarizes data showing the effects of increasing concentrations of specified example compounds of the present invention on nitric oxide (NO) release from microglial BV2 cells upon 50 ng/mL lipopolysaccharide (LPS) stimulation at 24 h time point, NO release from BV2 cells exposed to LPS only was normalized to 100%.

The results are presented in FIG. 3. The results show that the compounds of the present invention are capable of suppressing the production and/or secretion of NO in microglial cells.

Experiment 4. Determination of Neuroprotective Effects in C. Elegans

The protective effects of the compounds of the present invention on the neurotoxicity of 1-methyl-4-phenyl-pyridinium (MPP+) were assessed using C. elegans selectively expressing green fluorescent protein (GFP) in dopaminergic (DA) neurons. MPP+, which is the active metabolite of neurotoxin MPTP, is known to interfere with oxidative phosphorylation in mitochondria resulting in increased lipid peroxidation and eventually cell death.

Transgenic C. elegans integrated strain Is11-7 [Pdat-1: GFP] expressing GFP in its genome under the control of dopamine transporter-1 gene were cultivated and maintained according to the standard protocol. Strain was thawed from freezer vial and placed on freshly prepared Nematode Growth Medium (NGM) that have been spread with Escherichia coli (E. coli) strain OP50 as a food source and allowed to reproduce for several days. Hermaphrodite form of this C. elegans strain has eight DA neurons, six located in the head and two in the tail.

Prior to experiment the culture was synchronized. The NGM plates containing a layer of E. coli OP50 were inoculated with 4-5 drops of L1 worms from previous week experiments and incubated at 15° C. for 4 days. Growth of nematode strains was daily followed with a stereomicroscope (Nikon SMZ645). The eggs carrying adult worms were bleached and the eggs were used for the experiment and also for maintenance of the strain. The eggs for the experiment were grown in liquid medium at 20° C. on rotating shaker at 350 rpm for 14 h to develop to L1 stage. The eggs used for maintenance were stored at 15° C. in incubator up to 2 weeks.

For an assay, a suspension of L1 worms and defined amount of E. coli strain OP50 in NGM was distributed into 96-well plates. A 40-µl suspension contained an average of 40 animals per well. First, a dose response for ascending concentrations of MPP+ (Sigma) was established. MPP+ ranging from 0 to 2 mM concentration (in sterile filtered aqua as the total volume of 50 µl/well) was added to the plates and incubated at 20° C. for 48 h in humidity chamber, and then analyzed. Next, a selected MPP+ concentration (0.75 mM) in the presence or absence of study compounds was added to the plates and incubated at 20° C. for 48 h in humidity chamber on rotating shaker. The compounds were prepared as stock solutions in DMSO, and then diluted to working solutions at the desired concentrations to yield a final volume of 50 µl aqua per well. To assess the neuroprotective effects of compounds, worms were anaesthetized by addition of sodium azide to a concentration of 14 mM. Plates were imaged with a BD pathway 855 High-Content Imager (Becton Dickinson Biosciences) with 10× objective acquiring 25 contiguous fields per well under control of Attovision software (Becton Dickinson Biosciences). Number of worms analyzed per treatment group was approximately 200. Alternatively, the worms were mounted on glass slides to be imaged under 20× objective with a conventional fluorescence microscope (Olympus AX70) attached to Olympus Soft Imaging system. In this case 15 worms per treatment group were analyzed and each individual experiment was repeated 3 to 4 times. GFP fluorescence derived from DA neurons was analyzed either with Attovision software or Image Pro Plus (Media Cybernetics). The data were normalized to the average of GFP fluorescence derived from vehicle treated C. elegans.

Figure 4:
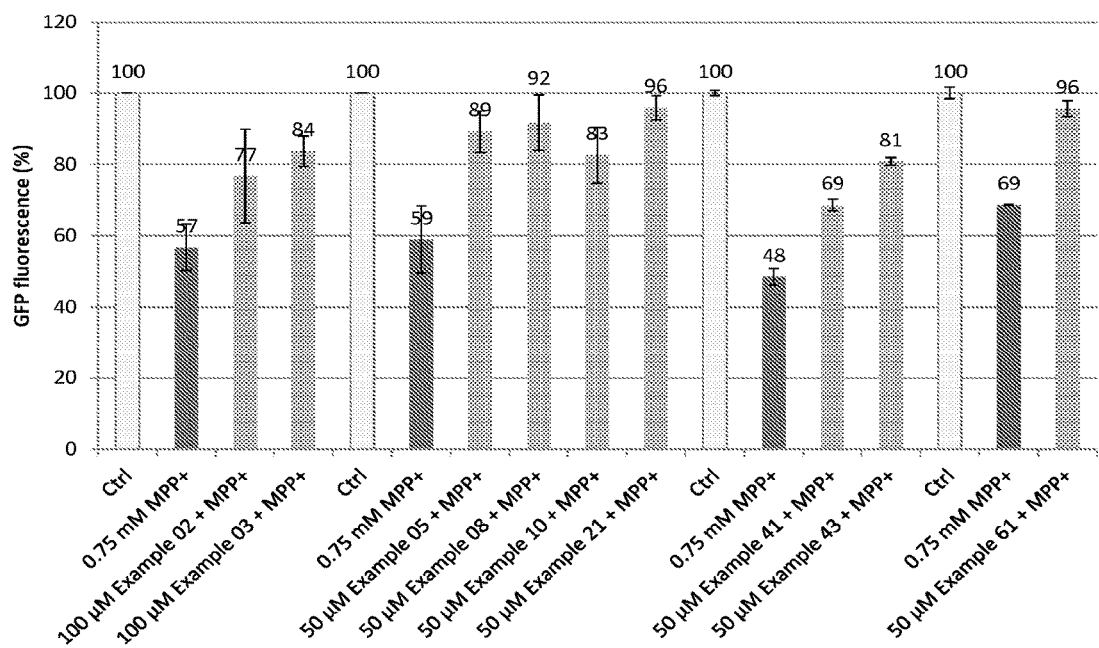
FIG. 4 summarizes data showing the percentage of viable dopaminergic cells upon MPP+-induced cell death in *C. elegans* plated in the presence of specified example compounds of the present invention, the number of viable dopaminergic cells in non-MPP+-treated (ctrl) group was normalized to 100% and the results are presented as mean±SEM.

The results are presented in FIG. 4. The results show that the compounds of the present invention preserve DA neurons in C. elegans exposed to neurotoxin MPP+.

In addition to the experiments described above, the cytoprotective properties of the compounds of the present invention are demonstrated using in vitro model systems in which antioxidant reserves such as glutathione is significantly reduced or depleted by high doses of glutamate or other disease relevant insults, or toxicities are studied in other cell lines or primary cell cultures and standard in vivo models.

The properties of the compounds are also studied in relevant in vitro and in vivo tests for stability, permeability, pharmacological selectivity and specificity, safety, tolerability or toxicity.

It will be obvious to a person skilled in the art that, as the technology advances, the inventive concept can be implemented in various ways. The invention and its embodiments are not limited to the examples described above but may vary within the scope of the claims.

The invention claimed is:
1. A compound of formula (I)

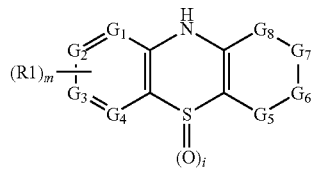

wherein:
(i) G1, G2, G3, and G4 are each C or N, provided that at least one of G1, G2, G3, and G4 is C;
(ii) G5 is C=O; and G6 is N(R6); and
(iii) G7 is C(R7)$_2$; and
(iv) G8 is [CH$_2$]$_k$C(R8)$_2$, C(R8)$_2$CH$_2$, C(R8)$_2$C(R8)$_2$, [CH$_2$]$_n$, or (C=O);
each R1 is independently selected from the group consisting of halogen, cyano, nitro, OR', C$_{1-6}$-(per)haloalkoxy, N(R')$_2$, SR', SOR', SO$_2$R', C$_{1-6}$-alkyl, C$_{1-6}$-(per)haloalkyl, COOR', and CON(R')$_2$; and/or two adjacent R1 together with the ring atoms they are attached to form a 5 to 7 membered ring optionally comprising 1 to 3 heteroatoms selected from N, O, and S;
each R5 is independently selected from the group consisting of halogen, cyano, nitro, OR', oxo, C$_{1-6}$-(per) haloalkoxy, N(R')$_2$, C$_{1-6}$-alkyl, C$_{1-6}$-(per)haloalkyl, COOR', CON(R')$_2$; —[CH$_2$]$_k$Ar, and C$_{1-3}$-alkyl-(C=O)—;
each R6 is independently selected from the group consisting of H, C$_{1-6}$-alkyl, C$_{1-6}$-(per)haloalkyl, C$_{2-6}$-alkenyl, C$_{2-6}$-alkynyl, OR', N(R")$_2$, C$_{1-3}$-alkyl-(C=O)—, C$_{1-3}$-alkyl-(C=O)—NH—, —[CH$_2$]$_k$Ar, and —[CH$_2$]$_k$Cy;
each R7 is independently selected from the group consisting of H, C$_{1-6}$-alkyl, C$_{1-6}$-(per)haloalkyl, OR"—C$_{1-3}$-alkylenyl, N(R')$_2$—C$_{1-3}$-alkylenyl, (R')$_2$NCO—C$_{1-3}$-alkylenyl, COOR', —[CH$_2$]$_k$Ar, and —[CH$_2$]$_k$Cy; or two R7 attached to a same ring carbon form together with the said ring carbon a 3 to 7 membered aliphatic carbocyclic or heterocyclic ring optionally substituted one or two times with R5;
each R8 is independently C$_{1-6}$-alkyl, or C$_{1-6}$-(per)haloalkyl; or two R8 together with the ring carbon they are attached to form a 3 to 7 membered aliphatic or heteroaliphatic ring optionally substituted one or two times with R5;
or one R7 and one R8 located on G7 and G8, respectively, form together a further bond between G7 and G8; and the other R7 and the other R8 are each independently H or as defined above or form together with the ring carbons they are attached to a 5 to 7 membered unsaturated carbocyclic or heterocyclic ring optionally substituted one or two times with R5;
or one R7 and one R8 located on G7 and G8, respectively, form together with the ring carbons they are attached to a 3 to 7 membered aliphatic carbocyclic or heterocyclic ring optionally substituted one or two times with R5; and the other R7 and the other R8 are each H;
each R' is independently H or C$_{1-6}$-alkyl; or when attached to N each R' may alternatively be C$_{1-3}$-alkoxy-C$_{1-3}$-alkylenyl, or two R' may form together with the N they are attached to a 5 to 6 membered saturated heterocyclic ring optionally comprising one further heteroatom selected form N, O and S;
each R" is independently selected from the group consisting of R', CN—C$_{1-3}$-alkylenyl, C$_{1-3}$-alkoxy-C$_{1-3}$-alkylenyl, C$_{1-6}$-alkenyl, C$_{1-6}$-alkynyl, and C$_{1-3}$-alkyl-(C=O)—; or each R" forms together with a R7 or R8, respectively, an C$_{1-3}$-alkylene bridge;
Ar is phenyl or 5 to 6 membered aromatic heterocyclic ring comprising one, two or three N atoms, said phenyl or ring being optionally substituted one or two times with R5;
Cy is 3 to 7 membered aliphatic carbocyclic or heterocyclic ring optionally substituted one or two times with R5;
i is 0, 1, or 2;
k is 0 or 1;
m is 0, 1, 2, 3, or 4;
n is 0, 1, 2, or 3;
or metabolite, N-oxide, pharmaceutically acceptable salt, hydrate, or solvate thereof.
2. The compound of formula (I) as claimed in claim 1, wherein i is 0.
3. The compound of formula (I) as claimed in claim 1, wherein G1, G2, G3, and G4 are each C.
4. The compound of formula (I) as claimed in claim 1, wherein m is 1 or 2.
5. The compound of formula (I) as claimed in claim 1, wherein each R1 is independently selected from the group consisting of halogen, C$_{1-3}$-alkoxy, C$_{1-3}$-(per)haloalkoxy, and di(C$_{1-3}$-alkyl)amino.
6. The compound of formula (I) as claimed in claim 1, wherein G8 is —(C=O)— or [CH$_2$]$_n$; and n is 1 or 2.
7. The compound as claimed in claim 1, wherein the compound is selected from the group consisting of:
7-chloro-8-methoxy-3,3-dimethyl-3,4-dihydro-2H-benzo[b]pyrido[4,3-e][1,4]thiazin-1(5H)-one (1);
3,3-dimethyl-8-(trifluoromethoxy)-3,4-dihydro-2H-benzo[b]pyrido[4,3-e][1,4]thiazin-1(5H)-one (2);
7-chloro-8-(dimethylamino)-3,3-dimethyl-3,4-dihydro-2H-benzo[b]pyrido[4,3-e][1,4]thiazin-1(5H)-one (3);
8-methoxy-3,3-dimethyl-3,4-dihydro-2H-benzo[b]pyrido[4,3-e][1,4]thiazin-1(5H)-one (4);
9-methoxy-2,3,4,5-tetrahydrobenzo[5,6][1,4]thiazino[2,3-c]azepin-1(6H)-one (9);
9-(trifluoromethoxy)-2,3,4,5-tetrahydrobenzo[5,6][1,4]thiazino[2,3-c]azepin-1(6H)-one (10);
3,3-dimethyl-8-(trifluoromethoxy)-2,3-dihydro-4H-benzo[b]pyrido[4,3-e][1,4]thiazine-1,4(5H)-dione (11);
3,3-dimethyl-3,4-dihydro-2H-benzo[b]pyrido[4,3-e][1,4]thiazin-1(5H)-one (12);
3,3-diethyl-8-(trifluoromethoxy)-3,4-dihydro-2H-benzo[b]pyrido[4,3-e][1,4]thiazin-1(5H)-one (13);
8-(trifluoromethoxy)-2H,4H-spiro[benzo[b]pyrido[4,3-e][1,4]thiazine-3,1'-cyclopentan]-1(5H)-one (14);
8-(trifluoromethoxy)-2',3',5',6'-tetrahydro-2H,4H-spiro[benzo[b]pyrido[4,3-e][1,4]thiazine-3,4'-pyran]-1(5H)-one (15);
2-ethyl-3,3-dimethyl-8-(trifluoromethoxy)-3,4-dihydro-2H-benzo[b]pyrido[4,3-e][1,4]thiazin-1(5H)-one (16);
2-ethyl-8-(trifluoromethoxy)-2',3',5',6'-tetrahydro-2H,4H-spiro[benzo[b]pyrido[4,3-e][1,4]thiazine-3,4'-pyran]-1(5H)-one (17);
4,4-dimethyl-8-(trifluoromethoxy)-3,4-dihydro-2H-benzo[b]pyrido[4,3-e][1,4]thiazin-1(5H)-one (18);
2-ethyl-4,4-dimethyl-8-(trifluoromethoxy)-3,4-dihydro-2H-benzo[b]pyrido[4,3-e][1,4]thiazin-1(5H)-one (19);

2,3,3-triethyl-8-(trifluoromethoxy)-3,4-dihydro-2H-benzo[b]pyrido[4,3-e][1,4]thiazin-1(5H)-one (29);
4,4-dimethyl-8-(trifluoromethoxy)-3,4-dihydro-2H-benzo[b]pyrido[4,3-e][1,4]thiazin-1(5H)-one 10-oxide (30);
3-phenyl-8-(trifluoromethoxy)-3,4-dihydro-2H-benzo[b]pyrido[4,3-e][1,4]thiazin-1(5H)-one (31);
3-methyl-8-(trifluoromethoxy)-3,4-dihydro-2H-benzo[b]pyrido[4,3-e][1,4]thiazin-1(5H)-one (32);
3-bromo-8,8-dimethyl-8,9-dihydro-7H-pyrazino[2,3-b]pyrido[4,3-e][1,4]thiazin-6(10H)-one (33);
3-methyl-8-(trifluoromethoxy)-2H-benzo[b]pyrido[4,3-e][1,4]thiazin-1(5H)-one (34);
3-phenyl-8-(trifluoromethoxy)-2H-benzo[b]pyrido[4,3-e][1,4]thiazin-1(5H)-one (35);
3-methoxy-8,8-dimethyl-8,9-dihydro-7H-pyrazino[2,3-b]pyrido[4,3-e][1,4]thiazin-6(10H)-one (36);
8-methoxy-3-methyl-3,4-dihydro-2H-benzo[b]pyrido[4,3-e][1,4]thiazin-1(5H)-one (37);
7-chloro-8-methoxy-3-methyl-3,4-dihydro-2H-benzo[b]pyrido[4,3-e][1,4]thiazin-1(5H)-one (38);
8-methoxy-3-phenyl-3,4-dihydro-2H-benzo[b]pyrido[4,3-e][1,4]thiazin-1(5H)-one (39);
7-chloro-8-methoxy-3-phenyl-3,4-dihydro-2H-benzo[b]pyrido[4,3-e][1,4]thiazin-1(5H)-one (40);
N-(3,3-dimethyl-1-oxo-8-(trifluoromethoxy)-1,3,4,5-tetrahydro-2H-benzo[b]pyrido[4,3-e][1,4]thiazin-2-yl)acetamide (41);
N-(3-methyl-1-oxo-8-(trifluoromethoxy)-1,3,4,5-tetrahydro-2H-benzo[b]pyrido[4,3-e][1,4]thiazin-2-yl)acetamide (42);
2-amino-3,3-dimethyl-8-(trifluoromethoxy)-3,4-dihydro-2H-benzo[b]pyrido[4,3-e][1,4]thiazin-1(5H)-one (43);
2-amino-3-methyl-8-(trifluoromethoxy)-3,4-dihydro-2H-benzo[b]pyrido[4,3-e][1,4]thiazin-1(5H)-one (44);
2-amino-8-methoxy-3,3-dimethyl-3,4-dihydro-2H-benzo[b]pyrido4,3-e][1,4]thiazin-1(5H)-one (45);
N-(8-methoxy-3-methyl-1-oxo-1,3,4,5-tetrahydro-2H-benzo[b]pyrido[4,3-e][1,4]thiazin-2-yl)acetamide (46);
2-amino-8-methoxy-3-methyl-3,4-dihydro-2H-benzo[b]pyrido[4,3-e][1,4]thiazin-1(5H)-one (47);
N-(7-chloro-8-methoxy-3,3-dimethyl-1-oxo-1,3,4,5-tetrahydro-2H-benzo[b]pyrido[4,3-e][1,4]thiazin-2-yl)acetamide (48);
2-amino-7-chloro-8-methoxy-3,3-dimethyl-3,4-dihydro-2H-benzo[b]pyrido[4,3-e][1,4]thiazin-1(5H)-one (49);
N-(7-chloro-8-methoxy-3-methyl-1-oxo-1,3,4,5-tetrahydro-2H-benzo[b]pyrido[4,3-e][1,4]thiazin-2-yl)acetamide (50);
2-amino-7-chloro-8-methoxy-3-methyl-3,4-dihydro-2H-benzo[b]pyrido[4,3-e][1,4]thiazin-1(5H)-one (51);
N-(8-methoxy-3,3-dimethyl-1-oxo-1,3,4,5-tetrahydro-2H-benzo[b]pyrido[4,3-e][1,4]thiazin-2-yl)acetamide (52);
3-ethyl-8-(trifluoromethoxy)-3,4-dihydro-2H-benzo[b]pyrido[4,3-e][1,4]thiazin-1(5H)-one (53);
7-chloro-3-ethyl-8-methoxy-3,4-dihydro-2H-benzo[b]pyrido[4,3-e][1,4]thiazin-1(5H)-one (54);
3-ethyl-8-methoxy-3,4-dihydro-2H-benzo[b]pyrido[4,3-e][1,4]thiazin-1(5H)-one (55);
7-chloro-8-methoxy-3-(pyridin-2-yl)-3,4-dihydro-2H-benzo[b]pyrido[4,3-e][1,4]thiazin-1(5H)-one (56);
3-(pyridin-2-yl)-8-(trifluoromethoxy)-3,4-dihydro-2H-benzo[b]pyrido[4,3-e][1,4]thiazin-1(5H)-one (57);
8-methoxy-3-(pyridin-2-yl)-3,4-dihydro-2H-benzo[b]pyrido[4,3-e][1,4]thiazin-1(5H)-one (58);
3-(pyridin-2-yl)-8-(trifluoromethoxy)-2H-benzo[b]pyrido[4,3-e][1,4]thiazin-1(5H)-one (59);
2-(dimethylamino)-3,3-dimethyl-8-(trifluoromethoxy)-3,4-dihydro-2H-benzo[b]pyrido[4,3-e][1,4]thiazin-1(5H)-one (60);
3,3-dimethyl-2-(methylamino)-8-(trifluoromethoxy)-3,4-dihydro-2H-benzo[b]pyrido[4,3-e][1,4]thiazin-1(5H)-one (61);
8-(trifluoromethoxy)-2H,4H-spiro[benzo[b]pyrido[4,3-e][1,4]thiazine-3,1'-cyclopropan]-1(5H)-one (62);
N-(1-oxo-3-(pyridin-2-yl)-8-(trifluoromethoxy)-1,3,4,5-tetrahydro-2H-benzo[b]pyrido[4,3-e][1,4]thiazin-2-yl)acetamide (63);
2-amino-3-(pyridin-2-yl)-8-(trifluoromethoxy)-3,4-dihydro-2H-benzo[b]pyrido[4,3-e][1,4]thiazin-1(5H)-one (64);
N-(7-chloro-8-methoxy-1-oxo-3-(pyridin-2-yl)-1,3,4,5-tetrahydro-2H-benzo[b]pyrido[4,3-e][1,4]thiazin-2-yl)acetamide (65);
N-(1-oxo-8-(trifluoromethoxy)-1,2',3',5,5',6'-hexahydro-2H,4H-spiro-[benzo[b]pyrido[4,3-e][1,4]thiazine-3,4'-pyran]-2-yl)acetamide (66);
2-amino-8-(trifluoromethoxy)-2',3',5',6'-tetrahydro-2H,4H-spiro[benzo[b]pyrido[4,3-e][1,4]thiazine-3,4'-pyran]-1(5H)-one (67);
N-(7-chloro-8-methoxy-1-oxo-1,2',3',5,5',6'-hexahydro-2H,4H-spiro-[benzo[b]pyrido[4,3-e][1,4]thiazine-3,4'-pyran]-2-yl)acetamide (68);
N-(8-methoxy-1-oxo-1,2',3',5,5',6'-hexahydro-2H,4H-spiro[benzo[b]pyrido[4,3-e][1,4]thiazine-3,4'-pyran]-2-yl)acetamide (69);
N-(8-methoxy-1-oxo-3-(pyridin-2-yl)-1,3,4,5-tetrahydro-2H-benzo[b]pyrido[4,3-e][1,4]thiazin-2-yl)acetamide (70);
2-amino-7-chloro-8-methoxy-2',3',5',6'-tetrahydro-2H,4H-spiro[benzo[b]pyrido[4,3-e][1,4]thiazine-3,4'-pyran]-1(5H)-one (71);
2-amino-8-methoxy-2',3',5',6'-tetrahydro-2H,4H-spiro[benzo[b]pyrido[4,3-e][1,4]thiazine-3,4'-pyran]-1(5H)-one (72);
7-chloro-8-methoxy-2H,4H-spiro[benzo[b]pyrido[4,3-e][1,4]thiazine-3,1'-cyclopropan]-1(5H)-one (73);
8-methoxy-2H,4H-spiro[benzo[b]pyrido[4,3-e][1,4]thiazine-3,1'-cyclopropan]-1(5H)-one (74);
3,3-dimethyl-2-(methyl(prop-2-yn-1-yl)amino)-8-(trifluoromethoxy)-3,4-dihydro-2H-benzo[b]pyrido[4,3-e][1,4]thiazin-1(5H)-one (75);
2-(dimethylamino)-8-(trifluoromethoxy)-2',3',5',6'-tetrahydro-2H,4H-spiro[benzo[b]pyrido[4,3-e][1,4]thiazine-3,4'-pyran]-1(5H)-one (76);
2-(methylamino)-8-(trifluoromethoxy)-2',3',5',6'-tetrahydro-2H,4H-spiro[benzo[b]pyrido[4,3-e][1,4]thiazine-3,4'-pyran]-1(5H)-one (77);
N-(1-oxo-8-(trifluoromethoxy)-1,5-dihydro-2H,4H-spiro[benzo[b]pyrido[4,3-e][1,4]thiazine-3,1'-cyclopentan]-2-yl)acetamide (78);
7-chloro-3,3-dimethyl-8-(trifluoromethoxy)-3,4-dihydro-2H-benzo[b]pyrido[4,3-e][1,4]thiazin-1(5H)-one (79);
7-chloro-3-methyl-8-(trifluoromethoxy)-3,4-dihydro-2H-benzo[b]pyrido[4,3-e][1,4]thiazin-1(5H)-one (80);
4,4-dimethyl-8-(trifluoromethoxy)-2H,4H-spiro[benzo[b]pyrido[4,3-e][1,4]thiazine-3,1'-cyclopropan]-1(5H)-one (81);
7-chloro-4,4-dimethyl-8-(trifluoromethoxy)-2H,4H-spiro[benzo[b]pyrido[4,3-e][1,4]thiazine-3,1'-cyclopropan]-1(5H)-one (83);
7-chloro-4,4-dimethyl-8-(trifluoromethoxy)-2H,4H-spiro[benzo[b]pyrido[4,3-e][1,4]thiazine-3,1'-cyclopropan]-1(5H)-one 10-oxide (85);
7-chloro-8-(trifluoromethoxy)-2H,4H-spiro[benzo[b]pyrido[4,3-e][1,4]thiazine-3,1'-cyclopentan]-1(5H)-one (86);

7-chloro-8-(trifluoromethoxy)-2',3',5',6'-tetrahydro-2H,4H-spiro[benzo[b]pyrido[4,3-e][1,4]thiazine-3,4'-pyran]-1(5H)-one (87);

7-chloro-3-phenyl-8-(trifluoromethoxy)-3,4-dihydro-2H-benzo[b]pyrido[4,3-e][1,4]thiazin-1(5H)-one (88);

N-(7-chloro-1-oxo-8-(trifluoromethoxy)-1,2',3',5,5',6'-hexahydro-2H,4H-spiro[benzo[b]pyrido[4,3-e][1,4]thiazine-3,4'-pyran]-2-yl)acetamide (89);

N-(7-chloro-3,3-dimethyl-1-oxo-8-(trifluoromethoxy)-1,3,4,5-tetrahydro-2H-benzo[b]pyrido[4,3-e][1,4]thiazin-2-yl)acetamide (90);

2-chloro-7,7-dimethyl-7,8-dihydro-5H-pyrido[3,4-b]pyrimido[5,4-e][1,4]thiazin-9(6H)-one (91);

2-chloro-4-methoxy-7,7-dimethyl-7,8-dihydro-5H-pyrido[3,4-b]pyrimido[5,4-e][1,4]thiazin-9(6H)-one (92);

2-((3,3-dimethyl-1-oxo-8-(trifluoromethoxy)-1,3,4,5-tetrahydro-2H-benzo[b]pyrido[4,3-e][1,4]thiazin-2-yl)amino)acetonitrile (93);

2-((1-oxo-8-(trifluoromethoxy)-1,2',3',5,5',6'-hexahydro-2H,4H-spiro-[benzo[b]pyrido[4,3-e][1,4]thiazine-3,4'-pyran]-2-yl)amino)acetonitrile (94);

4'-methoxy-2'-(methylthio)-5'H,6'H-spiro[cyclopentane-1,7'-pyrido[3,4-b]pyrimido[5,4-e][1,4]thiazin]-9'(8'H)-one (98); and 4-methoxy-2-(methylthio)-7-phenyl-7,8-dihydro-5H-pyrido[3,4-b]pyrimido[5,4-e][1,4]thiazin-9(6H)-one (99).

8. A pharmaceutical composition comprising one or more compound(s) as defined in claim 1 together with a pharmaceutically acceptable carrier, diluent, and/or excipient.

9. The pharmaceutical composition as claimed in claim 8 in combination with one or more other active ingredients.

10. A method of treating a condition where elimination of lipid hydroperoxides and/or limiting their detrimental effects on cellular macromolecules is desired and/or a disease or state, either acute or chronic, involving aberrant cellular lipid peroxidation in the central nervous system or in the periphery of the body, comprising administering an effective amount of one or more compound(s) of formula (I)

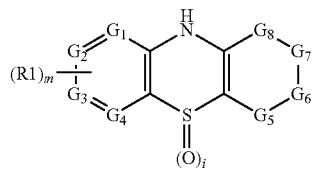

(I)

wherein (i) G1, G2, G3, and G4 are each C or N, provided that at least one of G1, G2, G3, and G4 is C;
(ii) G7 is $C(R7)_2$; and
(iii) G8 is $[CH_2]_kC(R8)_2$, $C(R8)_2CH_2$, $C(R8)_2C(R8)_2$, $[CH_2]_n$, or (C=O);

wherein:
each R1 is independently selected from the group consisting of halogen, cyano, nitro, OR', $C_{1-6}$-(per)haloalkoxy, $N(R')_2$, SR', SOR', $SO_2R'$, $C_{1-6}$-alkyl, $C_{1-6}$-(per)haloalkyl, COOR', and $CON(R')_2$; and/or two adjacent R1 together with the ring atoms they are attached to form a 5 to 7 membered ring optionally comprising 1 to 3 heteroatoms selected from N, O, and S;

each R5 is independently selected from the group consisting of halogen, cyano, nitro, OR', oxo, $C_{1-6}$-(per)haloalkoxy, $N(R')_2$, $C_{1-6}$-alkyl, $C_{1-6}$-(per)haloalkyl, COOR', $CON(R')_2$; $—[CH_2]_kAr$, and $C_{1-3}$-alkyl-(C=O)—;

each R6 is independently selected from the group consisting of H, $C_{1-6}$-alkyl, $C_{1-6}$-(per)haloalkyl, $C_{2-6}$-alkenyl, $C_{2-6}$-alkynyl, OR', $N(R")_2$, $C_{1-3}$-alkyl-(C=O)—, $C_{1-3}$-alkyl-(C=O)—NH—, $—[CH_2]_kAr$, and $—[CH_2]_kCy$;

each R7 is independently selected from the group consisting of H, $C_{1-6}$-alkyl, $C_{1-6}$-(per)haloalkyl, OR"—$C_{1-3}$-alkylenyl, $N(R')_2$—$C_{1-3}$-alkylenyl, $(R')_2NCO$—$C_{1-3}$-alkylenyl, COOR', $—[CH_2]_kAr$, and $—[CH_2]_kCy$; or two R7 attached to a same ring carbon form together with the said ring carbon a 3 to 7 membered aliphatic carbocyclic or heterocyclic ring optionally substituted one or two times with R5;

each R8 is independently $C_{1-6}$-alkyl, or $C_{1-6}$-(per)haloalkyl; or two R8 together with the ring carbon they are attached to form a 3 to 7 membered aliphatic or heteroaliphatic ring optionally substituted one or two times with R5;

or one R7 and one R8 located on G7 and G8, respectively, form together a further bond between G7 and G8; and the other R7 and the other R8 are each independently H or as defined above or form together with the ring carbons they are attached to a 5 to 7 membered unsaturated carbocyclic or heterocyclic ring optionally substituted one or two times with R5;

or one R7 and one R8 located on G7 and G8, respectively, form together with the ring carbons they are attached to a 3 to 7 membered aliphatic carbocyclic or heterocyclic ring optionally substituted one or two times with R5; and the other R7 and the other R8 are each H;

each R' is independently H or $C_{1-6}$-alkyl; or when attached to N each R' may alternatively be $C_{1-3}$-alkoxy-$C_{1-3}$-alkylenyl, or two R' may form together with the N they are attached to a 5 to 6 membered saturated heterocyclic ring optionally comprising one further heteroatom selected form N, O and S;

each R" is independently selected group the group consisting of R', CN—$C_{1-3}$-alkylenyl, $C_{1-3}$-alkoxy-$C_{1-3}$-alkylenyl, $C_{1-6}$-alkenyl, $C_{1-6}$-alkynyl, and $C_{1-3}$-alkyl-(C=O)—; or each R" forms together with a R7 or R8, respectively, an $C_{1-3}$-alkylene bridge;

Ar is phenyl or 5 to 6 membered aromatic heterocyclic ring comprising one, two or three N atoms, said phenyl or ring being optionally substituted one or two times with R5;

Cy is 3 to 7 membered aliphatic carbocyclic or heterocyclic ring optionally substituted one or two times with R5;

i is 0, 1, or 2;
k is 0 or 1;
m is 0, 1, 2, 3, or 4;
n is 0, 1, 2, or 3;

or metabolite, N-oxide, pharmaceutically acceptable salt, hydrate, or solvate thereof to a patient in need thereof;
wherein the condition, disease, or disorder is selected from the group consisting of Alzheimer's disease, Parkinsonism linked to chromosome 17, atherosclerosis, Huntington's disease, Parkinson's disease.

11. A method as claimed in claim 10, wherein the method is for treatment of a condition where elimination of lipid hydroperoxides and/or limiting their detrimental effects on cellular macromolecules is desired.

12. A method as claimed in claim 10, wherein the method is for treatment or prevention of a disease or state, either acute or chronic, involving aberrant cellular lipid peroxidation in the central nervous system or in the periphery of the body.

13. The method as claimed in claim 10, wherein said compound is administered simultaneously, separately, or sequentially with another active agent.

14. A method for preparing a compound of formula (I) as defined in claim 1, comprising reacting a compound of formula (IIa) or (IIb)

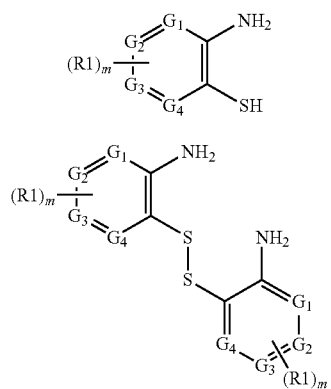

wherein G1, G2, G3, G4, R1, and m are as defined in claim 1;

with a compound of formula (III)

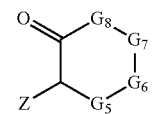

wherein G8 is $C(R8)_2$, or $[CH_2]n$; n, G5, G6, and G7 are as defined in claim 1; and Z is H or halogen;

to obtain a compound of formula (I);

and when R8 is $CH_2$ optionally allowing the obtained compound wherein to oxidize to obtain a compound of formula (I) wherein R8 is —(C=O)—;

and optionally converting the obtained compound to a corresponding pharmaceutically acceptable salt thereof.

* * * * *